(12) United States Patent
Ting et al.

(10) Patent No.: US 7,691,607 B2
(45) Date of Patent: *Apr. 6, 2010

(54) EXPRESSION SYSTEM OF NELL PEPTIDE

(75) Inventors: Kang Ting, Beverly Hills, CA (US); Shunichi Kuroda, Osaka (JP); Ben Wu, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 51 days.

This patent is subject to a terminal disclaimer.

(21) Appl. No.: 11/601,529

(22) Filed: Nov. 17, 2006

(65) Prior Publication Data

US 2007/0128697 A1    Jun. 7, 2007

Related U.S. Application Data

(63) Continuation-in-part of application No. 10/544,553, filed as application No. PCT/US2004/003808 on Feb. 9, 2004, now Pat. No. 7,544,486, and a continuation-in-part of application No. PCT/US2006/005473, filed on Feb. 16, 2006.

(51) Int. Cl.
| | |
|---|---|
| C12N 15/06 | (2006.01) |
| C12N 15/07 | (2006.01) |
| C12N 15/12 | (2006.01) |
| C12N 15/19 | (2006.01) |
| C12N 15/63 | (2006.01) |
| C12N 15/85 | (2006.01) |

(52) U.S. Cl. .......... 435/69.1; 435/320.1; 435/69.8; 435/325; 435/350; 435/351; 435/352; 435/353; 435/354; 435/358; 435/360; 435/363; 435/366; 536/23.1; 536/23.5; 536/24.1

(58) Field of Classification Search ............ None
See application file for complete search history.

(56) References Cited

U.S. PATENT DOCUMENTS

| | | | |
|---|---|---|---|
| 4,394,370 | A | 7/1983 | Jefferies |
| 4,409,332 | A | 10/1983 | Jefferies et al. |
| 5,385,887 | A | 1/1995 | Yim et al. |
| 5,486,359 | A | 1/1996 | Caplan et al. |
| 5,674,725 | A | 10/1997 | Beersten et al. |
| 5,674,844 | A | 10/1997 | Kuberasampath et al. |
| 5,763,416 | A | 6/1998 | Bonadio et al. |
| 5,831,058 | A * | 11/1998 | Fujiwara et al. ........ 536/23.5 |
| 5,854,207 | A | 12/1998 | Lee et al. |
| 5,916,870 | A | 6/1999 | Lee et al. |
| 5,942,496 | A | 8/1999 | Bonadio et al. |
| 5,948,428 | A | 9/1999 | Lee et al. |
| 6,083,690 | A | 7/2000 | Harris et al. |
| 6,200,606 | B1 | 3/2001 | Peterson et al. |
| 6,352,972 | B1 | 3/2002 | Nimni et al. |
| 6,413,998 | B1 | 7/2002 | Petrie et al. |
| 6,462,019 | B1 | 10/2002 | Mundy et al. |
| 2003/0143688 | A1 | 7/2003 | Fujiwara et al. |
| 2006/0111313 | A1 | 5/2006 | Ting |

FOREIGN PATENT DOCUMENTS

| | | | |
|---|---|---|---|
| WO | WO 01/24821 | * | 4/2001 |
| WO | WO 2004/024893 | | 3/2004 |

OTHER PUBLICATIONS

Zhang et al., 2002, J. Clin. Invest. 110:861-870.*
Ting et al., 1999, J. Bone Miner. Res. 14:80-89.*
International Search Report for PCT/US04/03808 filed Feb. 9, 2004, mailed Sep. 19, 2006, 9 pgs.
Beck et al. "Rapid Publication TGF-$\beta_1$ Induces Bone Closure of Skull Defects." J. of Bone Miner. Res. vol. 6, No. 11:1257-1265 (1991).
Bellows et al. "Determination of Numbers of Osteoprogenitors Present in Isolated Fetal Rat Calvaria Cells in Vitro." Dev. Biol. 133, pp. 8-13 (1989).
Burger et al., "Osteoblast and Osteoclast Precursors in Primary Cultures of Calvarial Bone Cells." Anat. Rec. Jan. 1986; 214(1): 32-40. Abstract only.
Chen et al. "Structure, Chromosomal Localization, and Expression Pattern of the Murine *Magp* Gene," J. Biol Chem. vol. 268, No. 36: 27381-27389 (1998).
Crawford et al. "Thrombospondin-1 is a Major Activator of TGF-$\beta_1$ in Vivo." Cell, vol. 93:1159-1170 (1998).
Francois and Bier "Xenopus chordin and *Drosophila* short gastrulation Genes Encode Homologous Proteins Functioning in Dorsal-Ventral Axis Formation" Cell, vol. 80:19-20 (1995).
Gelbart, "Databases in Genomic Research" Science, vol. 282, Oct. 23, 1998.
Hoshi, K. et al., "Fibroblasts of Spinal Ligaments Pathologically Differentiate into Chondrocytes Induced by Recombinant Human Bone Morphogenetic Protein-2: Morphological Examinations for Ossification and Spinal Ligaments" Bone vol. 21, No. 2: 155-162 (1997).
Kim et al. "NELL-1 Enhances Mineralization in Fetal Calvarial Osteoblastic Cells." Plastic Surgery, 599-601 (1999).
Kuroda and Tanizawa "Involvement of Epidermal Growth Factor-like Domain of NELL Proteins in the Novel Protein-Protein Interaction with Protein Kinase C$^1$" Biochem Biophys Res. Commun. 265: 752-757 (1999).
Kuroda et al. "Biochemical Characterization and Expression Analysis of Neural Thrombospondin-1-like Proteins NELL1 and NELL2" Biochem Biophys Res Comm. 265: 79-86 (1999).
Luce and Burrows "The neuronal EGF-related genes NELL1 and NELL2 are expressed in hemopoietic cells and developmentally regulated in the B lineage" Gene 231:121-126 (1999).

(Continued)

*Primary Examiner*—Elizabeth C. Kemmerer
(74) *Attorney, Agent, or Firm*—Squire, Sanders & Dempsey L.L.P.

(57) ABSTRACT

Methods of preparing a NELL peptide are disclosed.

16 Claims, 10 Drawing Sheets

OTHER PUBLICATIONS

Opperman, et al., "TGF-β1, TGF-β2, and TGF-β3 Exhbit Distinct Patterns of Expression During Cranial Suture Formation and Obliteration In Vivo and In Vitro" J. of Bone and Mineral Research, vol. 12, No. 3: 301-310 (1997).

Piccolo et al. "Dorsoventral Patterning in Xenopus: Inhibition of Ventral Signals by Direct Binding of Chordin to BMP-4" Cell, vol. 86: 589-598 (1996).

Siris et al., "Design of NORA, the National Osteoporosis Risk Assessment program: A Longitudinal US Registry of Postmenopausal Women" Osteoporos Int. Suppl. 1: 62-69 (1998).

Takagi et al. "The reaction of the dura to bone morphogenetic protein (BMP) in repair of skull defects" Ann Surg. vol. 196, No. 1: 100-109. Abstract only (1982).

Takami et al. "$CA^{2+}$-ATPase Inhibitors and $Ca^{2+}$-Ionophore Induce Osteoclast-like Cell Formation in the Cocultures of Mouse Bone Marrow Cells and Calvarial Cells" Biochemical and Biophysical Research Comm, vol. 237: 111-115 1997.

Tieu A. et al. "Identification of Human NEL-2 Associated with Premature Suture Fusion." J Dent Res. 77(A):635, Abstract only (1998).

Ting et al. "Human NELL1 Expressed in Unilaterial Coronal Synostosis" J. of Bone and Mineral Res. vol. 14: 80-89 (1999).

Ting et al. "NELL-1 Enhances Mineralization in Fetal Calvarial Osteoblastic Cells." *J. Dent. Res.* 79:625 (2000).

Ting et al. "NEL-2 Expressed in Unilateral Prematurely Fusing and Fused Coronal Sutures." J Dent Res. 77(B):2224 (1998) Abstract only.

Ting et al. "NEL-2 Gene is associated with bone formation in Craniosynostosis", Plastic Surgery, 602-603 (no date).

Toriumi et al. "Mandibular Reconstruction With a Recombinant Bone-Inducing Factor." Arch. Otolaryngol. Head Neck Surg. vol. 117: 1101-1112 (1991).

Watanabe, T.K. et al. "Cloning and Characterization of Two Novel Human cDNAs (NELL1 and NELL2) Encoding Proteins with Six EGF-like Repeats." Genomics, vol. 38, 273-276 (1996).

Wobus, "Potential of embryonic stem cells" Molecular Aspects of Medicine (2001), 22/3 (149-164) (Abstract only) 1 pg.

Yasko et al. "The Healing of Segmental Bone Defects, Induced by Recombinant Human Bone Morphogenetic Protein (rhBMP-2)." J. of Bone and Joint Surgery vol. 74A, No. 5: 659-670 (1992).

Zhang et al., "Graniosynostosis in transgenic mice overexpressing Nell-1" The J. of Clinical Investigation, vol. 110, No. 6 (2002).

Liu et al., "Simultaneous Detection of Multiple Bone-Related mRNAs and Protein Expression during Osteoblast Differentiation: Polymerase Chain Reaction and Immunocytochemical Studies at the Single Cell Level", Developmental Biology, vol. 166, pp. 220-234 (1994).

Zhang et al., "NELL-1 Overexpression Transgenic Mice Simulate Human Craniosynostosis", Surgical Forum, vol. 52, pp. 576-578 (2001).

International Search Report for PCT/US2008/054779, mailed Aug. 1, 2008, 11 pgs.

Aghaloo et al., "Nell-1-induced bone regeneration in calvarial defects", Am. J. Pathol., vol. 169, pp. 903-915 (2006).

Cowan et al., "Nell-1 induced bone formation within the distracted intermaxillary suture", Bone, vol. 38, pp. 48-58 (2006).

Lu et al., "The osteoinductive properties of Nell-1 in a rat spinal fusion model", The Spine J. vol. 7, No. 1, pp. 50-60 (2007).

International Search Report for PCT/US2007/84074, mailed Sep. 22, 2008, 12 pgs.

* cited by examiner

| | | |
|---|---|---|
| atg aaa ttc tta gtc aac gtt gca cta gtt ttt atg gtc gtg tac att<br>Met Lys Phe Leu Val Asn Val Ala Leu Val Phe Met Val Val Tyr Ile<br>1                 5                     10                   15 | | 48 |
| tct tac atc tat gcg atg ccg atg gat gtg att tta gtt ttg tgg ttc<br>Ser Tyr Ile Tyr Ala Met Pro Met Asp Val Ile Leu Val Leu Trp Phe<br>                 20                       25                   30 | | 96 |
| tgt gta tgc acc gcc agg aca gtg ttg ggc ttt ggg atg gac cct gac<br>Cys Val Cys Thr Ala Arg Thr Val Leu Gly Phe Gly Met Asp Pro Asp<br>         35                       40                     45 | | 144 |
| ctt cag ctg gac atc atc tca gag ctc gac ctg gtg aac acc acc ctg<br>Leu Gln Leu Asp Ile Ile Ser Glu Leu Asp Leu Val Asn Thr Thr Leu<br>     50                     55                     60 | | 192 |
| gga gtc acg cag gtg gct gga ctg cac aac gcc agt aaa gca ttc cta<br>Gly Val Thr Gln Val Ala Gly Leu His Asn Ala Ser Lys Ala Phe Leu<br>65                     70                     75                  80 | | 240 |
| ttt caa gat gta cag aga gag atc cat tcg gcc cct cac gtg agt gag<br>Phe Gln Asp Val Gln Arg Glu Ile His Ser Ala Pro His Val Ser Glu<br>                 85                       90                   95 | | 288 |
| aag ctg atc cag cta ttc cgg aat aag agc gag ttc acc ttt ttg gct<br>Lys Leu Ile Gln Leu Phe Arg Asn Lys Ser Glu Phe Thr Phe Leu Ala<br>                 100                    105               110 | | 336 |
| aca gtg cag cag aaa cca tcc acc tca ggg gtg ata ctg tcc atc cgg<br>Thr Val Gln Gln Lys Pro Ser Thr Ser Gly Val Ile Leu Ser Ile Arg<br>             115                    120                   125 | | 384 |
| gag ctg gag cac agc tat ttt gaa ctg gag agc agt ggc cca aga gaa<br>Glu Leu Glu His Ser Tyr Phe Glu Leu Glu Ser Ser Gly Pro Arg Glu<br>     130                     135                    140 | | 432 |
| gag ata cgc tac cat tac ata cat ggt gga aag ccc agg act gag gcc<br>Glu Ile Arg Tyr His Tyr Ile His Gly Gly Lys Pro Arg Thr Glu Ala<br>145                   150                    155                 160 | | 480 |
| ctt ccc tac cgc atg gca gac gga caa tgg cac aag gtc gcg ctg tca<br>Leu Pro Tyr Arg Met Ala Asp Gly Gln Trp His Lys Val Ala Leu Ser<br>                 165                    170                   175 | | 528 |
| gtg agc gcc tct cac ctc ctg ctc cac atc gac tgc aat agg att tac<br>Val Ser Ala Ser His Leu Leu Leu His Ile Asp Cys Asn Arg Ile Tyr<br>             180                    185                   190 | | 576 |
| gag cgt gtg ata gac cct ccg gag acc aac ctt cct cca gga agc aat<br>Glu Arg Val Ile Asp Pro Pro Glu Thr Asn Leu Pro Pro Gly Ser Asn<br>     195                     200                    205 | | 624 |
| ctg tgg ctt ggg caa cgt aac caa aag cat ggc ttt ttc aaa gga atc<br>Leu Trp Leu Gly Gln Arg Asn Gln Lys His Gly Phe Phe Lys Gly Ile<br>     210                     215                    220 | | 672 |
| atc caa gat ggt aag atc atc ttc atg ccg aat ggt ttc atc aca cag | | 720 |

FIGURE 2A

```
                Ile Gln Asp Gly Lys Ile Ile Phe Met Pro Asn Gly Phe Ile Thr Gln
                225             230             235             240 tgt ccc aac ctc aat cgc act tgc cca aca tgc agt gac ttc ctg agc                    768
Cys Pro Asn Leu Asn Arg Thr Cys Pro Thr Cys Ser Asp Phe Leu Ser
                245             250             255 ctg gtt caa gga ata atg gat ttg caa gag ctt ttg gcc aag atg act                    816
Leu Val Gln Gly Ile Met Asp Leu Gln Glu Leu Leu Ala Lys Met Thr
            260             265             270 gca aaa ctg aat tat gca gag acg aga ctt ggt caa ctg gaa aat tgc                    864
Ala Lys Leu Asn Tyr Ala Glu Thr Arg Leu Gly Gln Leu Glu Asn Cys
        275             280             285 cac tgt gag aag acc tgc caa gtg agt ggg ctg ctc tac agg gac caa                    912
His Cys Glu Lys Thr Cys Gln Val Ser Gly Leu Leu Tyr Arg Asp Gln
        290             295             300 gac tcc tgg gtg gat ggt gac aac tgt ggg aac tgc acg tgc aaa agt                    960
Asp Ser Trp Val Asp Gly Asp Asn Cys Gly Asn Cys Thr Cys Lys Ser
305             310             315             320 ggt gcc gtg gag tgc cgc agg atg tcc tgt ccc ccg ctc aac tgt tcc                    1008
Gly Ala Val Glu Cys Arg Arg Met Ser Cys Pro Pro Leu Asn Cys Ser
            325             330             335 ccg gac tca ctt cct gtg cac att tcc ggc cag tgt tgt aaa gtt tgc                    1056
Pro Asp Ser Leu Pro Val His Ile Ser Gly Gln Cys Cys Lys Val Cys
                340             345             350 aga cca aaa tgt atc tat gga gga aaa gtt ctt gct gag ggc cag cgg                    1104
Arg Pro Lys Cys Ile Tyr Gly Gly Lys Val Leu Ala Glu Gly Gln Arg
            355             360             365 att tta acc aag acc tgc cgg gaa tgt cga ggt gga gtc ttg gta aaa                    1152
Ile Leu Thr Lys Thr Cys Arg Glu Cys Arg Gly Gly Val Leu Val Lys
        370             375             380 atc aca gaa gct tgc cct cct ttg aac tgc tca gca aag gat cat att                    1200
Ile Thr Glu Ala Cys Pro Pro Leu Asn Cys Ser Ala Lys Asp His Ile
385             390             395             400 ctt cca gag aat cag tgc tgc agg gtc tgc cca ggt cat aac ttc tgt                    1248
Leu Pro Glu Asn Gln Cys Cys Arg Val Cys Pro Gly His Asn Phe Cys
            405             410             415 gca gaa gca cct aag tgc gga gaa aac tcg gaa tgc aaa aat tgg aat                    1296
Ala Glu Ala Pro Lys Cys Gly Glu Asn Ser Glu Cys Lys Asn Trp Asn
            420             425             430 aca aaa gca acc tgt gag tgc aag aat gga tac atc tct gtc cag ggc                    1344
Thr Lys Ala Thr Cys Glu Cys Lys Asn Gly Tyr Ile Ser Val Gln Gly
        435             440             445 aac tct gca tac tgt gaa gat att gat gag tgt gca gct aaa atg cac                    1392
Asn Ser Ala Tyr Cys Glu Asp Ile Asp Glu Cys Ala Ala Lys Met His
```

FIGURE 2B

```
                    450                     455                      460
tat tgt cat gcc aac acc gtg tgt gtc aac ttg ccg ggg ttg tat cgc      1440
Tyr Cys His Ala Asn Thr Val Cys Val Asn Leu Pro Gly Leu Tyr Arg
465                 470                  475                     480 tgt gac tgc gtc cca ggg tac atc cgt gtg gat gac ttc tct tgt acg      1488
Cys Asp Cys Val Pro Gly Tyr Ile Arg Val Asp Asp Phe Ser Cys Thr
                485                  490                 495 gag cat gat gat tgt ggc agc gga caa cac aac tgc gac aaa aat gcc      1536
Glu His Asp Asp Cys Gly Ser Gly Gln His Asn Cys Asp Lys Asn Ala
            500                  505                 510 atc tgt acc aac aca gtc cag gga cac agc tgc acc tgc cag ccg ggt      1584
Ile Cys Thr Asn Thr Val Gln Gly His Ser Cys Thr Cys Gln Pro Gly
        515                  520                 525 tac gtg gga aat ggc acc atc tgc aaa gca ttc tgt gaa gag ggt tgc      1632
Tyr Val Gly Asn Gly Thr Ile Cys Lys Ala Phe Cys Glu Glu Gly Cys
    530                  535                 540 aga tac gga ggt acc tgt gtg gct cct aac aag tgt gtc tgt cct tct      1680
Arg Tyr Gly Gly Thr Cys Val Ala Pro Asn Lys Cys Val Cys Pro Ser
545                  550                 555                 560 gga ttc acg gga agc cac tgt gag aaa gat att gat gaa tgc gca gag      1728
Gly Phe Thr Gly Ser His Cys Glu Lys Asp Ile Asp Glu Cys Ala Glu
                565                  570                 575 gga ttc gtt gaa tgc cac aac tac tcc cgc tgt gtt aac ctg cca ggg      1776
Gly Phe Val Glu Cys His Asn Tyr Ser Arg Cys Val Asn Leu Pro Gly
            580                  585                 590 tgg tac cac tgt gag tgc aga agc ggt ttc cat gac gat ggg acc tac      1824
Trp Tyr His Cys Glu Cys Arg Ser Gly Phe His Asp Asp Gly Thr Tyr
        595                  600                 605 tca ctg tcc ggg gag tcc tgc att gat atc gat gaa tgt gcc tta aga      1872
Ser Leu Ser Gly Glu Ser Cys Ile Asp Ile Asp Glu Cys Ala Leu Arg
    610                  615                 620 act cac act tgt tgg aat gac tct gcc tgc atc aac tta gca gga gga      1920
Thr His Thr Cys Trp Asn Asp Ser Ala Cys Ile Asn Leu Ala Gly Gly
625                  630                 635                 640 ttt gac tgc ctg tgt ccc tct ggg ccc tcc tgc tct ggt gac tgt ccc      1968
Phe Asp Cys Leu Cys Pro Ser Gly Pro Ser Cys Ser Gly Asp Cys Pro
                645                  650                 655 cac gaa gga ggg ctg aag cat aat ggg cag gtg tgg att ctg aga gaa      2016
His Glu Gly Gly Leu Lys His Asn Gly Gln Val Trp Ile Leu Arg Glu
            660                  665                 670 gac agg tgt tca gtc tgt tcc tgc aag gat ggg aag ata ttc tgc cgg      2064
Asp Arg Cys Ser Val Cys Ser Cys Lys Asp Gly Lys Ile Phe Cys Arg
        675                  680                 685
```

FIGURE 2C

```
cgg aca gct tgt gat tgc cag aat cca aat gtt gac ctt ttt tgc tgc    2112
Arg Thr Ala Cys Asp Cys Gln Asn Pro Asn Val Asp Leu Phe Cys Cys
    690                 695                 700 cca gag tgc gat acc agg gtc acc agc caa tgt tta gat caa agt gga    2160
Pro Glu Cys Asp Thr Arg Val Thr Ser Gln Cys Leu Asp Gln Ser Gly
705                 710                 715                 720 cag aag ctc tat cga agt gga gac aac tgg acc cac agc tgc cag cag    2208
Gln Lys Leu Tyr Arg Ser Gly Asp Asn Trp Thr His Ser Cys Gln Gln
                725                 730                 735 tgc cga tgt ctg gaa gga gag gca gac tgc tgg cct ctg gct tgc cct    2256
Cys Arg Cys Leu Glu Gly Glu Ala Asp Cys Trp Pro Leu Ala Cys Pro
            740                 745                 750 agt ttg ggc tgt gaa tac aca gcc atg ttt gaa ggg gag tgt tgt ccc    2304
Ser Leu Gly Cys Glu Tyr Thr Ala Met Phe Glu Gly Glu Cys Cys Pro
        755                 760                 765 cga tgt gtc agt gac ccc tgc ctg gct ggt aat att gcc tat gac atc    2352
Arg Cys Val Ser Asp Pro Cys Leu Ala Gly Asn Ile Ala Tyr Asp Ile
    770                 775                 780 aga aaa act tgc ctg gac agc ttt ggt gtt tcg agg ctg agc gga gcc    2400
Arg Lys Thr Cys Leu Asp Ser Phe Gly Val Ser Arg Leu Ser Gly Ala
785                 790                 795                 800 gtg tgg aca atg gct gga tct cct tgt aca acc tgc aaa tgc aag aat    2448
Val Trp Thr Met Ala Gly Ser Pro Cys Thr Thr Cys Lys Cys Lys Asn
                805                 810                 815 ggg aga gtc tgc tgc tct gtg gat ctg gag tgt att gag aat aac tga    2496
Gly Arg Val Cys Cys Ser Val Asp Leu Glu Cys Ile Glu Asn Asn
            820                 825                 830 gac tac aag gac gac gat gac aag                                    2520
Asp Tyr Lys Asp Asp Asp Asp Lys
                835
```

FIGURE 2D

Figure 3A
Figure 3B
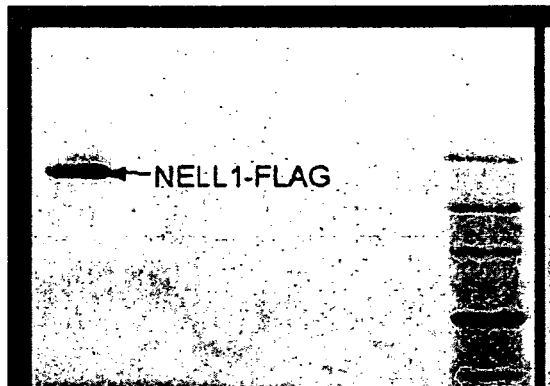
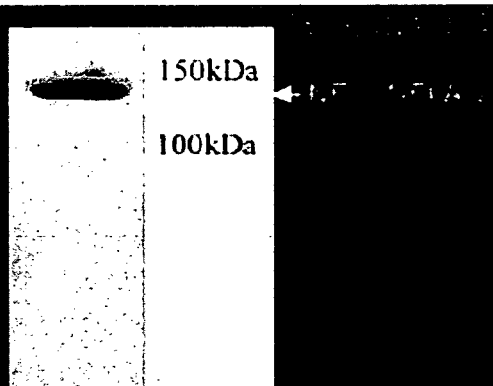
Purified NELL1-FLAG protein
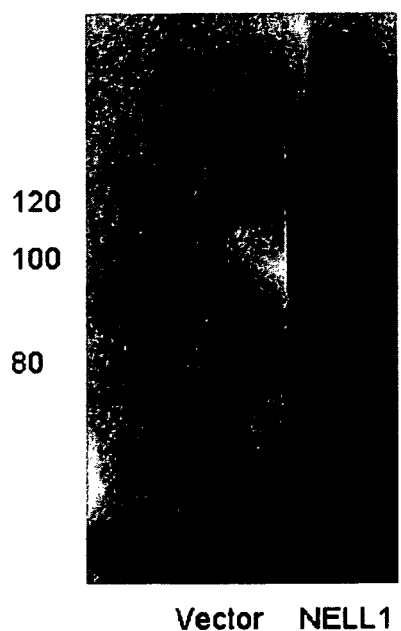
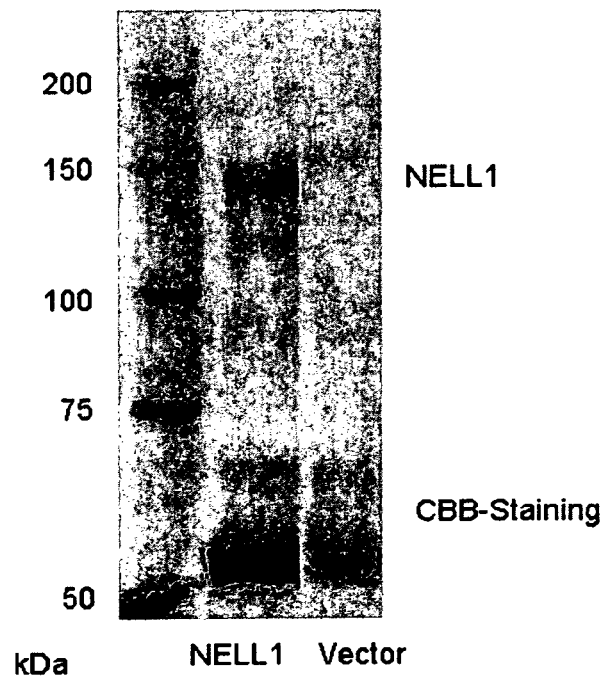
Figure 3C
Figure 3D Signal Peptide NELL1 : MPMDLILVVWFCVCTA          16AA
NELL2 : MESRVLLRTFCLIFGLGAVWG     21AA+2AA for linker
IL-2  : MYRMQLLSCIALSLALVTNS      20AA+2AA for linker pcDNA3.1-hNELL1-c-myc/His
pIL2-hNELL1-c-myc/His
pN2-hNELL1-c-myc/His

```
         1          11         21         31         41         51
  1  MPMDLILVVW FCVCTARTVV GFGMDPDLQM DIVTELDLVN TTLGVAQVSG MHNAS
 61  QDIEREIHAA PHVSEKLIQL FQNKSEFTIL ATVQQKPSTS GVILSIRELE HSYFE
121  LRDEIRYHYI HNGKPRTEAL PYRMADGQWH KVALSVSASH LLLHVDCNRI YERVI
181  NLPPGINLWL GQRNQKHGLF KGIIQDGKII FMPNGYITQC PNLNHTCPTC SDFLS
241  MDLQELLAKM TAKLNYAETR LSQLENCHCE KTCQVSGLLY RDQDSWVDGD HCRNC
301  AVECRRMSCP PLNCSPDSLP VHIAGQCCKV CRPKCIYGGK VLAEGQRILT KSCRE
361  LVKITEMCPP LNCSEKDHIL PENQCCRVCR GHNFCAEGPK CGENSECKNW NTKAT
421  GYISVQGDSA YCEDIDECAA KMHYCHANTV CVNLPGLYRC DCVPGYIRVD DFSCT
481  GSGQHNCDEN AICTNTVQGH SCTCKPGYVG NGTICRAFCE EGCRYGGTCV APNKC
541  FTGSHCEKDI DECSEGIIEC HNHSRCVNLP GWYHCECRSG FHDDGTYSLS GESCI
601  ALRTHTCWND SACINLAGGF DCLCPSGPSC SGDCPHEGGL KHNGQVWTLK EDRCS
661  DGKIFCRRTA CDCQNPSADL FCCPECDTRV TSQCLDQNGH KLYRSGDNWT HSCQQ
721  GEVDCWPLTC PNLSCEYTAI LEGECCPRCV SDPCLADNIT YDIRKTCLDS YGVSR
781  WTMAGSPCTT CKCKNGRVCC SVDFECLQNN
```

*Human NELL1 Amino Acid Sequence*

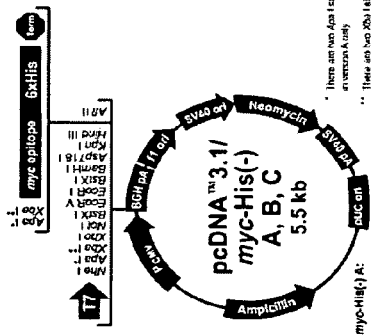

Figure 4A

SEQUENCE LISTING

<160> NUMBER OF SEQ ID NOS: 18

<210> SEQ ID NO 1
<211> LENGTH: 2433
<212> TYPE: DNA
<213> ORGANISM: Homo sapiens
<220> FEATURE:
<221> NAME/KEY: CDS
<222> LOCATION: (1)..(2433)

<400> SEQUENCE: 1

| | | | | | | | | | | | | | | | | |
|---|---|---|---|---|---|---|---|---|---|---|---|---|---|---|---|---|
| atg | ccg | atg | gat | ttg | att | tta | gtt | gtg | tgg | ttc | tgt | gtg | tgc | act | gcc | 48 |
| Met | Pro | Met | Asp | Leu | Ile | Leu | Val | Val | Trp | Phe | Cys | Val | Cys | Thr | Ala | |
| 1 | | | | 5 | | | | | 10 | | | | | 15 | | |

| agg | aca | gtg | gtg | ggc | ttt | ggg | atg | gac | cct | gac | ctt | cag | atg | gat | atc | 96 |
|---|---|---|---|---|---|---|---|---|---|---|---|---|---|---|---|---|
| Arg | Thr | Val | Val | Gly | Phe | Gly | Met | Asp | Pro | Asp | Leu | Gln | Met | Asp | Ile | |
| | | | 20 | | | | | 25 | | | | | 30 | | | |

| gtc | acc | gag | ctt | gac | ctt | gtg | aac | acc | acc | ctt | gga | gtt | gct | cag | gtg | 144 |
|---|---|---|---|---|---|---|---|---|---|---|---|---|---|---|---|---|
| Val | Thr | Glu | Leu | Asp | Leu | Val | Asn | Thr | Thr | Leu | Gly | Val | Ala | Gln | Val | |
| | | 35 | | | | | 40 | | | | | 45 | | | | |

| tct | gga | atg | cac | aat | gcc | agc | aaa | gca | ttt | tta | ttt | caa | gac | ata | gaa | 192 |
|---|---|---|---|---|---|---|---|---|---|---|---|---|---|---|---|---|
| Ser | Gly | Met | His | Asn | Ala | Ser | Lys | Ala | Phe | Leu | Phe | Gln | Asp | Ile | Glu | |
| | 50 | | | | | 55 | | | | | 60 | | | | | |

| aga | gag | atc | cat | gca | gct | cct | cat | gtg | agt | gag | aaa | tta | att | cag | ctg | 240 |
|---|---|---|---|---|---|---|---|---|---|---|---|---|---|---|---|---|
| Arg | Glu | Ile | His | Ala | Ala | Pro | His | Val | Ser | Glu | Lys | Leu | Ile | Gln | Leu | |
| 65 | | | | 70 | | | | | 75 | | | | | 80 | | |

| ttc | cag | aac | aag | agt | gaa | ttc | acc | att | ttg | gcc | act | gta | cag | cag | aag | 288 |
|---|---|---|---|---|---|---|---|---|---|---|---|---|---|---|---|---|
| Phe | Gln | Asn | Lys | Ser | Glu | Phe | Thr | Ile | Leu | Ala | Thr | Val | Gln | Gln | Lys | |
| | | | | 85 | | | | | 90 | | | | | 95 | | |

| cca | tcc | act | tca | gga | gtg | ata | ctg | tcc | att | cga | gaa | ctg | gag | cac | agc | 336 |
|---|---|---|---|---|---|---|---|---|---|---|---|---|---|---|---|---|
| Pro | Ser | Thr | Ser | Gly | Val | Ile | Leu | Ser | Ile | Arg | Glu | Leu | Glu | His | Ser | |
| | | | 100 | | | | | 105 | | | | | 110 | | | |

| tat | ttt | gaa | ctg | gag | agc | agt | ggc | ctg | agg | gat | gag | att | cgg | tat | cac | 384 |
|---|---|---|---|---|---|---|---|---|---|---|---|---|---|---|---|---|
| Tyr | Phe | Glu | Leu | Glu | Ser | Ser | Gly | Leu | Arg | Asp | Glu | Ile | Arg | Tyr | His | |
| | | 115 | | | | | 120 | | | | | 125 | | | | |

| tac | ata | cac | aat | ggg | aag | cca | agg | aca | gag | gca | ctt | cct | tac | cgc | atg | 432 |
|---|---|---|---|---|---|---|---|---|---|---|---|---|---|---|---|---|
| Tyr | Ile | His | Asn | Gly | Lys | Pro | Arg | Thr | Glu | Ala | Leu | Pro | Tyr | Arg | Met | |
| | 130 | | | | | 135 | | | | | 140 | | | | | |

| gca | gat | gga | caa | tgg | cac | aag | gtt | gca | ctg | tca | gtt | agc | gcc | tct | cat | 480 |
|---|---|---|---|---|---|---|---|---|---|---|---|---|---|---|---|---|
| Ala | Asp | Gly | Gln | Trp | His | Lys | Val | Ala | Leu | Ser | Val | Ser | Ala | Ser | His | |
| 145 | | | | 150 | | | | | 155 | | | | | 160 | | |

| ctc | ctg | ctc | cat | gtc | gac | tgt | aac | agg | att | tat | gag | cgt | gtg | ata | gac | 528 |
|---|---|---|---|---|---|---|---|---|---|---|---|---|---|---|---|---|
| Leu | Leu | Leu | His | Val | Asp | Cys | Asn | Arg | Ile | Tyr | Glu | Arg | Val | Ile | Asp | |
| | | | | 165 | | | | | 170 | | | | | 175 | | |

| cct | cca | gat | acc | aac | ctt | ccc | cca | gga | atc | aat | tta | tgg | ctt | ggc | cag | 576 |
|---|---|---|---|---|---|---|---|---|---|---|---|---|---|---|---|---|
| Pro | Pro | Asp | Thr | Asn | Leu | Pro | Pro | Gly | Ile | Asn | Leu | Trp | Leu | Gly | Gln | |
| | | | 180 | | | | | 185 | | | | | 190 | | | |

| cgc | aac | caa | aag | cat | ggc | tta | ttc | aaa | ggg | atc | atc | caa | gat | ggg | aag | 624 |
|---|---|---|---|---|---|---|---|---|---|---|---|---|---|---|---|---|
| Arg | Asn | Gln | Lys | His | Gly | Leu | Phe | Lys | Gly | Ile | Ile | Gln | Asp | Gly | Lys | |
| | | 195 | | | | | 200 | | | | | 205 | | | | |

| atc | atc | ttt | atg | ccg | aat | gga | tat | ata | aca | cag | tgt | cca | aat | cta | aat | 672 |
|---|---|---|---|---|---|---|---|---|---|---|---|---|---|---|---|---|
| Ile | Ile | Phe | Met | Pro | Asn | Gly | Tyr | Ile | Thr | Gln | Cys | Pro | Asn | Leu | Asn | |
| | 210 | | | | | 215 | | | | | 220 | | | | | |

| cac | act | tgc | cca | acc | tgc | agt | gat | ttc | tta | agc | ctg | gtg | caa | gga | ata | 720 |
|---|---|---|---|---|---|---|---|---|---|---|---|---|---|---|---|---|
| His | Thr | Cys | Pro | Thr | Cys | Ser | Asp | Phe | Leu | Ser | Leu | Val | Gln | Gly | Ile | |
| 225 | | | | 230 | | | | | 235 | | | | | 240 | | |

| atg | gat | tta | caa | gag | ctt | ttg | gcc | aag | atg | act | gca | aaa | cta | aat | tat | 768 |
|---|---|---|---|---|---|---|---|---|---|---|---|---|---|---|---|---|
| Met | Asp | Leu | Gln | Glu | Leu | Leu | Ala | Lys | Met | Thr | Ala | Lys | Leu | Asn | Tyr | |
| | | | | 245 | | | | | 250 | | | | | 255 | | |

```
gca gag aca aga ctt agt caa ttg gaa aac tgt cat tgt gag aag act    816
Ala Glu Thr Arg Leu Ser Gln Leu Glu Asn Cys His Cys Glu Lys Thr
        260                 265                 270 tgt caa gtg agt gga ctg ctc tat cga gat caa gac tct tgg gta gat    864
Cys Gln Val Ser Gly Leu Leu Tyr Arg Asp Gln Asp Ser Trp Val Asp
            275                 280                 285 ggt gac cat tgc agg aac tgc act tgc aaa agt ggt gcc gtg gaa tgc    912
Gly Asp His Cys Arg Asn Cys Thr Cys Lys Ser Gly Ala Val Glu Cys
        290                 295                 300 cga agg atg tcc tgt ccc cct ctc aat tgc tcc cca gac tcc ctc cca    960
Arg Arg Met Ser Cys Pro Pro Leu Asn Cys Ser Pro Asp Ser Leu Pro
305                 310                 315                 320 gta cac att gct ggc cag tgt tgt aag gtc tgc cga cca aaa tgt atc   1008
Val His Ile Ala Gly Gln Cys Cys Lys Val Cys Arg Pro Lys Cys Ile
                325                 330                 335 tat gga gga aaa gtt ctt gca gaa ggc cag cgg att tta acc aag agc   1056
Tyr Gly Gly Lys Val Leu Ala Glu Gly Gln Arg Ile Leu Thr Lys Ser
            340                 345                 350 tgt cgg gaa tgc cga ggt gga gtt tta gta aaa att aca gaa atg tgt   1104
Cys Arg Glu Cys Arg Gly Gly Val Leu Val Lys Ile Thr Glu Met Cys
        355                 360                 365 cct cct ttg aac tgc tca gaa aag gat cac att ctt cct gag aat cag   1152
Pro Pro Leu Asn Cys Ser Glu Lys Asp His Ile Leu Pro Glu Asn Gln
370                 375                 380 tgc tgc cgt gtc tgt aga ggt cat aac ttt tgt gca gaa gga cct aaa   1200
Cys Cys Arg Val Cys Arg Gly His Asn Phe Cys Ala Glu Gly Pro Lys
385                 390                 395                 400 tgt ggt gaa aac tca gag tgc aaa aac tgg aat aca aaa gct act tgt   1248
Cys Gly Glu Asn Ser Glu Cys Lys Asn Trp Asn Thr Lys Ala Thr Cys
                405                 410                 415 gag tgc aag agt ggt tac atc tct gtc cag gga gac tct gcc tac tgt   1296
Glu Cys Lys Ser Gly Tyr Ile Ser Val Gln Gly Asp Ser Ala Tyr Cys
            420                 425                 430 gaa gat att gat gag tgt gca gct aag atg cat tac tgt cat gcc aat   1344
Glu Asp Ile Asp Glu Cys Ala Ala Lys Met His Tyr Cys His Ala Asn
        435                 440                 445 act gtg tgt gtc aac ctt cct ggg tta tat cgc tgt gac tgt gtc cca   1392
Thr Val Cys Val Asn Leu Pro Gly Leu Tyr Arg Cys Asp Cys Val Pro
450                 455                 460 gga tac att cgt gtg gat gac ttc tct tgt aca gaa cac gat gaa tgt   1440
Gly Tyr Ile Arg Val Asp Asp Phe Ser Cys Thr Glu His Asp Glu Cys
465                 470                 475                 480 ggc agc ggc cag cac aac tgt gat gag aat gcc atc tgc acc aac act   1488
Gly Ser Gly Gln His Asn Cys Asp Glu Asn Ala Ile Cys Thr Asn Thr
                485                 490                 495 gtc cag gga cac agc tgc acc tgc aaa ccg ggc tac gtg ggg aac ggg   1536
Val Gln Gly His Ser Cys Thr Cys Lys Pro Gly Tyr Val Gly Asn Gly
            500                 505                 510 acc atc tgc aga gct ttc tgt gaa gag ggc tgc aga tac ggt gga acg   1584
Thr Ile Cys Arg Ala Phe Cys Glu Glu Gly Cys Arg Tyr Gly Gly Thr
        515                 520                 525 tgt gtg gct ccc aac aaa tgt gtc tgt cca tct gga ttc aca gga agc   1632
Cys Val Ala Pro Asn Lys Cys Val Cys Pro Ser Gly Phe Thr Gly Ser
530                 535                 540 cac tgc gag aaa gat att gat gaa tgt tca gag gga atc att gag tgc   1680
His Cys Glu Lys Asp Ile Asp Glu Cys Ser Glu Gly Ile Ile Glu Cys
545                 550                 555                 560 cac aac cat tcc cgc tgc gtt aac ctg cca ggg tgg tac cac tgt gag   1728
His Asn His Ser Arg Cys Val Asn Leu Pro Gly Trp Tyr His Cys Glu
                565                 570                 575
```

```
tgc aga agc ggt ttc cat gac gat ggg acc tat tca ctg tcc ggg gag    1776
Cys Arg Ser Gly Phe His Asp Asp Gly Thr Tyr Ser Leu Ser Gly Glu
            580                 585                 590 tcc tgt att gac att gat gaa tgt gcc tta aga act cac acc tgt tgg    1824
Ser Cys Ile Asp Ile Asp Glu Cys Ala Leu Arg Thr His Thr Cys Trp
        595                 600                 605 aac gat tct gcc tgc atc aac ctg gca ggg ggt ttt gac tgt ctc tgc    1872
Asn Asp Ser Ala Cys Ile Asn Leu Ala Gly Gly Phe Asp Cys Leu Cys
610                 615                 620 ccc tct ggg ccc tcc tgc tct ggt gac tgt cct cat gaa ggg ggg ctg    1920
Pro Ser Gly Pro Ser Cys Ser Gly Asp Cys Pro His Glu Gly Gly Leu
625                 630                 635                 640 aag cac aat ggc cag gtg tgg acc ttg aaa gaa gac agg tgt tct gtc    1968
Lys His Asn Gly Gln Val Trp Thr Leu Lys Glu Asp Arg Cys Ser Val
                645                 650                 655 tgc tcc tgc aag gat ggc aag ata ttc tgc cga cgg aca gct tgt gat    2016
Cys Ser Cys Lys Asp Gly Lys Ile Phe Cys Arg Arg Thr Ala Cys Asp
            660                 665                 670 tgc cag aat cca agt gct gac cta ttc tgt tgc cca gaa tgt gac acc    2064
Cys Gln Asn Pro Ser Ala Asp Leu Phe Cys Cys Pro Glu Cys Asp Thr
        675                 680                 685 aga gtc aca agt caa tgt tta gac caa aat ggt cac aag ctg tat cga    2112
Arg Val Thr Ser Gln Cys Leu Asp Gln Asn Gly His Lys Leu Tyr Arg
690                 695                 700 agt gga gac aat tgg acc cat agc tgt cag cag tgt cgg tgt ctg gaa    2160
Ser Gly Asp Asn Trp Thr His Ser Cys Gln Gln Cys Arg Cys Leu Glu
705                 710                 715                 720 gga gag gta gat tgc tgg cca ctc act tgc ccc aac ttg agc tgt gag    2208
Gly Glu Val Asp Cys Trp Pro Leu Thr Cys Pro Asn Leu Ser Cys Glu
                725                 730                 735 tat aca gct atc tta gaa ggg gaa tgt tgt ccc cgc tgt gtc agt gac    2256
Tyr Thr Ala Ile Leu Glu Gly Glu Cys Cys Pro Arg Cys Val Ser Asp
            740                 745                 750 ccc tgc cta gct gat aac atc acc tat gac atc aga aaa act tgc ctg    2304
Pro Cys Leu Ala Asp Asn Ile Thr Tyr Asp Ile Arg Lys Thr Cys Leu
        755                 760                 765 gac agc tat ggt gtt tca cgg ctt agt ggc tca gtg tgg acg atg gct    2352
Asp Ser Tyr Gly Val Ser Arg Leu Ser Gly Ser Val Trp Thr Met Ala
770                 775                 780 gga tct ccc tgc aca acc tgt aaa tgc aag aat gga aga gtc tgt tgt    2400
Gly Ser Pro Cys Thr Thr Cys Lys Cys Lys Asn Gly Arg Val Cys Cys
785                 790                 795                 800 tct gtg gat ttt gag tgt ctt caa aat aat tga                        2433
Ser Val Asp Phe Glu Cys Leu Gln Asn Asn
                805                 810

<210> SEQ ID NO 2
<211> LENGTH: 810
<212> TYPE: PRT
<213> ORGANISM: Homo sapiens

<400> SEQUENCE: 2

Met Pro Met Asp Leu Ile Leu Val Val Trp Phe Cys Val Cys Thr Ala
1               5                   10                  15

Arg Thr Val Val Gly Phe Gly Met Asp Pro Asp Leu Gln Met Asp Ile
            20                  25                  30

Val Thr Glu Leu Asp Leu Val Asn Thr Thr Leu Gly Val Ala Gln Val
        35                  40                  45

Ser Gly Met His Asn Ala Ser Lys Ala Phe Leu Phe Gln Asp Ile Glu
```

-continued

```
                50                  55                  60
Arg Glu Ile His Ala Ala Pro His Val Ser Glu Lys Leu Ile Gln Leu
 65                  70                  75                  80

Phe Gln Asn Lys Ser Glu Phe Thr Ile Leu Ala Thr Val Gln Gln Lys
                 85                  90                  95

Pro Ser Thr Ser Gly Val Ile Leu Ser Ile Arg Glu Leu Glu His Ser
                100                 105                 110

Tyr Phe Glu Leu Glu Ser Ser Gly Leu Arg Asp Glu Ile Arg Tyr His
                115                 120                 125

Tyr Ile His Asn Gly Lys Pro Arg Thr Glu Ala Leu Pro Tyr Arg Met
130                 135                 140

Ala Asp Gly Gln Trp His Lys Val Ala Leu Ser Val Ser Ala Ser His
145                 150                 155                 160

Leu Leu Leu His Val Asp Cys Asn Arg Ile Tyr Glu Arg Val Ile Asp
                165                 170                 175

Pro Pro Asp Thr Asn Leu Pro Pro Gly Ile Asn Leu Trp Leu Gly Gln
                180                 185                 190

Arg Asn Gln Lys His Gly Leu Phe Lys Gly Ile Ile Gln Asp Gly Lys
                195                 200                 205

Ile Ile Phe Met Pro Asn Gly Tyr Ile Thr Gln Cys Pro Asn Leu Asn
                210                 215                 220

His Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Ser Gln Leu Glu Asn Cys His Cys Glu Lys Thr
                260                 265                 270

Cys Gln Val Ser Gly Leu Leu Tyr Arg Asp Gln Asp Ser Trp Val Asp
                275                 280                 285

Gly Asp His Cys Arg Asn Cys Thr Cys Lys Ser Gly Ala Val Glu Cys
290                 295                 300

Arg Arg Met Ser Cys Pro Pro Leu Asn Cys Ser Pro Asp Ser Leu Pro
305                 310                 315                 320

Val His Ile Ala Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Ser
                340                 345                 350

Cys Arg Glu Cys Arg Gly Gly Val Leu Val Lys Ile Thr Glu Met Cys
                355                 360                 365

Pro Pro Leu Asn Cys Ser Glu Lys Asp His Ile Leu Pro Glu Asn Gln
                370                 375                 380

Cys Cys Arg Val Cys Arg Gly His Asn Phe Cys Ala Glu Gly Pro Lys
385                 390                 395                 400

Cys Gly Glu Asn Ser Glu Cys Lys Asn Trp Asn Thr Lys Ala Thr Cys
                405                 410                 415

Glu Cys Lys Ser Gly Tyr Ile Ser Val Gln Gly Asp Ser Ala Tyr Cys
                420                 425                 430

Glu Asp Ile Asp Glu Cys Ala Ala Lys Met His Tyr Cys His Ala Asn
                435                 440                 445

Thr Val Cys Val Asn Leu Pro Gly Leu Tyr Arg Cys Asp Cys Val Pro
450                 455                 460

Gly Tyr Ile Arg Val Asp Asp Phe Ser Cys Thr Glu His Asp Glu Cys
465                 470                 475                 480
```

```
Gly Ser Gly Gln His Asn Cys Asp Glu Asn Ala Ile Cys Thr Asn Thr
                485                 490                 495

Val Gln Gly His Ser Cys Thr Cys Lys Pro Gly Tyr Val Gly Asn Gly
            500                 505                 510

Thr Ile Cys Arg Ala Phe Cys Glu Glu Gly Cys Arg Tyr Gly Gly Thr
            515                 520                 525

Cys Val Ala Pro Asn Lys Cys Val Cys Pro Ser Gly Phe Thr Gly Ser
            530                 535                 540

His Cys Glu Lys Asp Ile Asp Glu Cys Ser Glu Gly Ile Ile Glu Cys
545                 550                 555                 560

His Asn His Ser Arg Cys Val Asn Leu Pro Gly Trp Tyr His Cys Glu
                565                 570                 575

Cys Arg Ser Gly Phe His Asp Asp Gly Thr Tyr Ser Leu Ser Gly Glu
                580                 585                 590

Ser Cys Ile Asp Ile Asp Glu Cys Ala Leu Arg Thr His Thr Cys Trp
                595                 600                 605

Asn Asp Ser Ala Cys Ile Asn Leu Ala Gly Gly Phe Asp Cys Leu Cys
    610                 615                 620

Pro Ser Gly Pro Ser Cys Ser Gly Asp Cys Pro His Glu Gly Gly Leu
625                 630                 635                 640

Lys His Asn Gly Gln Val Trp Thr Leu Lys Glu Asp Arg Cys Ser Val
                645                 650                 655

Cys Ser Cys Lys Asp Gly Lys Ile Phe Cys Arg Arg Thr Ala Cys Asp
                660                 665                 670

Cys Gln Asn Pro Ser Ala Asp Leu Phe Cys Cys Pro Glu Cys Asp Thr
                675                 680                 685

Arg Val Thr Ser Gln Cys Leu Asp Gln Asn Gly His Lys Leu Tyr Arg
            690                 695                 700

Ser Gly Asp Asn Trp Thr His Ser Cys Gln Gln Cys Arg Cys Leu Glu
705                 710                 715                 720

Gly Glu Val Asp Cys Trp Pro Leu Thr Cys Pro Asn Leu Ser Cys Glu
                725                 730                 735

Tyr Thr Ala Ile Leu Glu Gly Glu Cys Cys Pro Arg Cys Val Ser Asp
                740                 745                 750

Pro Cys Leu Ala Asp Asn Ile Thr Tyr Asp Ile Arg Lys Thr Cys Leu
            755                 760                 765

Asp Ser Tyr Gly Val Ser Arg Leu Ser Gly Ser Val Trp Thr Met Ala
            770                 775                 780

Gly Ser Pro Cys Thr Thr Cys Lys Cys Lys Asn Gly Arg Val Cys Cys
785                 790                 795                 800

Ser Val Asp Phe Glu Cys Leu Gln Asn Asn
                805                 810

<210> SEQ ID NO 3
<211> LENGTH: 2433
<212> TYPE: DNA
<213> ORGANISM: Rattus norvegicus
<220> FEATURE:
<221> NAME/KEY: CDS
<222> LOCATION: (1)..(2433)

<400> SEQUENCE: 3 atg ccg atg gat gtg att tta gtt ttg tgg ttc tgt gta tgc acc gcc      48
Met Pro Met Asp Val Ile Leu Val Leu Trp Phe Cys Val Cys Thr Ala
1               5                   10                  15
```

|     |     |
| --- | --- |
| agg aca gtg ttg ggc ttt ggg atg gac cct gac ctt cag ctg gac atc<br>Arg Thr Val Leu Gly Phe Gly Met Asp Pro Asp Leu Gln Leu Asp Ile<br>20              25              30 | 96 |
| atc tca gag ctc gac ctg gtg aac acc acc ctg gga gtc acg cag gtg<br>Ile Ser Glu Leu Asp Leu Val Asn Thr Thr Leu Gly Val Thr Gln Val<br>35              40              45 | 144 |
| gct gga ctg cac aac gcc agt aaa gca ttt cta ttt caa gat gta cag<br>Ala Gly Leu His Asn Ala Ser Lys Ala Phe Leu Phe Gln Asp Val Gln<br>50              55              60 | 192 |
| aga gag atc cat tcg gcc cct cac gtg agt gag aag ctg atc cag cta<br>Arg Glu Ile His Ser Ala Pro His Val Ser Glu Lys Leu Ile Gln Leu<br>65              70              75              80 | 240 |
| ttc cgg aat aag agc gag ttc acc ttt ttg gct aca gtg cag cag aaa<br>Phe Arg Asn Lys Ser Glu Phe Thr Phe Leu Ala Thr Val Gln Gln Lys<br>85              90              95 | 288 |
| cca tcc acc tca ggg gtg ata ctg tcc atc cgg gag ctg gag cac agc<br>Pro Ser Thr Ser Gly Val Ile Leu Ser Ile Arg Glu Leu Glu His Ser<br>100              105              110 | 336 |
| tat ttt gaa ctg gag agc agt ggc cca aga gaa gag ata cgc tac cat<br>Tyr Phe Glu Leu Glu Ser Ser Gly Pro Arg Glu Glu Ile Arg Tyr His<br>115              120              125 | 384 |
| tac ata cat ggt gga aag ccc agg act gag gcc ctt ccc tac cgc atg<br>Tyr Ile His Gly Gly Lys Pro Arg Thr Glu Ala Leu Pro Tyr Arg Met<br>130              135              140 | 432 |
| gca gac gga caa tgg cac aag gtc gcg ctg tca gtg agc gcc tct cac<br>Ala Asp Gly Gln Trp His Lys Val Ala Leu Ser Val Ser Ala Ser His<br>145              150              155              160 | 480 |
| ctc ctg ctc cac atc gac tgc aat agg att tac gag cgt gtg ata gac<br>Leu Leu Leu His Ile Asp Cys Asn Arg Ile Tyr Glu Arg Val Ile Asp<br>165              170              175 | 528 |
| cct ccg gag acc aac ctt cct cca gga agc aat ctg tgg ctt ggg caa<br>Pro Pro Glu Thr Asn Leu Pro Pro Gly Ser Asn Leu Trp Leu Gly Gln<br>180              185              190 | 576 |
| cgt aac caa aag cat ggc ttt ttc aaa gga atc atc caa gat ggt aag<br>Arg Asn Gln Lys His Gly Phe Phe Lys Gly Ile Ile Gln Asp Gly Lys<br>195              200              205 | 624 |
| atc atc ttc atg ccg aat ggt ttc atc aca cag tgt ccc aac ctc aat<br>Ile Ile Phe Met Pro Asn Gly Phe Ile Thr Gln Cys Pro Asn Leu Asn<br>210              215              220 | 672 |
| cgc act tgc cca aca tgc agt gac ttc ctg agc ctg gtt caa gga ata<br>Arg Thr Cys Pro Thr Cys Ser Asp Phe Leu Ser Leu Val Gln Gly Ile<br>225              230              235              240 | 720 |
| atg gat ttg caa gag ctt ttg gcc aag atg act gca aaa ctg aat tat<br>Met Asp Leu Gln Glu Leu Leu Ala Lys Met Thr Ala Lys Leu Asn Tyr<br>245              250              255 | 768 |
| gca gag acg aga ctt ggt caa ctg gaa aat tgc cac tgt gag aag acc<br>Ala Glu Thr Arg Leu Gly Gln Leu Glu Asn Cys His Cys Glu Lys Thr<br>260              265              270 | 816 |
| tgc caa gtg agt ggg ctc ctc tac agg gac caa gac tcc tgg gtg gat<br>Cys Gln Val Ser Gly Leu Leu Tyr Arg Asp Gln Asp Ser Trp Val Asp<br>275              280              285 | 864 |
| ggt gac aac tgt ggg aac tgc acg tgc aaa agt ggt gcc gtg gag tgc<br>Gly Asp Asn Cys Gly Asn Cys Thr Cys Lys Ser Gly Ala Val Glu Cys<br>290              295              300 | 912 |
| cgc agg atg tcc tgt ccc ccg ctc aac tgt tcc ccg gac tca ctt cct<br>Arg Arg Met Ser Cys Pro Pro Leu Asn Cys Ser Pro Asp Ser Leu Pro<br>305              310              315              320 | 960 |
| gtg cac att tcc ggc cag tgt tgt aaa gtt tgc aga cca aaa tgt atc<br>Val His Ile Ser Gly Gln Cys Cys Lys Val Cys Arg Pro Lys Cys Ile<br>325              330              335 | 1008 |

-continued

| | |
|---|---|
| tat gga gga aaa gtt ctt gct gag ggc cag cgg att tta acc aag acc<br>Tyr Gly Gly Lys Val Leu Ala Glu Gly Gln Arg Ile Leu Thr Lys Thr<br>340     345     350 | 1056 |
| tgc cgg gaa tgt cga ggt gga gtc ttg gta aaa atc aca gaa gct tgc<br>Cys Arg Glu Cys Arg Gly Gly Val Leu Val Lys Ile Thr Glu Ala Cys<br>355     360     365 | 1104 |
| cct cct ttg aac tgc tca gca aag gat cat att ctt cca gag aat cag<br>Pro Pro Leu Asn Cys Ser Ala Lys Asp His Ile Leu Pro Glu Asn Gln<br>370     375     380 | 1152 |
| tgc tgc agg gtc tgc cca ggt cat aac ttc tgt gca gaa gca cct aag<br>Cys Cys Arg Val Cys Pro Gly His Asn Phe Cys Ala Glu Ala Pro Lys<br>385     390     395     400 | 1200 |
| tgc gga gaa aac tcg gaa tgc aaa aat tgg aat aca aaa gca acc tgt<br>Cys Gly Glu Asn Ser Glu Cys Lys Asn Trp Asn Thr Lys Ala Thr Cys<br>     405     410     415 | 1248 |
| gag tgc aag aat gga tac atc tct gtc cag ggc aac tct gca tac tgt<br>Glu Cys Lys Asn Gly Tyr Ile Ser Val Gln Gly Asn Ser Ala Tyr Cys<br>     420     425     430 | 1296 |
| gaa gat att gat gag tgt gca gct aaa atg cac tat tgt cat gcc aac<br>Glu Asp Ile Asp Glu Cys Ala Ala Lys Met His Tyr Cys His Ala Asn<br>435     440     445 | 1344 |
| acc gtg tgt gtc aac ttg ccg ggg ttg tat cgc tgt gac tgc gtc cca<br>Thr Val Cys Val Asn Leu Pro Gly Leu Tyr Arg Cys Asp Cys Val Pro<br>450     455     460 | 1392 |
| ggg tac atc cgt gtg gat gac ttc tct tgt acg gag cat gat gat tgt<br>Gly Tyr Ile Arg Val Asp Asp Phe Ser Cys Thr Glu His Asp Asp Cys<br>465     470     475     480 | 1440 |
| ggc agc gga caa cac aac tgc gac aaa aat gcc atc tgt acc aac aca<br>Gly Ser Gly Gln His Asn Cys Asp Lys Asn Ala Ile Cys Thr Asn Thr<br>     485     490     495 | 1488 |
| gtc cag gga cac agc tgc acc tgc cag ccg ggt tac gtg gga aat ggc<br>Val Gln Gly His Ser Cys Thr Cys Gln Pro Gly Tyr Val Gly Asn Gly<br>500     505     510 | 1536 |
| acc atc tgc aaa gca ttc tgt gaa gag ggt tgc aga tac gga ggt acc<br>Thr Ile Cys Lys Ala Phe Cys Glu Glu Gly Cys Arg Tyr Gly Gly Thr<br>515     520     525 | 1584 |
| tgt gtg gct cct aac aag tgt gtc tgt cct tct gga ttc acg gga agc<br>Cys Val Ala Pro Asn Lys Cys Val Cys Pro Ser Gly Phe Thr Gly Ser<br>530     535     540 | 1632 |
| cac tgt gag aaa gat att gat gaa tgc gca gag gga ttc gtt gaa tgc<br>His Cys Glu Lys Asp Ile Asp Glu Cys Ala Glu Gly Phe Val Glu Cys<br>545     550     555     560 | 1680 |
| cac aac tac tcc cgc tgt gtt aac ctg cca ggg tgg tac cac tgt gag<br>His Asn Tyr Ser Arg Cys Val Asn Leu Pro Gly Trp Tyr His Cys Glu<br>     565     570     575 | 1728 |
| tgc aga agc ggt ttc cat gac gat ggg acc tac tca ctg tcc ggg gag<br>Cys Arg Ser Gly Phe His Asp Asp Gly Thr Tyr Ser Leu Ser Gly Glu<br>     580     585     590 | 1776 |
| tcc tgc att gat atc gat gaa tgt gcc tta aga act cac act tgt tgg<br>Ser Cys Ile Asp Ile Asp Glu Cys Ala Leu Arg Thr His Thr Cys Trp<br>595     600     605 | 1824 |
| aat gac tct gcc tgc atc aac tta gca gga gga ttt gac tgc ctg tgt<br>Asn Asp Ser Ala Cys Ile Asn Leu Ala Gly Gly Phe Asp Cys Leu Cys<br>610     615     620 | 1872 |
| ccc tct ggg ccc tcc tgc tct ggt gac tgt ccc cac gaa gga ggg ctg<br>Pro Ser Gly Pro Ser Cys Ser Gly Asp Cys Pro His Glu Gly Gly Leu<br>625     630     635     640 | 1920 |
| aag cat aat ggg cag gtg tgg att ctg aga gaa gac agg tgt tca gtc<br>Lys His Asn Gly Gln Val Trp Ile Leu Arg Glu Asp Arg Cys Ser Val | 1968 |

-continued

```
                   645                 650                 655
tgt tcc tgc aag gat ggg aag ata ttc tgc cgg cgg aca gct tgt gat    2016
Cys Ser Cys Lys Asp Gly Lys Ile Phe Cys Arg Arg Thr Ala Cys Asp
            660                 665                 670 tgc cag aat cca aat gtt gac ctt ttt tgc tgc cca gag tgc gat acc    2064
Cys Gln Asn Pro Asn Val Asp Leu Phe Cys Cys Pro Glu Cys Asp Thr
        675                 680                 685 agg gtc acc agc caa tgt tta gat caa agt gga cag aag ctc tat cga    2112
Arg Val Thr Ser Gln Cys Leu Asp Gln Ser Gly Gln Lys Leu Tyr Arg
    690                 695                 700 agt gga gac aac tgg acc cac agc tgc cag cag tgc cga tgt ctg gaa    2160
Ser Gly Asp Asn Trp Thr His Ser Cys Gln Gln Cys Arg Cys Leu Glu
705                 710                 715                 720 gga gag gca gac tgc tgg cct ctg gct tgc cct agt ttg ggc tgt gaa    2208
Gly Glu Ala Asp Cys Trp Pro Leu Ala Cys Pro Ser Leu Gly Cys Glu
                725                 730                 735 tac aca gcc atg ttt gaa ggg gag tgt tgt ccc cga tgt gtc agt gac    2256
Tyr Thr Ala Met Phe Glu Gly Glu Cys Cys Pro Arg Cys Val Ser Asp
            740                 745                 750 ccc tgc ctg gct ggt aat att gcc tat gac atc aga aaa act tgc ctg    2304
Pro Cys Leu Ala Gly Asn Ile Ala Tyr Asp Ile Arg Lys Thr Cys Leu
        755                 760                 765 gac agc ttt ggt gtt tcg agg ctg agc gga gcc gtg tgg aca atg gct    2352
Asp Ser Phe Gly Val Ser Arg Leu Ser Gly Ala Val Trp Thr Met Ala
    770                 775                 780 gga tct cct tgt aca acc tgc aaa tgc aag aat ggg aga gtc tgc tgc    2400
Gly Ser Pro Cys Thr Thr Cys Lys Cys Lys Asn Gly Arg Val Cys Cys
785                 790                 795                 800 tct gtg gat ctg gag tgt att gag aat aac tga                        2433
Ser Val Asp Leu Glu Cys Ile Glu Asn Asn
                805                 810

<210> SEQ ID NO 4
<211> LENGTH: 810
<212> TYPE: PRT
<213> ORGANISM: Rattus norvegicus

<400> SEQUENCE: 4

Met Pro Met Asp Val Ile Leu Val Leu Trp Phe Cys Val Cys Thr Ala
1               5                   10                  15

Arg Thr Val Leu Gly Phe Gly Met Asp Pro Asp Leu Gln Leu Asp Ile
            20                  25                  30

Ile Ser Glu Leu Asp Leu Val Asn Thr Thr Leu Gly Val Thr Gln Val
        35                  40                  45

Ala Gly Leu His Asn Ala Ser Lys Ala Phe Leu Phe Gln Asp Val Gln
    50                  55                  60

Arg Glu Ile His Ser Ala Pro His Val Ser Glu Lys Leu Ile Gln Leu
65                  70                  75                  80

Phe Arg Asn Lys Ser Glu Phe Thr Phe Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Pro Arg Glu Glu Ile Arg Tyr His
        115                 120                 125

Tyr Ile His Gly Gly Lys Pro Arg Thr Glu Ala Leu Pro Tyr Arg Met
    130                 135                 140

Ala Asp Gly Gln Trp His Lys Val Ala Leu Ser Val Ser Ala Ser His
145                 150                 155                 160
```

-continued

```
Leu Leu Leu His Ile Asp Cys Asn Arg Ile Tyr Glu Arg Val Ile Asp
            165                 170                 175
Pro Pro Glu Thr Asn Leu Pro Pro Gly Ser Asn Leu Trp Leu Gly Gln
        180                 185                 190
Arg Asn Gln Lys His Gly Phe Phe Lys Gly Ile Ile Gln Asp Gly Lys
    195                 200                 205
Ile Ile Phe Met Pro Asn Gly Phe Ile Thr Gln Cys Pro Asn Leu Asn
210                 215                 220
Arg Thr Cys Pro Thr Cys Ser Asp Phe Leu Ser Leu Val Gln Gly Ile
225                 230                 235                 240
Met Asp Leu Gln Glu Leu Leu Ala Lys Met Thr Ala Lys Leu Asn Tyr
            245                 250                 255
Ala Glu Thr Arg Leu Gly Gln Leu Glu Asn Cys His Cys Glu Lys Thr
        260                 265                 270
Cys Gln Val Ser Gly Leu Leu Tyr Arg Asp Gln Asp Ser Trp Val Asp
    275                 280                 285
Gly Asp Asn Cys Gly Asn Cys Thr Cys Lys Ser Gly Ala Val Glu Cys
290                 295                 300
Arg Arg Met Ser Cys Pro Pro Leu Asn Cys Ser Pro Asp Ser Leu Pro
305                 310                 315                 320
Val His Ile Ser Gly Gln Cys Cys Lys Val Cys Arg Pro Lys Cys Ile
            325                 330                 335
Tyr Gly Gly Lys Val Leu Ala Glu Gly Gln Arg Ile Leu Thr Lys Thr
        340                 345                 350
Cys Arg Glu Cys Arg Gly Gly Val Leu Val Lys Ile Thr Glu Ala Cys
    355                 360                 365
Pro Pro Leu Asn Cys Ser Ala Lys Asp His Ile Leu Pro Glu Asn Gln
        370                 375                 380
Cys Cys Arg Val Cys Pro Gly His Asn Phe Cys Ala Glu Ala Pro Lys
385                 390                 395                 400
Cys Gly Glu Asn Ser Glu Cys Lys Asn Trp Asn Thr Lys Ala Thr Cys
            405                 410                 415
Glu Cys Lys Asn Gly Tyr Ile Ser Val Gln Gly Asn Ser Ala Tyr Cys
        420                 425                 430
Glu Asp Ile Asp Glu Cys Ala Ala Lys Met His Tyr Cys His Ala Asn
    435                 440                 445
Thr Val Cys Val Asn Leu Pro Gly Leu Tyr Arg Cys Asp Cys Val Pro
    450                 455                 460
Gly Tyr Ile Arg Val Asp Asp Phe Ser Cys Thr Glu His Asp Asp Cys
465                 470                 475                 480
Gly Ser Gly Gln His Asn Cys Asp Lys Asn Ala Ile Cys Thr Asn Thr
            485                 490                 495
Val Gln Gly His Ser Cys Thr Cys Gln Pro Gly Tyr Val Gly Asn Gly
        500                 505                 510
Thr Ile Cys Lys Ala Phe Cys Glu Glu Gly Cys Arg Tyr Gly Gly Thr
    515                 520                 525
Cys Val Ala Pro Asn Lys Cys Val Cys Pro Ser Gly Phe Thr Gly Ser
    530                 535                 540
His Cys Glu Lys Asp Ile Asp Glu Cys Ala Glu Gly Phe Val Glu Cys
545                 550                 555                 560
His Asn Tyr Ser Arg Cys Val Asn Leu Pro Gly Trp Tyr His Cys Glu
            565                 570                 575
```

```
Cys Arg Ser Gly Phe His Asp Asp Gly Thr Tyr Ser Leu Ser Gly Glu
            580                 585                 590

Ser Cys Ile Asp Ile Asp Glu Cys Ala Leu Arg Thr His Thr Cys Trp
        595                 600                 605

Asn Asp Ser Ala Cys Ile Asn Leu Ala Gly Gly Phe Asp Cys Leu Cys
            610                 615                 620

Pro Ser Gly Pro Ser Cys Ser Gly Asp Cys Pro His Glu Gly Leu
625                 630                 635                 640

Lys His Asn Gly Gln Val Trp Ile Leu Arg Glu Asp Arg Cys Ser Val
                645                 650                 655

Cys Ser Cys Lys Asp Gly Lys Ile Phe Cys Arg Arg Thr Ala Cys Asp
            660                 665                 670

Cys Gln Asn Pro Asn Val Asp Leu Phe Cys Cys Pro Glu Cys Asp Thr
            675                 680                 685

Arg Val Thr Ser Gln Cys Leu Asp Gln Ser Gly Gln Lys Leu Tyr Arg
            690                 695                 700

Ser Gly Asp Asn Trp Thr His Ser Cys Gln Gln Cys Arg Cys Leu Glu
705                 710                 715                 720

Gly Glu Ala Asp Cys Trp Pro Leu Ala Cys Pro Ser Leu Gly Cys Glu
                725                 730                 735

Tyr Thr Ala Met Phe Glu Gly Glu Cys Cys Pro Arg Cys Val Ser Asp
            740                 745                 750

Pro Cys Leu Ala Gly Asn Ile Ala Tyr Asp Ile Arg Lys Thr Cys Leu
        755                 760                 765

Asp Ser Phe Gly Val Ser Arg Leu Ser Gly Ala Val Trp Thr Met Ala
        770                 775                 780

Gly Ser Pro Cys Thr Thr Cys Lys Cys Lys Asn Gly Arg Val Cys Cys
785                 790                 795                 800

Ser Val Asp Leu Glu Cys Ile Glu Asn Asn
            805                 810

<210> SEQ ID NO 5
<211> LENGTH: 2433
<212> TYPE: DNA
<213> ORGANISM: Mus musculus

<400> SEQUENCE: 5
atgccgatgg atgtgatttt agttttgtgg ttctgtgtgt gcaccgccag acagtgctg      60 ggctttggga tggaccctga ccttcagatg acatcatca ctgaacttga ccttgtgaac     120
accaccctgg gcgtcactca ggtggctgga ctacacaatg ccagtaaggc atttctgttt     180
caagatgtac agagagagat ccactcagcc cctcatgtga gtgagaagct gatccagcta     240
ttccggaata gagtgagtt tacctttttg gctacagtgc agcagaagcc gtccacctca     300
ggggtgatac tgtcgatccg ggagctggaa cacagctatt tgaactgga gagcagtggc     360 ccaagagaag agatacgcta tcattacatc catggcggca agcccaggac tgaggccctt     420
ccctaccgca tggccgatgg acagtggcac aaggtcgcgc tgtctgtgag cgcctctcac     480
ctcctactcc atgtcgactg caataggatt tatgagcgtg tgatagatcc tccggagacc     540
aaccttcctc caggaagcaa tctatggctt gggcaacgta tcaaaagca tggcttttc      600 aaaggaatca tccaagatgg caagatcatc ttcatgccga acggcttcat cacacagtgc     660
cccaacctaa atcgcacttg cccaacatgc agtgatttcc tgagcctggt tcaaggaata     720
atggatttgc aagagctttt ggccaagatg actgcaaaac tgaattatgc agagacgaga     780
```

-continued

| | |
|---|---|
| cttggtcaac tggaaaattg ccactgtgag aagacctgcc aagtgagtgg gctgctctac | 840 |
| agggaccaag actcctgggt agatggtgac aactgcagga actgcacatg caaaagtggt | 900 |
| gctgtggagt gccgaaggat gtcctgtccc ccactcaact gttccccaga ctcacttcct | 960 |
| gtgcatattt ctggccaatg ttgtaaagtt tgcagaccaa atgtatcta tggaggaaaa | 1020 |
| gttcttgctg agggccagcg gattttaacc aagacctgcc gggaatgtcg aggtggagtc | 1080 |
| ttggtaaaaa tcacagaagc ttgccctcct ttgaactgct cagagaagga tcatattctt | 1140 |
| ccggagaacc agtgctgcag ggtctgccga ggtcataact tctgtgcaga agcacctaag | 1200 |
| tgtggagaaa ctcggaatg caaaaattgg aatacaaaag cgacttgtga gtgcaagaat | 1260 |
| ggatacatct ctgtccaggg caactctgca tactgtgaag atatcgatga gtgtgcagca | 1320 |
| aagatgcact actgtcatgc caacacggtg tgtgtcaact tgccggggtt atatcgctgt | 1380 |
| gactgcatcc aggatacat ccgtgtggat gacttctctt gtacggagca tgatgattgt | 1440 |
| ggcagcggac aacacaactg tgacaaaaat gccatctgta ccaacacagt ccagggacac | 1500 |
| agctgtacct gccagccagg ctacgtggga atggtactg tctgcaaagc attctgtgaa | 1560 |
| gagggttgca gatacggagg tacctgtgtg gcccctaaca atgtgtctg tccttctgga | 1620 |
| ttcacaggaa gccactgtga gaaagatatt gatgaatgtg cagagggatt cgttgagtgc | 1680 |
| cacaaccact cccgctgcgt taaccttcca gggtggtacc actgtgagtg cagaagcggt | 1740 |
| ttccatgacg atgggaccta ttcactgtcc ggggagtcct gcattgatat tgatgaatgt | 1800 |
| gccttaagaa ctcacacttg ttggaatgac tctgcctgca tcaacttagc aggaggatt | 1860 |
| gactgcctgt gtccctctgg gccctcctgc tctggtgact gtccccacga aggggggctg | 1920 |
| aagcataatg gcaggtgtg gattctgaga gaagacaggt gttcagtctg ttcctgtaag | 1980 |
| gatgggaaga tattctgccg gcggacagct tgtgattgcc agaatccaaa tgttgacctt | 2040 |
| ttctgctgcc cagagtgtga caccagggtc actagccaat gtttagatca aagcggacag | 2100 |
| aagctctatc gaagtggaga caactggacc cacagctgcc agcagtgccg atgtctggaa | 2160 |
| ggagaggcag actgctggcc tctagcttgc cctagtttga gctgtgaata cacagccatc | 2220 |
| tttgaaggag agtgttgtcc ccgctgtgtc agtgacccct gcctggctga taatattgcc | 2280 |
| tatgacatca gaaaaacttg cctggacagc tctggtattt cgaggctgag cggcgcagtg | 2340 |
| tggacaatgg ctggatctcc ctgtacaacc tgtcaatgca gaatgggag agtctgctgc | 2400 |
| tctgtggatc tggtgtgtct tgagaataac tga | 2433 |

<210> SEQ ID NO 6
<211> LENGTH: 810
<212> TYPE: PRT
<213> ORGANISM: Mus musculus

<400> SEQUENCE: 6

Met Pro Met Asp Val Ile Leu Val Leu Trp Phe Cys Val Cys Thr Ala
1               5                   10                  15

Arg Thr Val Leu Gly Phe Gly Met Asp Pro Asp Leu Gln Met Asp Ile
            20                  25                  30

Ile Thr Glu Leu Asp Leu Val Asn Thr Thr Leu Gly Val Thr Gln Val
        35                  40                  45

Ala Gly Leu His Asn Ala Ser Lys Ala Phe Leu Phe Gln Asp Val Gln
    50                  55                  60

Arg Glu Ile His Ser Ala Pro His Val Ser Glu Lys Leu Ile Gln Leu
65                  70                  75                  80

-continued

```
Phe Arg Asn Lys Ser Glu Phe Thr Phe Leu Ala Thr Val Gln Gln Lys
                 85                  90                  95
Pro Ser Thr Ser Gly Val Ile Leu Ser Ile Arg Glu Leu Glu His Ser
            100                 105                 110
Tyr Phe Glu Leu Glu Ser Ser Gly Pro Arg Glu Ile Arg Tyr His
        115                 120                 125
Tyr Ile His Gly Gly Lys Pro Arg Thr Glu Ala Leu Pro Tyr Arg Met
    130                 135                 140
Ala Asp Gly Gln Trp His Lys Val Ala Leu Ser Val Ser Ala Ser His
145                 150                 155                 160
Leu Leu Leu His Val Asp Cys Asn Arg Ile Tyr Glu Arg Val Ile Asp
                165                 170                 175
Pro Pro Glu Thr Asn Leu Pro Pro Gly Ser Asn Leu Trp Leu Gly Gln
            180                 185                 190
Arg Asn Gln Lys His Gly Phe Phe Lys Gly Ile Ile Gln Asp Gly Lys
        195                 200                 205
Ile Ile Phe Met Pro Asn Gly Phe Ile Thr Gln Cys Pro Asn Leu Asn
    210                 215                 220
Arg Thr Cys Pro Thr Cys Ser Asp Phe Leu Ser Leu Val Gln Gly Ile
225                 230                 235                 240
Met Asp Leu Gln Glu Leu Leu Ala Lys Met Thr Ala Lys Leu Asn Tyr
                245                 250                 255
Ala Glu Thr Arg Leu Gly Gln Leu Glu Asn Cys His Cys Glu Lys Thr
            260                 265                 270
Cys Gln Val Ser Gly Leu Leu Tyr Arg Asp Gln Asp Ser Trp Val Asp
        275                 280                 285
Gly Asp Asn Cys Arg Asn Cys Thr Cys Lys Ser Gly Ala Val Glu Cys
    290                 295                 300
Arg Arg Met Ser Cys Pro Pro Leu Asn Cys Ser Pro Asp Ser Leu Pro
305                 310                 315                 320
Val His Ile Ser Gly Gln Cys Cys Lys Val Cys Arg Pro Lys Cys Ile
                325                 330                 335
Tyr Gly Gly Lys Val Leu Ala Glu Gly Gln Arg Ile Leu Thr Lys Thr
            340                 345                 350
Cys Arg Glu Cys Arg Gly Gly Val Leu Val Lys Ile Thr Glu Ala Cys
        355                 360                 365
Pro Pro Leu Asn Cys Ser Glu Lys Asp His Ile Leu Pro Glu Asn Gln
    370                 375                 380
Cys Cys Arg Val Cys Arg Gly His Asn Phe Cys Ala Glu Ala Pro Lys
385                 390                 395                 400
Cys Gly Glu Asn Ser Glu Cys Lys Asn Trp Asn Thr Lys Ala Thr Cys
                405                 410                 415
Glu Cys Lys Asn Gly Tyr Ile Ser Val Gln Gly Asn Ser Ala Tyr Cys
            420                 425                 430
Glu Asp Ile Asp Glu Cys Ala Ala Lys Met His Tyr Cys His Ala Asn
        435                 440                 445
Thr Val Cys Val Asn Leu Pro Gly Leu Tyr Arg Cys Asp Cys Ile Pro
    450                 455                 460
Gly Tyr Ile Arg Val Asp Asp Phe Ser Cys Thr Glu His Asp Cys
465                 470                 475                 480
Gly Ser Gly Gln His Asn Cys Asp Lys Asn Ala Ile Cys Thr Asn Thr
                485                 490                 495
Val Gln Gly His Ser Cys Thr Cys Gln Pro Gly Tyr Val Gly Asn Gly
```

-continued

```
                        500                 505                 510
Thr Val Cys Lys Ala Phe Cys Glu Glu Gly Cys Arg Tyr Gly Gly Thr
            515                 520                 525

Cys Val Ala Pro Asn Lys Cys Val Cys Pro Ser Gly Phe Thr Gly Ser
        530                 535                 540

His Cys Glu Lys Asp Ile Asp Glu Cys Ala Glu Gly Phe Val Glu Cys
545                 550                 555                 560

His Asn His Ser Arg Cys Val Asn Leu Pro Gly Trp Tyr His Cys Glu
                565                 570                 575

Cys Arg Ser Gly Phe His Asp Asp Gly Thr Tyr Ser Leu Ser Gly Glu
            580                 585                 590

Ser Cys Ile Asp Ile Asp Glu Cys Ala Leu Arg Thr His Thr Cys Trp
        595                 600                 605

Asn Asp Ser Ala Cys Ile Asn Leu Ala Gly Gly Phe Asp Cys Leu Cys
610                 615                 620

Pro Ser Gly Pro Ser Cys Ser Gly Asp Cys Pro His Glu Gly Gly Leu
625                 630                 635                 640

Lys His Asn Gly Gln Val Trp Ile Leu Arg Glu Asp Arg Cys Ser Val
                645                 650                 655

Cys Ser Cys Lys Asp Gly Lys Ile Phe Cys Arg Arg Thr Ala Cys Asp
            660                 665                 670

Cys Gln Asn Pro Asn Val Asp Leu Phe Cys Cys Pro Glu Cys Asp Thr
        675                 680                 685

Arg Val Thr Ser Gln Cys Leu Asp Gln Ser Gly Gln Lys Leu Tyr Arg
690                 695                 700

Ser Gly Asp Asn Trp Thr His Ser Cys Gln Gln Cys Arg Cys Leu Glu
705                 710                 715                 720

Gly Glu Ala Asp Cys Trp Pro Leu Ala Cys Pro Ser Leu Ser Cys Glu
                725                 730                 735

Tyr Thr Ala Ile Phe Glu Gly Glu Cys Cys Pro Arg Cys Val Ser Asp
            740                 745                 750

Pro Cys Leu Ala Asp Asn Ile Ala Tyr Asp Ile Arg Lys Thr Cys Leu
        755                 760                 765

Asp Ser Ser Gly Ile Ser Arg Leu Ser Gly Ala Val Trp Thr Met Ala
770                 775                 780

Gly Ser Pro Cys Thr Thr Cys Gln Cys Lys Asn Gly Arg Val Cys Cys
785                 790                 795                 800

Ser Val Asp Leu Val Cys Leu Glu Asn Asn
                805                 810
```

<210> SEQ ID NO 7
<211> LENGTH: 2451
<212> TYPE: DNA
<213> ORGANISM: Homo sapiens
<220> FEATURE:
<221> NAME/KEY: CDS
<222> LOCATION: (1)..(2451)

<400> SEQUENCE: 7

```
atg gag tct cgg gtc tta ctg aga aca ttc tgt ttg atc ttc ggt ctc        48
Met Glu Ser Arg Val Leu Leu Arg Thr Phe Cys Leu Ile Phe Gly Leu
1               5                   10                  15 gga gca gtt tgg ggg ctt ggt gtg gac cct tcc cta cag att gac gtc        96
Gly Ala Val Trp Gly Leu Gly Val Asp Pro Ser Leu Gln Ile Asp Val
            20                  25                  30 tta aca gag tta gaa ctt ggg gag tcc acg acc gga gtg cgt cag gtc       144
Leu Thr Glu Leu Glu Leu Gly Glu Ser Thr Thr Gly Val Arg Gln Val
```

```
                Leu Thr Glu Leu Glu Leu Gly Glu Ser Thr Thr Gly Val Arg Gln Val
                        35                  40                  45 ccg ggg ctg cat aat ggg acg aaa gcc ttt ctc ttt caa gat act ccc          192
Pro Gly Leu His Asn Gly Thr Lys Ala Phe Leu Phe Gln Asp Thr Pro
 50                  55                  60 aga agc ata aaa gca tcc act gct aca gct gaa cag ttt ttt cag aag          240
Arg Ser Ile Lys Ala Ser Thr Ala Thr Ala Glu Gln Phe Phe Gln Lys
 65                  70                  75                  80 ctg aga aat aaa cat gaa ttt act att ttg gtg acc cta aaa cag acc          288
Leu Arg Asn Lys His Glu Phe Thr Ile Leu Val Thr Leu Lys Gln Thr
                 85                  90                  95 cac tta aat tca gga gtt att ctc tca att cac cac ttg gat cac agg          336
His Leu Asn Ser Gly Val Ile Leu Ser Ile His His Leu Asp His Arg
            100                 105                 110 tac ctg gaa ctg gaa agt agt ggc cat cgg aat gaa gtc aga ctg cat          384
Tyr Leu Glu Leu Glu Ser Ser Gly His Arg Asn Glu Val Arg Leu His
            115                 120                 125 tac cgc tca ggc agt cac cgc cct cac aca gaa gtg ttt cct tac att          432
Tyr Arg Ser Gly Ser His Arg Pro His Thr Glu Val Phe Pro Tyr Ile
130                 135                 140 ttg gct gat gac aag tgg cac aag ctc tcc tta gcc atc agt gct tcc          480
Leu Ala Asp Asp Lys Trp His Lys Leu Ser Leu Ala Ile Ser Ala Ser
145                 150                 155                 160 cat ttg att tta cac att gac tgc aat aaa att tat gaa agg gta gta          528
His Leu Ile Leu His Ile Asp Cys Asn Lys Ile Tyr Glu Arg Val Val
                165                 170                 175 gaa aag ccc tcc aca gac ttg cct cta ggc aca aca ttt tgg cta gga          576
Glu Lys Pro Ser Thr Asp Leu Pro Leu Gly Thr Thr Phe Trp Leu Gly
            180                 185                 190 cag aga aat aat gcg cat gga tat ttt aag ggt ata atg caa gat gtc          624
Gln Arg Asn Asn Ala His Gly Tyr Phe Lys Gly Ile Met Gln Asp Val
            195                 200                 205 caa tta ctt gtc atg ccc cag gga ttt att gct cag tgc cca gat ctt          672
Gln Leu Leu Val Met Pro Gln Gly Phe Ile Ala Gln Cys Pro Asp Leu
            210                 215                 220 aat cgc acc tgt cca act tgc aat gac ttc cat gga ctt gtg cag aaa          720
Asn Arg Thr Cys Pro Thr Cys Asn Asp Phe His Gly Leu Val Gln Lys
225                 230                 235                 240 atc atg gag cta cag gat att tta gcc aaa aca tca gcc aag ctg tct          768
Ile Met Glu Leu Gln Asp Ile Leu Ala Lys Thr Ser Ala Lys Leu Ser
                245                 250                 255 cga gct gaa cag cga atg aat aga ttg gat cag tgc tat tgt gaa agg          816
Arg Ala Glu Gln Arg Met Asn Arg Leu Asp Gln Cys Tyr Cys Glu Arg
            260                 265                 270 act tgc acc atg aag gga acc acc tac cga gaa ttt gag tcc tgg ata          864
Thr Cys Thr Met Lys Gly Thr Thr Tyr Arg Glu Phe Glu Ser Trp Ile
            275                 280                 285 gac ggc tgt aag aac tgc aca tgc ctg aat gga acc atc cag tgt gaa          912
Asp Gly Cys Lys Asn Cys Thr Cys Leu Asn Gly Thr Ile Gln Cys Glu
            290                 295                 300 act cta atc tgc cca aat cct gac tgc cca ctt aag tcg gct ctt gcg          960
Thr Leu Ile Cys Pro Asn Pro Asp Cys Pro Leu Lys Ser Ala Leu Ala
305                 310                 315                 320 tat gtg gat ggc aaa tgc tgt aag gaa tgc aaa tcg ata tgc caa ttt         1008
Tyr Val Asp Gly Lys Cys Cys Lys Glu Cys Lys Ser Ile Cys Gln Phe
                325                 330                 335 caa gga cga acc tac ttt gaa gga gaa aga aat aca gtc tat tcc tct         1056
Gln Gly Arg Thr Tyr Phe Glu Gly Glu Arg Asn Thr Val Tyr Ser Ser
            340                 345                 350
```

```
                                                         -continued tct gga gta tgt gtt ctc tat gag tgc aag gac cag acc atg aaa ctt    1104
Ser Gly Val Cys Val Leu Tyr Glu Cys Lys Asp Gln Thr Met Lys Leu
        355                 360                 365 gtt gag agt tca ggc tgt cca gct ttg gat tgt cca gag tct cat cag    1152
Val Glu Ser Ser Gly Cys Pro Ala Leu Asp Cys Pro Glu Ser His Gln
370                 375                 380 ata acc ttg tct cac agc tgt tgc aaa gtt tgt aaa ggt tat gac ttt    1200
Ile Thr Leu Ser His Ser Cys Cys Lys Val Cys Lys Gly Tyr Asp Phe
385                 390                 395                 400 tgt tct gaa agg cat aac tgc atg gag aat tcc atc tgc aga aat ctg    1248
Cys Ser Glu Arg His Asn Cys Met Glu Asn Ser Ile Cys Arg Asn Leu
                405                 410                 415 aat gac agg gct gtt tgt agc tgt cga gat ggt ttt agg gct ctt cga    1296
Asn Asp Arg Ala Val Cys Ser Cys Arg Asp Gly Phe Arg Ala Leu Arg
            420                 425                 430 gag gat aat gcc tac tgt gaa gac atc gat gag tgt gct gaa ggg cgc    1344
Glu Asp Asn Ala Tyr Cys Glu Asp Ile Asp Glu Cys Ala Glu Gly Arg
        435                 440                 445 cat tac tgt cgt gaa aat aca atg tgt gtc aac acc ccg ggt tct ttt    1392
His Tyr Cys Arg Glu Asn Thr Met Cys Val Asn Thr Pro Gly Ser Phe
    450                 455                 460 atg tgc atc tgc aaa act gga tac atc aga att gat gat tat tca tgt    1440
Met Cys Ile Cys Lys Thr Gly Tyr Ile Arg Ile Asp Asp Tyr Ser Cys
465                 470                 475                 480 aca gaa cat gat gag tgt atc aca aat cag cac aac tgt gat gaa aat    1488
Thr Glu His Asp Glu Cys Ile Thr Asn Gln His Asn Cys Asp Glu Asn
                485                 490                 495 gct tta tgc ttc aac act gtt gga gga cac aac tgt gtt tgc aag ccg    1536
Ala Leu Cys Phe Asn Thr Val Gly Gly His Asn Cys Val Cys Lys Pro
            500                 505                 510 ggc tat aca ggg aat gga acg aca tgc aaa gca ttt tgc aaa gat ggc    1584
Gly Tyr Thr Gly Asn Gly Thr Thr Cys Lys Ala Phe Cys Lys Asp Gly
        515                 520                 525 tgt agg aat gga gga gcc tgt att gcc gct aat gtg tgt gcc tgc cca    1632
Cys Arg Asn Gly Gly Ala Cys Ile Ala Ala Asn Val Cys Ala Cys Pro
    530                 535                 540 caa ggc ttc act gga ccc agc tgt gaa acg gac att gat gaa tgc tct    1680
Gln Gly Phe Thr Gly Pro Ser Cys Glu Thr Asp Ile Asp Glu Cys Ser
545                 550                 555                 560 gat ggt ttt gtt caa tgt gac agt cgt gct aat tgc att aac ctg cct    1728
Asp Gly Phe Val Gln Cys Asp Ser Arg Ala Asn Cys Ile Asn Leu Pro
                565                 570                 575 gga tgg tac cac tgt gag tgc aga gat ggc tac cat gac aat ggg atg    1776
Gly Trp Tyr His Cys Glu Cys Arg Asp Gly Tyr His Asp Asn Gly Met
            580                 585                 590 ttt tca cca agt gga gaa tcg tgt gaa gat att gat gag tgt ggg acc    1824
Phe Ser Pro Ser Gly Glu Ser Cys Glu Asp Ile Asp Glu Cys Gly Thr
        595                 600                 605 ggg agg cac agc tgt gcc aat gat acc att tgc ttc aat ttg gat ggc    1872
Gly Arg His Ser Cys Ala Asn Asp Thr Ile Cys Phe Asn Leu Asp Gly
    610                 615                 620 gga tat gat tgt cga tgt cct cat gga aag aat tgc aca ggg gac tgc    1920
Gly Tyr Asp Cys Arg Cys Pro His Gly Lys Asn Cys Thr Gly Asp Cys
625                 630                 635                 640 atc cat gat gga aaa gtt aag cac aat ggt cag att tgg gtg ttg gaa    1968
Ile His Asp Gly Lys Val Lys His Asn Gly Gln Ile Trp Val Leu Glu
                645                 650                 655 aat gac agg tgc tct gtg tgc tca tgt cag aat gga ttc gtt atg tgt    2016
Asn Asp Arg Cys Ser Val Cys Ser Cys Gln Asn Gly Phe Val Met Cys
            660                 665                 670
```

```
cga cgg atg gtc tgt gac tgt gag aat ccc aca gtt gat ctt ttt tgc    2064
Arg Arg Met Val Cys Asp Cys Glu Asn Pro Thr Val Asp Leu Phe Cys
            675                 680                 685 tgc cct gaa tgt gac cca agg ctt agt agt cag tgc ctc cat caa aat    2112
Cys Pro Glu Cys Asp Pro Arg Leu Ser Ser Gln Cys Leu His Gln Asn
690                 695                 700 ggg gaa act ttg tat aac agt ggt gac acc tgg gtc cag aat tgt caa    2160
Gly Glu Thr Leu Tyr Asn Ser Gly Asp Thr Trp Val Gln Asn Cys Gln
705                 710                 715                 720 cag tgc cgc tgc ttg caa ggg gaa gtt gat tgt tgg ccc ctg cct tgc    2208
Gln Cys Arg Cys Leu Gln Gly Glu Val Asp Cys Trp Pro Leu Pro Cys
                725                 730                 735 cca gat gtg gag tgt gaa ttc agc att ctc cca gag aat gag tgc tgc    2256
Pro Asp Val Glu Cys Glu Phe Ser Ile Leu Pro Glu Asn Glu Cys Cys
            740                 745                 750 ccg cgc tgt gtc aca gac cct tgc cag gct gac acc atc cgc aat gac    2304
Pro Arg Cys Val Thr Asp Pro Cys Gln Ala Asp Thr Ile Arg Asn Asp
        755                 760                 765 atc acc aag act tgc ctg gac gaa atg aat gtg gtt cgc ttc acc ggg    2352
Ile Thr Lys Thr Cys Leu Asp Glu Met Asn Val Val Arg Phe Thr Gly
770                 775                 780 tcc tct tgg atc aaa cat ggc act gag tgt act ctc tgc cag tgc aag    2400
Ser Ser Trp Ile Lys His Gly Thr Glu Cys Thr Leu Cys Gln Cys Lys
785                 790                 795                 800 aat ggc cac atc tgt tgc tca gtg gat cca cag tgc ctt cag gaa ctg    2448
Asn Gly His Ile Cys Cys Ser Val Asp Pro Gln Cys Leu Gln Glu Leu
                805                 810                 815 tga                                                                 2451

<210> SEQ ID NO 8
<211> LENGTH: 816
<212> TYPE: PRT
<213> ORGANISM: Homo sapiens

<400> SEQUENCE: 8

Met Glu Ser Arg Val Leu Leu Arg Thr Phe Cys Leu Ile Phe Gly Leu
1               5                   10                  15

Gly Ala Val Trp Gly Leu Gly Val Asp Pro Ser Leu Gln Ile Asp Val
            20                  25                  30

Leu Thr Glu Leu Glu Leu Gly Glu Ser Thr Thr Gly Val Arg Gln Val
        35                  40                  45

Pro Gly Leu His Asn Gly Thr Lys Ala Phe Leu Phe Gln Asp Thr Pro
    50                  55                  60

Arg Ser Ile Lys Ala Ser Thr Ala Thr Ala Glu Gln Phe Phe Gln Lys
65                  70                  75                  80

Leu Arg Asn Lys His Glu Phe Thr Ile Leu Val Thr Leu Lys Gln Thr
                85                  90                  95

His Leu Asn Ser Gly Val Ile Leu Ser Ile His His Leu Asp His Arg
            100                 105                 110

Tyr Leu Glu Leu Glu Ser Ser Gly His Arg Asn Glu Val Arg Leu His
        115                 120                 125

Tyr Arg Ser Gly Ser His Arg Pro His Thr Glu Val Phe Pro Tyr Ile
    130                 135                 140

Leu Ala Asp Asp Lys Trp His Lys Leu Ser Leu Ala Ile Ser Ala Ser
145                 150                 155                 160

His Leu Ile Leu His Ile Asp Cys Asn Lys Ile Tyr Glu Arg Val Val
                165                 170                 175
```

-continued

```
Glu Lys Pro Ser Thr Asp Leu Pro Leu Gly Thr Thr Phe Trp Leu Gly
            180                 185                 190
Gln Arg Asn Asn Ala His Gly Tyr Phe Lys Gly Ile Met Gln Asp Val
        195                 200                 205
Gln Leu Leu Val Met Pro Gln Gly Phe Ile Ala Gln Cys Pro Asp Leu
    210                 215                 220
Asn Arg Thr Cys Pro Thr Cys Asn Asp Phe His Gly Leu Val Gln Lys
225                 230                 235                 240
Ile Met Glu Leu Gln Asp Ile Leu Ala Lys Thr Ser Ala Lys Leu Ser
                245                 250                 255
Arg Ala Glu Gln Arg Met Asn Arg Leu Asp Gln Cys Tyr Cys Glu Arg
            260                 265                 270
Thr Cys Thr Met Lys Gly Thr Thr Tyr Arg Glu Phe Glu Ser Trp Ile
        275                 280                 285
Asp Gly Cys Lys Asn Cys Thr Cys Leu Asn Gly Thr Ile Gln Cys Glu
    290                 295                 300
Thr Leu Ile Cys Pro Asn Pro Asp Cys Pro Leu Lys Ser Ala Leu Ala
305                 310                 315                 320
Tyr Val Asp Gly Lys Cys Cys Lys Glu Cys Lys Ser Ile Cys Gln Phe
                325                 330                 335
Gln Gly Arg Thr Tyr Phe Glu Gly Glu Arg Asn Thr Val Tyr Ser Ser
            340                 345                 350
Ser Gly Val Cys Val Leu Tyr Glu Cys Lys Asp Gln Thr Met Lys Leu
        355                 360                 365
Val Glu Ser Ser Gly Cys Pro Ala Leu Asp Cys Pro Glu Ser His Gln
    370                 375                 380
Ile Thr Leu Ser His Ser Cys Cys Lys Val Cys Lys Gly Tyr Asp Phe
385                 390                 395                 400
Cys Ser Glu Arg His Asn Cys Met Glu Asn Ser Ile Cys Arg Asn Leu
                405                 410                 415
Asn Asp Arg Ala Val Cys Ser Cys Arg Asp Gly Phe Arg Ala Leu Arg
            420                 425                 430
Glu Asp Asn Ala Tyr Cys Glu Asp Ile Asp Glu Cys Ala Glu Gly Arg
        435                 440                 445
His Tyr Cys Arg Glu Asn Thr Met Cys Val Asn Thr Pro Gly Ser Phe
    450                 455                 460
Met Cys Ile Cys Lys Thr Gly Tyr Ile Arg Ile Asp Asp Tyr Ser Cys
465                 470                 475                 480
Thr Glu His Asp Glu Cys Ile Thr Asn Gln His Asn Cys Asp Glu Asn
                485                 490                 495
Ala Leu Cys Phe Asn Thr Val Gly Gly His Asn Cys Val Cys Lys Pro
            500                 505                 510
Gly Tyr Thr Gly Asn Gly Thr Thr Cys Lys Ala Phe Cys Lys Asp Gly
        515                 520                 525
Cys Arg Asn Gly Gly Ala Cys Ile Ala Ala Asn Val Cys Ala Cys Pro
    530                 535                 540
Gln Gly Phe Thr Gly Pro Ser Cys Glu Thr Asp Ile Asp Glu Cys Ser
545                 550                 555                 560
Asp Gly Phe Val Gln Cys Asp Ser Arg Ala Asn Cys Ile Asn Leu Pro
                565                 570                 575
Gly Trp Tyr His Cys Glu Cys Arg Asp Gly Tyr His Asp Asn Gly Met
            580                 585                 590
```

```
Phe Ser Pro Ser Gly Glu Ser Cys Glu Asp Ile Asp Glu Cys Gly Thr
            595                 600                 605

Gly Arg His Ser Cys Ala Asn Asp Thr Ile Cys Phe Asn Leu Asp Gly
            610                 615                 620

Gly Tyr Asp Cys Arg Cys Pro His Gly Lys Asn Cys Thr Gly Asp Cys
625                 630                 635                 640

Ile His Asp Gly Lys Val Lys His Asn Gly Gln Ile Trp Val Leu Glu
                645                 650                 655

Asn Asp Arg Cys Ser Val Cys Ser Cys Gln Asn Gly Phe Val Met Cys
            660                 665                 670

Arg Arg Met Val Cys Asp Cys Glu Asn Pro Thr Val Asp Leu Phe Cys
            675                 680                 685

Cys Pro Glu Cys Asp Pro Arg Leu Ser Ser Gln Cys Leu His Gln Asn
            690                 695                 700

Gly Glu Thr Leu Tyr Asn Ser Gly Asp Thr Trp Val Gln Asn Cys Gln
705                 710                 715                 720

Gln Cys Arg Cys Leu Gln Gly Glu Val Asp Cys Trp Pro Leu Pro Cys
                725                 730                 735

Pro Asp Val Glu Cys Glu Phe Ser Ile Leu Pro Glu Asn Glu Cys Cys
            740                 745                 750

Pro Arg Cys Val Thr Asp Pro Cys Gln Ala Asp Thr Ile Arg Asn Asp
            755                 760                 765

Ile Thr Lys Thr Cys Leu Asp Glu Met Asn Val Val Arg Phe Thr Gly
770                 775                 780

Ser Ser Trp Ile Lys His Gly Thr Glu Cys Thr Leu Cys Gln Cys Lys
785                 790                 795                 800

Asn Gly His Ile Cys Cys Ser Val Asp Pro Gln Cys Leu Gln Glu Leu
                805                 810                 815

<210> SEQ ID NO 9
<211> LENGTH: 2451
<212> TYPE: DNA
<213> ORGANISM: Rattus norvegicus
<220> FEATURE:
<221> NAME/KEY: CDS
<222> LOCATION: (1)..(2451)

<400> SEQUENCE: 9 atg gaa tcc cgg gta tta ctg aga acg ttc tgc gtg atc ctc ggg ctc      48
Met Glu Ser Arg Val Leu Leu Arg Thr Phe Cys Val Ile Leu Gly Leu
1               5                   10                  15 gaa gcg gtt tgg gga ctt ggt gtg gac ccc tcc cta cag att gac gtc      96
Glu Ala Val Trp Gly Leu Gly Val Asp Pro Ser Leu Gln Ile Asp Val
                20                  25                  30 tta tca gag tta gaa ctt ggg gag tcc aca gct gga gtg cgc caa gtc     144
Leu Ser Glu Leu Glu Leu Gly Glu Ser Thr Ala Gly Val Arg Gln Val
            35                  40                  45 cca gga ctg cat aat ggg acg aaa gcc ttc ctc ttc caa gat tcc ccc     192
Pro Gly Leu His Asn Gly Thr Lys Ala Phe Leu Phe Gln Asp Ser Pro
        50                  55                  60 aga agc ata aaa gca ccc att gct aca gct gag cgg ttt ttc cag aag     240
Arg Ser Ile Lys Ala Pro Ile Ala Thr Ala Glu Arg Phe Phe Gln Lys
65                  70                  75                  80 ctg agg aat aaa cac gag ttc aca att ctg gtg acc ctg aaa cag atc     288
Leu Arg Asn Lys His Glu Phe Thr Ile Leu Val Thr Leu Lys Gln Ile
                85                  90                  95 cac tta aat tcg gga gtc att ctc tcc atc cac cac ttg gat cac agg     336
His Leu Asn Ser Gly Val Ile Leu Ser Ile His His Leu Asp His Arg
```

-continued

```
                100                 105                 110
tac ctg gaa ctg gaa agc agc ggc cac cgg aat gag atc aga ctg cat      384
Tyr Leu Glu Leu Glu Ser Ser Gly His Arg Asn Glu Ile Arg Leu His
        115                 120                 125 tac cgc tct gga act cac cgc ccg cac acg gaa gtg ttt cct tat att      432
Tyr Arg Ser Gly Thr His Arg Pro His Thr Glu Val Phe Pro Tyr Ile
130                 135                 140 ttg gct gat gcc aag tgg cac aag ctc tcc tta gcc ttc agt gcc tcc      480
Leu Ala Asp Ala Lys Trp His Lys Leu Ser Leu Ala Phe Ser Ala Ser
145                 150                 155                 160 cac tta att tta cac atc gac tgc aac aag atc tat gaa cga gtg gtg      528
His Leu Ile Leu His Ile Asp Cys Asn Lys Ile Tyr Glu Arg Val Val
                165                 170                 175 gaa atg cct tct aca gac ttg cct ctg ggc acc aca ttt tgg ttg gga      576
Glu Met Pro Ser Thr Asp Leu Pro Leu Gly Thr Thr Phe Trp Leu Gly
            180                 185                 190 cag aga aat aac gca cac ggg tat ttt aag gga ata atg caa gat gtg      624
Gln Arg Asn Asn Ala His Gly Tyr Phe Lys Gly Ile Met Gln Asp Val
        195                 200                 205 caa tta ctt gtc atg ccc cag ggg ttc atc gct cag tgc ccg gat ctt      672
Gln Leu Leu Val Met Pro Gln Gly Phe Ile Ala Gln Cys Pro Asp Leu
    210                 215                 220 aat cga acc tgt cca aca tgc aac gac ttc cat ggg ctt gtg cag aaa      720
Asn Arg Thr Cys Pro Thr Cys Asn Asp Phe His Gly Leu Val Gln Lys
225                 230                 235                 240 atc atg gag ctg cag gac att tta tcg aag acg tca gcc aag ttg tct      768
Ile Met Glu Leu Gln Asp Ile Leu Ser Lys Thr Ser Ala Lys Leu Ser
                245                 250                 255 aga gct gaa caa cga atg aac agg ctg gat cag tgc tac tgt gag cgg      816
Arg Ala Glu Gln Arg Met Asn Arg Leu Asp Gln Cys Tyr Cys Glu Arg
            260                 265                 270 acg tgc acc atg aag gga gcc acc tac cgg gag ttc gag tcc tgg aca      864
Thr Cys Thr Met Lys Gly Ala Thr Tyr Arg Glu Phe Glu Ser Trp Thr
        275                 280                 285 gac ggc tgc aag aac tgc aca tgc ttg aat ggg acc atc cag tgc gag      912
Asp Gly Cys Lys Asn Cys Thr Cys Leu Asn Gly Thr Ile Gln Cys Glu
    290                 295                 300 act ctg gtc tgc cct gct ccc gac tgc ccg gct aaa tcg gct cca gcg      960
Thr Leu Val Cys Pro Ala Pro Asp Cys Pro Ala Lys Ser Ala Pro Ala
305                 310                 315                 320 tac gtg gat ggc aag tgc tgt aag gag tgc aag tcc acc tgc cag ttc     1008
Tyr Val Asp Gly Lys Cys Cys Lys Glu Cys Lys Ser Thr Cys Gln Phe
                325                 330                 335 cag ggg cgg agc tac ttt gag gga gaa agg agc aca gtc ttc tca gct     1056
Gln Gly Arg Ser Tyr Phe Glu Gly Glu Arg Ser Thr Val Phe Ser Ala
            340                 345                 350 tcc gga atg tgc gtc ttg tat gaa tgc aag gat cag acc atg aag ctt     1104
Ser Gly Met Cys Val Leu Tyr Glu Cys Lys Asp Gln Thr Met Lys Leu
        355                 360                 365 gtt gag aac gcc ggc tgc ccg gct tta gat tgc ccc gag tct cat cag     1152
Val Glu Asn Ala Gly Cys Pro Ala Leu Asp Cys Pro Glu Ser His Gln
    370                 375                 380 atc gcc ttg tct cac agc tgc tgc aag gtt tgc aaa ggt tat gac ttc     1200
Ile Ala Leu Ser His Ser Cys Cys Lys Val Cys Lys Gly Tyr Asp Phe
385                 390                 395                 400 tgt tct gag aag cat aca tgc atg gag aac tca gtc tgc agg aac ctg     1248
Cys Ser Glu Lys His Thr Cys Met Glu Asn Ser Val Cys Arg Asn Leu
                405                 410                 415 aac gac agg gca gtg tgc agc tgc cgg gat ggt ttc cgg gcc ctc cgg     1296
```

```
Asn Asp Arg Ala Val Cys Ser Cys Arg Asp Gly Phe Arg Ala Leu Arg
        420                 425                 430 gag gac aat gcc tac tgt gaa gac att gac gag tgt gca gag ggg cgc      1344
Glu Asp Asn Ala Tyr Cys Glu Asp Ile Asp Glu Cys Ala Glu Gly Arg
        435                 440                 445 cat tac tgc cgt gag aac acc atg tgt gtg aac aca ccg ggc tct ttc      1392
His Tyr Cys Arg Glu Asn Thr Met Cys Val Asn Thr Pro Gly Ser Phe
        450                 455                 460 ctg tgt atc tgc caa aca ggg tac atc aga atc gac gat tac tcg tgt      1440
Leu Cys Ile Cys Gln Thr Gly Tyr Ile Arg Ile Asp Asp Tyr Ser Cys
465                 470                 475                 480 acg gaa cat gac gag tgc ctc aca aac cag cac aac tgt gac gag aac      1488
Thr Glu His Asp Glu Cys Leu Thr Asn Gln His Asn Cys Asp Glu Asn
                485                 490                 495 gct ttg tgc ttt aac acc gtt gga ggt cac aac tgt gtc tgc aag cct      1536
Ala Leu Cys Phe Asn Thr Val Gly Gly His Asn Cys Val Cys Lys Pro
            500                 505                 510 ggg tac act ggg aat gga acc acg tgc aaa gct ttc tgc aaa gac ggc      1584
Gly Tyr Thr Gly Asn Gly Thr Thr Cys Lys Ala Phe Cys Lys Asp Gly
        515                 520                 525 tgc aaa aac gga ggt gcc tgc att gct gcc aat gtc tgt gct tgc cca      1632
Cys Lys Asn Gly Gly Ala Cys Ile Ala Ala Asn Val Cys Ala Cys Pro
    530                 535                 540 caa ggc ttc acc gga ccc agc tgt gag aca gac att gat gag tgc tct      1680
Gln Gly Phe Thr Gly Pro Ser Cys Glu Thr Asp Ile Asp Glu Cys Ser
545                 550                 555                 560 gag ggc ttt gtt cag tgt gac agc cgt gcc aac tgc att aac ctg cct      1728
Glu Gly Phe Val Gln Cys Asp Ser Arg Ala Asn Cys Ile Asn Leu Pro
                565                 570                 575 ggg tgg tac cac tgt gag tgc aga gat ggc tac cat gac aat ggg atg      1776
Gly Trp Tyr His Cys Glu Cys Arg Asp Gly Tyr His Asp Asn Gly Met
            580                 585                 590 ttt gcg cca ggt gga gaa tcc tgt gaa gat att gat gaa tgt ggg act      1824
Phe Ala Pro Gly Gly Glu Ser Cys Glu Asp Ile Asp Glu Cys Gly Thr
        595                 600                 605 ggg agg cac agc tgt gcc aat gac acc att tgc ttc aac ttg gac ggt      1872
Gly Arg His Ser Cys Ala Asn Asp Thr Ile Cys Phe Asn Leu Asp Gly
    610                 615                 620 ggc tac gat tgc cgg tgt ccc cat gga aag aac tgc aca ggg gac tgc      1920
Gly Tyr Asp Cys Arg Cys Pro His Gly Lys Asn Cys Thr Gly Asp Cys
625                 630                 635                 640 gtg cac gac ggg aaa gtc aaa cac aac ggc cag atc tgg gtg ctg gag      1968
Val His Asp Gly Lys Val Lys His Asn Gly Gln Ile Trp Val Leu Glu
                645                 650                 655 aac gac agg tgc tct gtg tgt tcc tgc cag act gga ttt gtt atg tgc      2016
Asn Asp Arg Cys Ser Val Cys Ser Cys Gln Thr Gly Phe Val Met Cys
            660                 665                 670 caa cgg atg gtc tgt gac tgc gaa aac ccc aca gtt gac ctc tcc tgc      2064
Gln Arg Met Val Cys Asp Cys Glu Asn Pro Thr Val Asp Leu Ser Cys
        675                 680                 685 tgc cct gag tgc gac cca agg ctg agc agc cag tgc ctg cat caa aac      2112
Cys Pro Glu Cys Asp Pro Arg Leu Ser Ser Gln Cys Leu His Gln Asn
    690                 695                 700 ggg gaa acc gtg tac aac agc ggt gac acc tgg gcc cag gat tgc cgt      2160
Gly Glu Thr Val Tyr Asn Ser Gly Asp Thr Trp Ala Gln Asp Cys Arg
705                 710                 715                 720 cag tgc cgc tgc ttg caa gaa gaa gtt gac tgc tgg ccc ctg gct tgc      2208
Gln Cys Arg Cys Leu Gln Glu Glu Val Asp Cys Trp Pro Leu Ala Cys
                725                 730                 735
```

-continued

```
cca gag gta gag tgt gaa ttt agt gtc ctt cct gag aac gag tgc tgc    2256
Pro Glu Val Glu Cys Glu Phe Ser Val Leu Pro Glu Asn Glu Cys Cys
            740                 745                 750 cca cgc tgt gtc acc gat cct tgt cag gct gac acc atc cgc aat gac    2304
Pro Arg Cys Val Thr Asp Pro Cys Gln Ala Asp Thr Ile Arg Asn Asp
        755                 760                 765 atc acc aaa acc tgc ctg gac gag atg aac gtg gtt cgc ttc act ggg    2352
Ile Thr Lys Thr Cys Leu Asp Glu Met Asn Val Val Arg Phe Thr Gly
770                 775                 780 tct tcc tgg atc aag cac ggc acg gag tgc acc ctc tgc cag tgc aag    2400
Ser Ser Trp Ile Lys His Gly Thr Glu Cys Thr Leu Cys Gln Cys Lys
785                 790                 795                 800 aac ggc cac gtg tgc tgc tca gtg gac cca cag tgc ctc cag gag ctg    2448
Asn Gly His Val Cys Cys Ser Val Asp Pro Gln Cys Leu Gln Glu Leu
            805                 810                 815 tga                                                                2451
```

<210> SEQ ID NO 10
<211> LENGTH: 816
<212> TYPE: PRT
<213> ORGANISM: Rattus norvegicus

<400> SEQUENCE: 10

```
Met Glu Ser Arg Val Leu Leu Arg Thr Phe Cys Val Ile Leu Gly Leu
1               5                   10                  15

Glu Ala Val Trp Gly Leu Gly Val Asp Pro Ser Leu Gln Ile Asp Val
            20                  25                  30

Leu Ser Glu Leu Glu Leu Gly Glu Ser Thr Ala Gly Val Arg Gln Val
        35                  40                  45

Pro Gly Leu His Asn Gly Thr Lys Ala Phe Leu Phe Gln Asp Ser Pro
    50                  55                  60

Arg Ser Ile Lys Ala Pro Ile Ala Thr Ala Glu Arg Phe Phe Gln Lys
65                  70                  75                  80

Leu Arg Asn Lys His Glu Phe Thr Ile Leu Val Thr Leu Lys Gln Ile
                85                  90                  95

His Leu Asn Ser Gly Val Ile Leu Ser Ile His His Leu Asp His Arg
            100                 105                 110

Tyr Leu Glu Leu Glu Ser Ser Gly His Arg Asn Glu Ile Arg Leu His
        115                 120                 125

Tyr Arg Ser Gly Thr His Arg Pro His Thr Glu Val Phe Pro Tyr Ile
    130                 135                 140

Leu Ala Asp Ala Lys Trp His Lys Leu Ser Leu Ala Phe Ser Ala Ser
145                 150                 155                 160

His Leu Ile Leu His Ile Asp Cys Asn Lys Ile Tyr Glu Arg Val Val
                165                 170                 175

Glu Met Pro Ser Thr Asp Leu Pro Leu Gly Thr Thr Phe Trp Leu Gly
            180                 185                 190

Gln Arg Asn Asn Ala His Gly Tyr Phe Lys Gly Ile Met Gln Asp Val
        195                 200                 205

Gln Leu Leu Val Met Pro Gln Gly Phe Ile Ala Gln Cys Pro Asp Leu
    210                 215                 220

Asn Arg Thr Cys Pro Thr Cys Asn Asp Phe His Gly Leu Val Gln Lys
225                 230                 235                 240

Ile Met Glu Leu Gln Asp Ile Leu Ser Lys Thr Ser Ala Lys Leu Ser
                245                 250                 255

Arg Ala Glu Gln Arg Met Asn Arg Leu Asp Gln Cys Tyr Cys Glu Arg
```

```
                 260                 265                 270
Thr Cys Thr Met Lys Gly Ala Thr Tyr Arg Glu Phe Glu Ser Trp Thr
            275                 280                 285
Asp Gly Cys Lys Asn Cys Thr Cys Leu Asn Gly Thr Ile Gln Cys Glu
            290                 295                 300
Thr Leu Val Cys Pro Ala Pro Asp Cys Pro Ala Lys Ser Ala Pro Ala
305                 310                 315                 320
Tyr Val Asp Gly Lys Cys Cys Lys Glu Cys Lys Ser Thr Cys Gln Phe
                325                 330                 335
Gln Gly Arg Ser Tyr Phe Glu Gly Glu Arg Ser Thr Val Phe Ser Ala
            340                 345                 350
Ser Gly Met Cys Val Leu Tyr Glu Cys Lys Asp Gln Thr Met Lys Leu
            355                 360                 365
Val Glu Asn Ala Gly Cys Pro Ala Leu Asp Cys Pro Glu Ser His Gln
            370                 375                 380
Ile Ala Leu Ser His Ser Cys Cys Lys Val Cys Lys Gly Tyr Asp Phe
385                 390                 395                 400
Cys Ser Glu Lys His Thr Cys Met Glu Asn Ser Val Cys Arg Asn Leu
                405                 410                 415
Asn Asp Arg Ala Val Cys Ser Cys Arg Asp Gly Phe Arg Ala Leu Arg
            420                 425                 430
Glu Asp Asn Ala Tyr Cys Glu Asp Ile Asp Glu Cys Ala Glu Gly Arg
            435                 440                 445
His Tyr Cys Arg Glu Asn Thr Met Cys Val Asn Thr Pro Gly Ser Phe
            450                 455                 460
Leu Cys Ile Cys Gln Thr Gly Tyr Ile Arg Ile Asp Asp Tyr Ser Cys
465                 470                 475                 480
Thr Glu His Asp Glu Cys Leu Thr Asn Gln His Asn Cys Asp Glu Asn
                485                 490                 495
Ala Leu Cys Phe Asn Thr Val Gly Gly His Asn Cys Val Cys Lys Pro
            500                 505                 510
Gly Tyr Thr Gly Asn Gly Thr Thr Cys Lys Ala Phe Cys Lys Asp Gly
            515                 520                 525
Cys Lys Asn Gly Gly Ala Cys Ile Ala Ala Asn Val Cys Ala Cys Pro
            530                 535                 540
Gln Gly Phe Thr Gly Pro Ser Cys Glu Thr Asp Ile Asp Glu Cys Ser
545                 550                 555                 560
Glu Gly Phe Val Gln Cys Asp Ser Arg Ala Asn Cys Ile Asn Leu Pro
                565                 570                 575
Gly Trp Tyr His Cys Glu Cys Arg Asp Gly Tyr His Asp Asn Gly Met
            580                 585                 590
Phe Ala Pro Gly Gly Glu Ser Cys Glu Asp Ile Asp Glu Cys Gly Thr
            595                 600                 605
Gly Arg His Ser Cys Ala Asn Asp Thr Ile Cys Phe Asn Leu Asp Gly
            610                 615                 620
Gly Tyr Asp Cys Arg Cys Pro His Gly Lys Asn Cys Thr Gly Asp Cys
625                 630                 635                 640
Val His Asp Gly Lys Val Lys His Asn Gly Gln Ile Trp Val Leu Glu
                645                 650                 655
Asn Asp Arg Cys Ser Val Cys Ser Cys Gln Thr Gly Phe Val Met Cys
            660                 665                 670
Gln Arg Met Val Cys Asp Cys Glu Asn Pro Thr Val Asp Leu Ser Cys
            675                 680                 685
```

```
Cys Pro Glu Cys Asp Pro Arg Leu Ser Ser Gln Cys Leu His Gln Asn
        690                 695                 700

Gly Glu Thr Val Tyr Asn Ser Gly Asp Thr Trp Ala Gln Asp Cys Arg
705                 710                 715                 720

Gln Cys Arg Cys Leu Gln Glu Glu Val Asp Cys Trp Pro Leu Ala Cys
                725                 730                 735

Pro Glu Val Glu Cys Glu Phe Ser Val Leu Pro Glu Asn Glu Cys Cys
            740                 745                 750

Pro Arg Cys Val Thr Asp Pro Cys Gln Ala Asp Thr Ile Arg Asn Asp
        755                 760                 765

Ile Thr Lys Thr Cys Leu Asp Glu Met Asn Val Val Arg Phe Thr Gly
    770                 775                 780

Ser Ser Trp Ile Lys His Gly Thr Glu Cys Thr Leu Cys Gln Cys Lys
785                 790                 795                 800

Asn Gly His Val Cys Cys Ser Val Asp Pro Gln Cys Leu Gln Glu Leu
                805                 810                 815

<210> SEQ ID NO 11
<211> LENGTH: 2460
<212> TYPE: DNA
<213> ORGANISM: Mus musculus
<220> FEATURE:
<221> NAME/KEY: CDS
<222> LOCATION: (1)..(2460)

<400> SEQUENCE: 11 atg cac gcc atg gaa tcc cgg gtg tta ctg aga acg ttc tgc gtg atc      48
Met His Ala Met Glu Ser Arg Val Leu Leu Arg Thr Phe Cys Val Ile
1               5                   10                  15 ctc ggc ctt gga gcg gtt tgg ggg ctt ggt gtg gac ccc tcc cta cag      96
Leu Gly Leu Gly Ala Val Trp Gly Leu Gly Val Asp Pro Ser Leu Gln
                20                  25                  30 att gac gtc tta aca gag tta gaa ctt ggg gag tct aca gat gga gtg     144
Ile Asp Val Leu Thr Glu Leu Glu Leu Gly Glu Ser Thr Asp Gly Val
            35                  40                  45 cgc caa gtc ccg gga ctg cat aat ggg acg aaa gcc ttc ctc ttc caa     192
Arg Gln Val Pro Gly Leu His Asn Gly Thr Lys Ala Phe Leu Phe Gln
    50                  55                  60 gag tcc ccc aga agc ata aag gca tcc act gct aca gct gag cgg ttt     240
Glu Ser Pro Arg Ser Ile Lys Ala Ser Thr Ala Thr Ala Glu Arg Phe
65                  70                  75                  80 ctc cag aag ctg aga aat aaa cac gag ttc aca atc ttg gtg acc tta     288
Leu Gln Lys Leu Arg Asn Lys His Glu Phe Thr Ile Leu Val Thr Leu
                85                  90                  95 aaa cag atc cac tta aat tcg gga gtt atc ctc tcc atc cac cac ttg     336
Lys Gln Ile His Leu Asn Ser Gly Val Ile Leu Ser Ile His His Leu
                100                 105                 110 gat cac agg tac ctg gaa ctg gaa agc agt ggc cat cgg aat gag atc     384
Asp His Arg Tyr Leu Glu Leu Glu Ser Ser Gly His Arg Asn Glu Ile
            115                 120                 125 aga ctc cac tac cgc tct ggc act cac cgc ccc cac acg gaa gtg ttt     432
Arg Leu His Tyr Arg Ser Gly Thr His Arg Pro His Thr Glu Val Phe
    130                 135                 140 cct tat att ttg gct gat gcc aag tgg cac aag ctc tcc tta gcc ttc     480
Pro Tyr Ile Leu Ala Asp Ala Lys Trp His Lys Leu Ser Leu Ala Phe
145                 150                 155                 160 agt gcc tct cac tta att tta cac atc gac tgc aat aag atc tat gaa     528
Ser Ala Ser His Leu Ile Leu His Ile Asp Cys Asn Lys Ile Tyr Glu
                165                 170                 175
```

-continued

```
cga gtg gtg gaa atg ccc ttc aca gac ttg gct ctg ggc aca aca ttt         576
Arg Val Val Glu Met Pro Phe Thr Asp Leu Ala Leu Gly Thr Thr Phe
        180                 185                 190 tgg ttg gga cag aga aat aat gca cat ggc tat ttt aag gga ata atg         624
Trp Leu Gly Gln Arg Asn Asn Ala His Gly Tyr Phe Lys Gly Ile Met
    195                 200                 205 cag gat gtg cac gtc ctt gtc atg cct cag ggc ttc att gct cag tgc         672
Gln Asp Val His Val Leu Val Met Pro Gln Gly Phe Ile Ala Gln Cys
210                 215                 220 ccg gac ctt aat cga acc tgt cca aca tgc aac gac ttc cat ggg ctt         720
Pro Asp Leu Asn Arg Thr Cys Pro Thr Cys Asn Asp Phe His Gly Leu
225                 230                 235                 240 gtg cag aaa atc atg gag ctg cag gac att tta tca aag acg tca gcc         768
Val Gln Lys Ile Met Glu Leu Gln Asp Ile Leu Ser Lys Thr Ser Ala
        245                 250                 255 aag ctg tcc cga gct gaa caa aga atg aac agg ctg gat cag tgc tac         816
Lys Leu Ser Arg Ala Glu Gln Arg Met Asn Arg Leu Asp Gln Cys Tyr
    260                 265                 270 tgt gag cgg aca tgc act gtg aag gga acc acc tac cga gag tct gag         864
Cys Glu Arg Thr Cys Thr Val Lys Gly Thr Thr Tyr Arg Glu Ser Glu
275                 280                 285 tcc tgg aca gac ggc tgt aag aac tgc aca tgc ttg aac ggg acc atc         912
Ser Trp Thr Asp Gly Cys Lys Asn Cys Thr Cys Leu Asn Gly Thr Ile
        290                 295                 300 cag tgc gag act ctg gtc tgc cct gct cct gac tgc cct cct aaa tcg         960
Gln Cys Glu Thr Leu Val Cys Pro Ala Pro Asp Cys Pro Pro Lys Ser
305                 310                 315                 320 gcc cct gcg tat gtg gat ggc aag tgt tgt aag gag tgc aaa tca acc        1008
Ala Pro Ala Tyr Val Asp Gly Lys Cys Cys Lys Glu Cys Lys Ser Thr
        325                 330                 335 tgc cag ttc cag gga cgg agc tac ttt gag gga gaa agg aac acg gca        1056
Cys Gln Phe Gln Gly Arg Ser Tyr Phe Glu Gly Glu Arg Asn Thr Ala
    340                 345                 350 tac tca tct tct gga atg tgt gtc tta tat gaa tgc aag gat cag acc        1104
Tyr Ser Ser Ser Gly Met Cys Val Leu Tyr Glu Cys Lys Asp Gln Thr
355                 360                 365 atg aag ctt gtt gag aac att ggc tgc cca ccc tta gat tgt ccc gag        1152
Met Lys Leu Val Glu Asn Ile Gly Cys Pro Pro Leu Asp Cys Pro Glu
        370                 375                 380 tct cat cag att gcc ttg tct cac agc tgc tgc aag gtt tgt aaa ggt        1200
Ser His Gln Ile Ala Leu Ser His Ser Cys Cys Lys Val Cys Lys Gly
385                 390                 395                 400 tat gac ttc tgt tct gag aag cat acc tgc atg gag aac tcg gtc tgc        1248
Tyr Asp Phe Cys Ser Glu Lys His Thr Cys Met Glu Asn Ser Val Cys
        405                 410                 415 agg aac ctg aac gac agg gtt gtg tgc agc tgc agg gat ggt ttt cgg        1296
Arg Asn Leu Asn Asp Arg Val Val Cys Ser Cys Arg Asp Gly Phe Arg
    420                 425                 430 gct ctc cga gag gac aac gcc tac tgt gaa gac att gac gag tgt gca        1344
Ala Leu Arg Glu Asp Asn Ala Tyr Cys Glu Asp Ile Asp Glu Cys Ala
435                 440                 445 gaa ggg cgc cat tac tgc cgt gag aac acc atg tgt gtg aat aca cct        1392
Glu Gly Arg His Tyr Cys Arg Glu Asn Thr Met Cys Val Asn Thr Pro
        450                 455                 460 ggt tct ttc atg tgt gtc tgc aaa act ggg tac atc agg atc gac gat       1440
Gly Ser Phe Met Cys Val Cys Lys Thr Gly Tyr Ile Arg Ile Asp Asp
465                 470                 475                 480 tac tca tgt aca gaa cat gat gag tgt ctc aca acc cag cac aat tgt       1488
Tyr Ser Cys Thr Glu His Asp Glu Cys Leu Thr Thr Gln His Asn Cys
```

-continued

```
                485                 490                 495
gat gaa aac gct ttg tgc ttt aac act gtt gga gga cac aac tgt gtc      1536
Asp Glu Asn Ala Leu Cys Phe Asn Thr Val Gly Gly His Asn Cys Val
            500                 505                 510 tgc aag cct ggc tac acc ggg aat gga acc acg tgc aaa gct ttc tgc      1584
Cys Lys Pro Gly Tyr Thr Gly Asn Gly Thr Thr Cys Lys Ala Phe Cys
        515                 520                 525 aaa gat ggc tgt aga aac gga gga gcg tgc att gct gcc aat gtg tgt      1632
Lys Asp Gly Cys Arg Asn Gly Gly Ala Cys Ile Ala Ala Asn Val Cys
    530                 535                 540 gcc tgc cca caa ggc ttc acg gga ccc agc tgt gag aca gac att gac      1680
Ala Cys Pro Gln Gly Phe Thr Gly Pro Ser Cys Glu Thr Asp Ile Asp
545                 550                 555                 560 gag tgc tct gag ggc ttt gtt cag tgt gac agc cgt gcc aac tgc atc      1728
Glu Cys Ser Glu Gly Phe Val Gln Cys Asp Ser Arg Ala Asn Cys Ile
                565                 570                 575 aac ctg cct ggg tgg tat cac tgt gag tgc aga gac ggc tac cat gac      1776
Asn Leu Pro Gly Trp Tyr His Cys Glu Cys Arg Asp Gly Tyr His Asp
            580                 585                 590 aat ggg atg ttt gcg cca ggc gga gaa tcc tgt gaa gat att gac gaa      1824
Asn Gly Met Phe Ala Pro Gly Gly Glu Ser Cys Glu Asp Ile Asp Glu
        595                 600                 605 tgc ggg act ggg agg cac agc tgc acc aac gac acc att tgc ttc aac      1872
Cys Gly Thr Gly Arg His Ser Cys Thr Asn Asp Thr Ile Cys Phe Asn
    610                 615                 620 ttg gac ggg gga tac gat tgc cgg tgt ccc cat ggg aag aac tgc act      1920
Leu Asp Gly Gly Tyr Asp Cys Arg Cys Pro His Gly Lys Asn Cys Thr
625                 630                 635                 640 ggg gac tgc gtg cac gag ggg aaa gtg aag cac acc ggc cag atc tgg      1968
Gly Asp Cys Val His Glu Gly Lys Val Lys His Thr Gly Gln Ile Trp
                645                 650                 655 gtg ctg gaa aac gac agg tgc tcc gtg tgt tcc tgg cag act ggg ttt      2016
Val Leu Glu Asn Asp Arg Cys Ser Val Cys Ser Trp Gln Thr Gly Phe
            660                 665                 670 gtc atg tgt cga cgg atg gtc tgc gac tgc gaa aac ccc aca gat gac      2064
Val Met Cys Arg Arg Met Val Cys Asp Cys Glu Asn Pro Thr Asp Asp
        675                 680                 685 ctt tcc tgc tgc cct gag tgt gac cca agg ctg agc agt cag tgc ctg      2112
Leu Ser Cys Cys Pro Glu Cys Asp Pro Arg Leu Ser Ser Gln Cys Leu
    690                 695                 700 cat caa aac ggg gaa acc gtg tac aac agc ggc gac acc tgg gtc cag      2160
His Gln Asn Gly Glu Thr Val Tyr Asn Ser Gly Asp Thr Trp Val Gln
705                 710                 715                 720 gat tgc cgt cag tgc cgc tgc ttg caa gga gaa gtt gac tgt tgg ccc      2208
Asp Cys Arg Gln Cys Arg Cys Leu Gln Gly Glu Val Asp Cys Trp Pro
                725                 730                 735 ctg gct tgc cca gag gta gaa tgt gaa ttt agc gtc ctt cct gag aac      2256
Leu Ala Cys Pro Glu Val Glu Cys Glu Phe Ser Val Leu Pro Glu Asn
            740                 745                 750 gag tgc tgc cca cgc tgt gtc acc gat cct tgt cag gcc gac acc atc      2304
Glu Cys Cys Pro Arg Cys Val Thr Asp Pro Cys Gln Ala Asp Thr Ile
        755                 760                 765 cgc aat gac atc acc aaa acc tgc ctg gac gag atg aac gtg gtt cgc      2352
Arg Asn Asp Ile Thr Lys Thr Cys Leu Asp Glu Met Asn Val Val Arg
    770                 775                 780 ttc acc ggg tct tcc tgg atc aag cac ggc acg gag tgt acc ctc tgc      2400
Phe Thr Gly Ser Ser Trp Ile Lys His Gly Thr Glu Cys Thr Leu Cys
785                 790                 795                 800 cag tgc aag aat ggc cat ttg tgc tgc tca gtg gat cca cag tgc ctt      2448
```

-continued

```
Gln Cys Lys Asn Gly His Leu Cys Cys Ser Val Asp Pro Gln Cys Leu
            805                 810                 815 cag gag ctg tga                                                              2460
Gln Glu Leu <210> SEQ ID NO 12
<211> LENGTH: 819
<212> TYPE: PRT
<213> ORGANISM: Mus musculus

<400> SEQUENCE: 12

Met His Ala Met Glu Ser Arg Val Leu Leu Arg Thr Phe Cys Val Ile
1               5                   10                  15

Leu Gly Leu Gly Ala Val Trp Gly Leu Gly Val Asp Pro Ser Leu Gln
            20                  25                  30

Ile Asp Val Leu Thr Glu Leu Glu Leu Gly Glu Ser Thr Asp Gly Val
        35                  40                  45

Arg Gln Val Pro Gly Leu His Asn Gly Thr Lys Ala Phe Leu Phe Gln
    50                  55                  60

Glu Ser Pro Arg Ser Ile Lys Ala Ser Thr Ala Thr Ala Glu Arg Phe
65                  70                  75                  80

Leu Gln Lys Leu Arg Asn Lys His Glu Phe Thr Ile Leu Val Thr Leu
                85                  90                  95

Lys Gln Ile His Leu Asn Ser Gly Val Ile Leu Ser Ile His His Leu
            100                 105                 110

Asp His Arg Tyr Leu Glu Leu Glu Ser Ser Gly His Arg Asn Glu Ile
        115                 120                 125

Arg Leu His Tyr Arg Ser Gly Thr His Arg Pro His Thr Glu Val Phe
    130                 135                 140

Pro Tyr Ile Leu Ala Asp Ala Lys Trp His Lys Leu Ser Leu Ala Phe
145                 150                 155                 160

Ser Ala Ser His Leu Ile Leu His Ile Asp Cys Asn Lys Ile Tyr Glu
                165                 170                 175

Arg Val Val Glu Met Pro Phe Thr Asp Leu Ala Leu Gly Thr Thr Phe
            180                 185                 190

Trp Leu Gly Gln Arg Asn Asn Ala His Gly Tyr Phe Lys Gly Ile Met
        195                 200                 205

Gln Asp Val His Val Leu Val Met Pro Gln Gly Phe Ile Ala Gln Cys
    210                 215                 220

Pro Asp Leu Asn Arg Thr Cys Pro Thr Cys Asn Asp Phe His Gly Leu
225                 230                 235                 240

Val Gln Lys Ile Met Glu Leu Gln Asp Ile Leu Ser Lys Thr Ser Ala
                245                 250                 255

Lys Leu Ser Arg Ala Glu Gln Arg Met Asn Arg Leu Asp Gln Cys Tyr
            260                 265                 270

Cys Glu Arg Thr Cys Thr Val Lys Gly Thr Thr Tyr Arg Glu Ser Glu
        275                 280                 285

Ser Trp Thr Asp Gly Cys Lys Asn Cys Thr Cys Leu Asn Gly Thr Ile
    290                 295                 300

Gln Cys Glu Thr Leu Val Cys Pro Ala Pro Asp Cys Pro Pro Lys Ser
305                 310                 315                 320

Ala Pro Ala Tyr Val Asp Gly Lys Cys Cys Lys Glu Cys Lys Ser Thr
                325                 330                 335

Cys Gln Phe Gln Gly Arg Ser Tyr Phe Glu Gly Glu Arg Asn Thr Ala
            340                 345                 350
```

```
Tyr Ser Ser Ser Gly Met Cys Val Leu Tyr Glu Cys Lys Asp Gln Thr
        355                 360                 365
Met Lys Leu Val Glu Asn Ile Gly Cys Pro Pro Leu Asp Cys Pro Glu
    370                 375                 380
Ser His Gln Ile Ala Leu Ser His Ser Cys Cys Lys Val Cys Lys Gly
385                 390                 395                 400
Tyr Asp Phe Cys Ser Glu Lys His Thr Cys Met Glu Asn Ser Val Cys
                405                 410                 415
Arg Asn Leu Asn Asp Arg Val Val Cys Ser Cys Arg Asp Gly Phe Arg
            420                 425                 430
Ala Leu Arg Glu Asp Asn Ala Tyr Cys Glu Asp Ile Asp Glu Cys Ala
        435                 440                 445
Glu Gly Arg His Tyr Cys Arg Glu Asn Thr Met Cys Val Asn Thr Pro
    450                 455                 460
Gly Ser Phe Met Cys Val Cys Lys Thr Gly Tyr Ile Arg Ile Asp Asp
465                 470                 475                 480
Tyr Ser Cys Thr Glu His Asp Glu Cys Leu Thr Thr His Asn Cys
                485                 490                 495
Asp Glu Asn Ala Leu Cys Phe Asn Thr Val Gly Gly His Asn Cys Val
            500                 505                 510
Cys Lys Pro Gly Tyr Thr Gly Asn Gly Thr Thr Cys Lys Ala Phe Cys
        515                 520                 525
Lys Asp Gly Cys Arg Asn Gly Gly Ala Cys Ile Ala Ala Asn Val Cys
    530                 535                 540
Ala Cys Pro Gln Gly Phe Thr Gly Pro Ser Cys Glu Thr Asp Ile Asp
545                 550                 555                 560
Glu Cys Ser Glu Gly Phe Val Gln Cys Asp Ser Arg Ala Asn Cys Ile
                565                 570                 575
Asn Leu Pro Gly Trp Tyr His Cys Glu Cys Arg Asp Gly Tyr His Asp
            580                 585                 590
Asn Gly Met Phe Ala Pro Gly Gly Glu Ser Cys Glu Asp Ile Asp Glu
        595                 600                 605
Cys Gly Thr Gly Arg His Ser Cys Thr Asn Asp Thr Ile Cys Phe Asn
    610                 615                 620
Leu Asp Gly Gly Tyr Asp Cys Arg Cys Pro His Gly Lys Asn Cys Thr
625                 630                 635                 640
Gly Asp Cys Val His Glu Gly Lys Val Lys His Thr Gly Gln Ile Trp
                645                 650                 655
Val Leu Glu Asn Asp Arg Cys Ser Val Cys Ser Trp Gln Thr Gly Phe
            660                 665                 670
Val Met Cys Arg Arg Met Val Cys Asp Cys Glu Asn Pro Thr Asp Asp
        675                 680                 685
Leu Ser Cys Cys Pro Glu Cys Asp Pro Arg Leu Ser Ser Gln Cys Leu
    690                 695                 700
His Gln Asn Gly Glu Thr Val Tyr Asn Ser Gly Asp Thr Trp Val Gln
705                 710                 715                 720
Asp Cys Arg Gln Cys Arg Cys Leu Gln Gly Glu Val Asp Cys Trp Pro
                725                 730                 735
Leu Ala Cys Pro Glu Val Glu Cys Glu Phe Ser Val Leu Pro Glu Asn
            740                 745                 750
Glu Cys Cys Pro Arg Cys Val Thr Asp Pro Cys Gln Ala Asp Thr Ile
        755                 760                 765
```

```
Arg Asn Asp Ile Thr Lys Thr Cys Leu Asp Glu Met Asn Val Val Arg
    770             775                 780

Phe Thr Gly Ser Ser Trp Ile Lys His Gly Thr Glu Cys Thr Leu Cys
785             790                 795                 800

Gln Cys Lys Asn Gly His Leu Cys Cys Ser Val Asp Pro Gln Cys Leu
            805                 810                 815

Gln Glu Leu

<210> SEQ ID NO 13
<211> LENGTH: 2453
<212> TYPE: DNA
<213> ORGANISM: Gallus gallus
<220> FEATURE:
<221> NAME/KEY: CDS
<222> LOCATION: (1)..(2451)

<400> SEQUENCE: 13
```

| | | | | | | | | | | | | | | | | |
|---|---|---|---|---|---|---|---|---|---|---|---|---|---|---|---|---|
| atg | gag | tcc | ggc | tgc | ggc | tta | ggc | acg | ctt | tgc | ctt | ctc | ctc | tgc | ctg | 48 |
| Met | Glu | Ser | Gly | Cys | Gly | Leu | Gly | Thr | Leu | Cys | Leu | Leu | Leu | Cys | Leu | |
| 1 | | | | 5 | | | | | 10 | | | | | 15 | | |
| ggg | cca | gtc | gta | ggc | ttc | ggc | gtg | gac | ccc | tcg | ctg | cag | atc | gac | gtg | 96 |
| Gly | Pro | Val | Val | Gly | Phe | Gly | Val | Asp | Pro | Ser | Leu | Gln | Ile | Asp | Val | |
| | | | 20 | | | | | 25 | | | | | 30 | | | |
| ctg | tcc | gag | ctg | ggg | ctg | ccg | ggc | tac | gcg | gcg | ggc | gtg | cgc | cag | gtg | 144 |
| Leu | Ser | Glu | Leu | Gly | Leu | Pro | Gly | Tyr | Ala | Ala | Gly | Val | Arg | Gln | Val | |
| | 35 | | | | | 40 | | | | | 45 | | | | | |
| ccg | ggg | ctg | cac | aac | ggg | agc | aaa | gcc | ttc | ctc | ttc | cca | gat | act | tca | 192 |
| Pro | Gly | Leu | His | Asn | Gly | Ser | Lys | Ala | Phe | Leu | Phe | Pro | Asp | Thr | Ser | |
| 50 | | | | | 55 | | | | | 60 | | | | | | |
| aga | agt | gta | aag | gcg | tct | cca | gaa | aca | gct | gaa | atc | ttt | ttt | cag | aag | 240 |
| Arg | Ser | Val | Lys | Ala | Ser | Pro | Glu | Thr | Ala | Glu | Ile | Phe | Phe | Gln | Lys | |
| 65 | | | | | 70 | | | | | 75 | | | | | 80 | |
| ttg | aga | aat | aaa | tat | gaa | ttc | aca | atc | ctg | gtg | acc | tta | aaa | caa | gcc | 288 |
| Leu | Arg | Asn | Lys | Tyr | Glu | Phe | Thr | Ile | Leu | Val | Thr | Leu | Lys | Gln | Ala | |
| | | | | 85 | | | | | 90 | | | | | 95 | | |
| cat | tta | aat | tca | ggg | gtt | att | ttc | tct | att | cat | cac | tta | gat | cac | agg | 336 |
| His | Leu | Asn | Ser | Gly | Val | Ile | Phe | Ser | Ile | His | His | Leu | Asp | His | Arg | |
| | | | 100 | | | | | 105 | | | | | 110 | | | |
| tat | ctg | gaa | ttg | gaa | agc | agc | ggt | cat | cga | aat | gaa | atc | agg | ttg | cat | 384 |
| Tyr | Leu | Glu | Leu | Glu | Ser | Ser | Gly | His | Arg | Asn | Glu | Ile | Arg | Leu | His | |
| | | 115 | | | | | 120 | | | | | 125 | | | | |
| tac | cgt | aca | ggc | agt | cat | cgc | tcc | cac | aca | gaa | gta | ttc | cca | tac | atc | 432 |
| Tyr | Arg | Thr | Gly | Ser | His | Arg | Ser | His | Thr | Glu | Val | Phe | Pro | Tyr | Ile | |
| | 130 | | | | | 135 | | | | | 140 | | | | | |
| ctg | gca | gac | gat | aag | tgg | cac | agg | ctt | tcc | tta | gca | atc | agt | gcc | tct | 480 |
| Leu | Ala | Asp | Asp | Lys | Trp | His | Arg | Leu | Ser | Leu | Ala | Ile | Ser | Ala | Ser | |
| 145 | | | | | 150 | | | | | 155 | | | | | 160 | |
| cac | ttg | att | tta | cac | gtg | gac | tgc | aat | aaa | atc | tat | gaa | aga | gtt | gtg | 528 |
| His | Leu | Ile | Leu | His | Val | Asp | Cys | Asn | Lys | Ile | Tyr | Glu | Arg | Val | Val | |
| | | | | 165 | | | | | 170 | | | | | 175 | | |
| gag | aag | ccc | ttc | atg | gac | tta | cct | gtg | ggt | aca | acc | ttt | tgg | cta | gga | 576 |
| Glu | Lys | Pro | Phe | Met | Asp | Leu | Pro | Val | Gly | Thr | Thr | Phe | Trp | Leu | Gly | |
| | | | 180 | | | | | 185 | | | | | 190 | | | |
| cag | agg | aat | aat | gca | cac | ggt | tat | ttt | aag | ggc | ata | atg | caa | gat | gtg | 624 |
| Gln | Arg | Asn | Asn | Ala | His | Gly | Tyr | Phe | Lys | Gly | Ile | Met | Gln | Asp | Val | |
| | | 195 | | | | | 200 | | | | | 205 | | | | |
| caa | tta | ctt | gtc | atg | cct | caa | gga | ttt | att | tct | cag | tgc | cca | gat | ctt | 672 |
| Gln | Leu | Leu | Val | Met | Pro | Gln | Gly | Phe | Ile | Ser | Gln | Cys | Pro | Asp | Leu | |
| | 210 | | | | | 215 | | | | | 220 | | | | | |
| aat | cgg | aca | tgc | cca | act | tgt | aat | gat | ttc | cat | gga | ctt | gtg | cag | aaa | 720 |

```
Asn Arg Thr Cys Pro Thr Cys Asn Asp Phe His Gly Leu Val Gln Lys
225                 230                 235                 240 att atg gaa ctg caa gac att tta gct aaa acg tca gct aag ctg tcg    768
Ile Met Glu Leu Gln Asp Ile Leu Ala Lys Thr Ser Ala Lys Leu Ser
                245                 250                 255 caa gct gag cag agg atg aac aag ttg gat cag tgc tat tgt gaa agg    816
Gln Ala Glu Gln Arg Met Asn Lys Leu Asp Gln Cys Tyr Cys Glu Arg
            260                 265                 270 acc tgc aca atg aaa ggc atg aca tac aga gaa ttt gaa tcc tgg aca    864
Thr Cys Thr Met Lys Gly Met Thr Tyr Arg Glu Phe Glu Ser Trp Thr
        275                 280                 285 gat ggt tgt aag aac tgc act tgc atg aat ggc act gtg cag tgt gaa    912
Asp Gly Cys Lys Asn Cys Thr Cys Met Asn Gly Thr Val Gln Cys Glu
    290                 295                 300 gct ttg att tgc tcc ctc tct gac tgt cca cct aat tct gcc ctg tca    960
Ala Leu Ile Cys Ser Leu Ser Asp Cys Pro Pro Asn Ser Ala Leu Ser
305                 310                 315                 320 tac gtg gat ggc aag tgc tgc aaa gaa tgt caa tcg gtg tgc ata ttt   1008
Tyr Val Asp Gly Lys Cys Cys Lys Glu Cys Gln Ser Val Cys Ile Phe
                325                 330                 335 gaa ggc aga acc tac ttt gaa gga caa aga gaa acg gtg tat tca agc   1056
Glu Gly Arg Thr Tyr Phe Glu Gly Gln Arg Glu Thr Val Tyr Ser Ser
            340                 345                 350 tca ggg gac tgt gtt ctg ttt gag tgc aag gac cac aaa atg cag cgt   1104
Ser Gly Asp Cys Val Leu Phe Glu Cys Lys Asp His Lys Met Gln Arg
        355                 360                 365 att cca aaa gac agt tgt gca act ttg aac tgc ccg gaa tct caa cag   1152
Ile Pro Lys Asp Ser Cys Ala Thr Leu Asn Cys Pro Glu Ser Gln Gln
    370                 375                 380 atc cca tta tct cac agt tgc tgc aaa atc tgt aaa ggc cat gac ttt   1200
Ile Pro Leu Ser His Ser Cys Cys Lys Ile Cys Lys Gly His Asp Phe
385                 390                 395                 400 tgc act gaa gga cat aac tgt atg gag cat tct gtc tgc cga aac cta   1248
Cys Thr Glu Gly His Asn Cys Met Glu His Ser Val Cys Arg Asn Leu
                405                 410                 415 gat gac aga gct gtc tgt agc tgc cga gat ggc ttc cgg gcc ctt cgg   1296
Asp Asp Arg Ala Val Cys Ser Cys Arg Asp Gly Phe Arg Ala Leu Arg
            420                 425                 430 gag gac aat gcc tac tgt gaa gat gtt gat gag tgt gcc gag ggg cag   1344
Glu Asp Asn Ala Tyr Cys Glu Asp Val Asp Glu Cys Ala Glu Gly Gln
        435                 440                 445 cac tac tgt cgg gag aac acc atg tgt gta aat aca cca gga tcc ttc   1392
His Tyr Cys Arg Glu Asn Thr Met Cys Val Asn Thr Pro Gly Ser Phe
    450                 455                 460 atg tgc atc tgc aaa aca gga tat ata cgc att gat gac tat tca tgt   1440
Met Cys Ile Cys Lys Thr Gly Tyr Ile Arg Ile Asp Asp Tyr Ser Cys
465                 470                 475                 480 aca gag cac gat gaa tgt gta aca aac cag cac aac tgt gat gaa aat   1488
Thr Glu His Asp Glu Cys Val Thr Asn Gln His Asn Cys Asp Glu Asn
                485                 490                 495 gcg cta tgt ttc aac acg gtg ggt ggg cac aac tgt gtc tgc aag ctg   1536
Ala Leu Cys Phe Asn Thr Val Gly Gly His Asn Cys Val Cys Lys Leu
            500                 505                 510 ggt tac aca gga aat ggg acg gtg tgt aaa gca ttt tgc aaa gat ggg   1584
Gly Tyr Thr Gly Asn Gly Thr Val Cys Lys Ala Phe Cys Lys Asp Gly
        515                 520                 525 tgc agg aat gga gga gcc tgt att gct tcc aac gtg tgt gcc tgc cca   1632
Cys Arg Asn Gly Gly Ala Cys Ile Ala Ser Asn Val Cys Ala Cys Pro
    530                 535                 540
```

-continued

```
caa ggc ttc act ggc ccc agc tgt gaa act gac att gat gaa tgc tct       1680
Gln Gly Phe Thr Gly Pro Ser Cys Glu Thr Asp Ile Asp Glu Cys Ser
545                 550                 555                 560 gat ggc ttt gtg cag tgt gac agc cgt gct aat tgc atc aat ctg cca       1728
Asp Gly Phe Val Gln Cys Asp Ser Arg Ala Asn Cys Ile Asn Leu Pro
                565                 570                 575 ggg tgg tac cac tgt gaa tgc agg gat ggc tac cat gac aat ggg atg       1776
Gly Trp Tyr His Cys Glu Cys Arg Asp Gly Tyr His Asp Asn Gly Met
            580                 585                 590 ttt tca cca agt gga gaa tcc tgt gaa gac att gat gaa tgt gca act       1824
Phe Ser Pro Ser Gly Glu Ser Cys Glu Asp Ile Asp Glu Cys Ala Thr
        595                 600                 605 gga agg cat agc tgt gcc aat gac act gtt tgc ttt aac ctg gat ggt       1872
Gly Arg His Ser Cys Ala Asn Asp Thr Val Cys Phe Asn Leu Asp Gly
    610                 615                 620 ggg tat gac tgt cga tgt cca cat ggc aag aac tgc aca gga gac tgt       1920
Gly Tyr Asp Cys Arg Cys Pro His Gly Lys Asn Cys Thr Gly Asp Cys
625                 630                 635                 640 atc cat gaa gac aaa atc aag cac aat ggt cag att tgg gtg ctg gag       1968
Ile His Glu Asp Lys Ile Lys His Asn Gly Gln Ile Trp Val Leu Glu
                645                 650                 655 aac gac aga tgc tct gtc tgc tca tgc cag agt gga tac gtg atg tgc       2016
Asn Asp Arg Cys Ser Val Cys Ser Cys Gln Ser Gly Tyr Val Met Cys
            660                 665                 670 cgg cga atg gtc tgt gac tgt gaa aat ccc act gtt gac ctc ttt tgc       2064
Arg Arg Met Val Cys Asp Cys Glu Asn Pro Thr Val Asp Leu Phe Cys
        675                 680                 685 tgt cct gag tgt gac cca agg ctc agc agt caa tgt tta cat cag agt       2112
Cys Pro Glu Cys Asp Pro Arg Leu Ser Ser Gln Cys Leu His Gln Ser
    690                 695                 700 ggg gag ctt tcc tac aac agt ggt gac tcc tgg ata caa aac tgt cag       2160
Gly Glu Leu Ser Tyr Asn Ser Gly Asp Ser Trp Ile Gln Asn Cys Gln
705                 710                 715                 720 cag tgt cgc tgc ttg caa gga gag gtt gac tgt tgg ccc tta ccg tgc       2208
Gln Cys Arg Cys Leu Gln Gly Glu Val Asp Cys Trp Pro Leu Pro Cys
                725                 730                 735 cca gag gta gac tgt gag ttc agt gtc ctc cct gag aat gag tgc tgc       2256
Pro Glu Val Asp Cys Glu Phe Ser Val Leu Pro Glu Asn Glu Cys Cys
            740                 745                 750 cca cgc tgt gtc act gac ccc tgc caa gcg gac acc atc cgt aat gac       2304
Pro Arg Cys Val Thr Asp Pro Cys Gln Ala Asp Thr Ile Arg Asn Asp
        755                 760                 765 atc acc aaa acc tgc ctg gat gaa acc aat gtt gtt cgc ttc act gga       2352
Ile Thr Lys Thr Cys Leu Asp Glu Thr Asn Val Val Arg Phe Thr Gly
    770                 775                 780 tct tct tgg att aag cat ggc aca gag tgc aca ctc tgc caa tgt aag       2400
Ser Ser Trp Ile Lys His Gly Thr Glu Cys Thr Leu Cys Gln Cys Lys
785                 790                 795                 800 aat ggc cac gtc tgt tgc tca gtg gat cca cag tgc ctt cag gaa ctg       2448
Asn Gly His Val Cys Cys Ser Val Asp Pro Gln Cys Leu Gln Glu Leu
                805                 810                 815 tga ca                                                                 2453
```

<210> SEQ ID NO 14
<211> LENGTH: 816
<212> TYPE: PRT
<213> ORGANISM: Gallus gallus

<400> SEQUENCE: 14

Met Glu Ser Gly Cys Gly Leu Gly Thr Leu Cys Leu Leu Leu Cys Leu

-continued

```
1               5              10              15
Gly Pro Val Val Gly Phe Gly Val Asp Pro Ser Leu Gln Ile Asp Val
                20                  25                  30

Leu Ser Glu Leu Gly Leu Pro Gly Tyr Ala Ala Gly Val Arg Gln Val
                35                  40                  45

Pro Gly Leu His Asn Gly Ser Lys Ala Phe Leu Phe Pro Asp Thr Ser
                50                  55                  60

Arg Ser Val Lys Ala Ser Pro Glu Thr Ala Glu Ile Phe Phe Gln Lys
65                  70                  75                  80

Leu Arg Asn Lys Tyr Glu Phe Thr Ile Leu Val Thr Leu Lys Gln Ala
                85                  90                  95

His Leu Asn Ser Gly Val Ile Phe Ser Ile His His Leu Asp His Arg
                100                 105                 110

Tyr Leu Glu Leu Glu Ser Ser Gly His Arg Asn Glu Ile Arg Leu His
                115                 120                 125

Tyr Arg Thr Gly Ser His Arg Ser His Thr Glu Val Phe Pro Tyr Ile
                130                 135                 140

Leu Ala Asp Asp Lys Trp His Arg Leu Ser Leu Ala Ile Ser Ala Ser
145                 150                 155                 160

His Leu Ile Leu His Val Asp Cys Asn Lys Ile Tyr Glu Arg Val Val
                165                 170                 175

Glu Lys Pro Phe Met Asp Leu Pro Val Gly Thr Thr Phe Trp Leu Gly
                180                 185                 190

Gln Arg Asn Asn Ala His Gly Tyr Phe Lys Gly Ile Met Gln Asp Val
                195                 200                 205

Gln Leu Leu Val Met Pro Gln Gly Phe Ile Ser Gln Cys Pro Asp Leu
                210                 215                 220

Asn Arg Thr Cys Pro Thr Cys Asn Asp Phe His Gly Leu Val Gln Lys
225                 230                 235                 240

Ile Met Glu Leu Gln Asp Ile Leu Ala Lys Thr Ser Ala Lys Leu Ser
                245                 250                 255

Gln Ala Glu Gln Arg Met Asn Lys Leu Asp Gln Cys Tyr Cys Glu Arg
                260                 265                 270

Thr Cys Thr Met Lys Gly Met Thr Tyr Arg Glu Phe Glu Ser Trp Thr
                275                 280                 285

Asp Gly Cys Lys Asn Cys Thr Cys Met Asn Gly Thr Val Gln Cys Glu
                290                 295                 300

Ala Leu Ile Cys Ser Leu Ser Asp Cys Pro Pro Asn Ser Ala Leu Ser
305                 310                 315                 320

Tyr Val Asp Gly Lys Cys Cys Lys Glu Cys Gln Ser Val Cys Ile Phe
                325                 330                 335

Glu Gly Arg Thr Tyr Phe Glu Gly Gln Arg Glu Thr Val Tyr Ser Ser
                340                 345                 350

Ser Gly Asp Cys Val Leu Phe Glu Cys Lys Asp His Lys Met Gln Arg
                355                 360                 365

Ile Pro Lys Asp Ser Cys Ala Thr Leu Asn Cys Pro Glu Ser Gln Gln
                370                 375                 380

Ile Pro Leu Ser His Ser Cys Cys Lys Ile Cys Lys Gly His Asp Phe
385                 390                 395                 400

Cys Thr Glu Gly His Asn Cys Met Glu His Ser Val Cys Arg Asn Leu
                405                 410                 415

Asp Asp Arg Ala Val Cys Ser Cys Arg Asp Gly Phe Arg Ala Leu Arg
                420                 425                 430
```

```
Glu Asp Asn Ala Tyr Cys Glu Asp Val Asp Glu Cys Ala Glu Gly Gln
            435                 440                 445

His Tyr Cys Arg Glu Asn Thr Met Cys Val Asn Thr Pro Gly Ser Phe
        450                 455                 460

Met Cys Ile Cys Lys Thr Gly Tyr Ile Arg Ile Asp Asp Tyr Ser Cys
465                 470                 475                 480

Thr Glu His Asp Glu Cys Val Thr Asn Gln His Asn Cys Asp Glu Asn
                485                 490                 495

Ala Leu Cys Phe Asn Thr Val Gly His Asn Cys Val Cys Lys Leu
            500                 505                 510

Gly Tyr Thr Gly Asn Gly Thr Val Cys Lys Ala Phe Cys Lys Asp Gly
        515                 520                 525

Cys Arg Asn Gly Gly Ala Cys Ile Ala Ser Asn Val Cys Ala Cys Pro
530                 535                 540

Gln Gly Phe Thr Gly Pro Ser Cys Glu Thr Asp Ile Asp Glu Cys Ser
545                 550                 555                 560

Asp Gly Phe Val Gln Cys Asp Ser Arg Ala Asn Cys Ile Asn Leu Pro
                565                 570                 575

Gly Trp Tyr His Cys Glu Cys Arg Asp Gly Tyr His Asp Asn Gly Met
            580                 585                 590

Phe Ser Pro Ser Gly Glu Ser Cys Glu Asp Ile Asp Glu Cys Ala Thr
        595                 600                 605

Gly Arg His Ser Cys Ala Asn Asp Thr Val Cys Phe Asn Leu Asp Gly
610                 615                 620

Gly Tyr Asp Cys Arg Cys Pro His Gly Lys Asn Cys Thr Gly Asp Cys
625                 630                 635                 640

Ile His Glu Asp Lys Ile Lys His Asn Gly Gln Ile Trp Val Leu Glu
                645                 650                 655

Asn Asp Arg Cys Ser Val Cys Ser Cys Gln Ser Gly Tyr Val Met Cys
            660                 665                 670

Arg Arg Met Val Cys Asp Cys Glu Asn Pro Thr Val Asp Leu Phe Cys
        675                 680                 685

Cys Pro Glu Cys Asp Pro Arg Leu Ser Ser Gln Cys Leu His Gln Ser
690                 695                 700

Gly Glu Leu Ser Tyr Asn Ser Gly Asp Ser Trp Ile Gln Asn Cys Gln
705                 710                 715                 720

Gln Cys Arg Cys Leu Gln Gly Glu Val Asp Cys Trp Pro Leu Pro Cys
                725                 730                 735

Pro Glu Val Asp Cys Glu Phe Ser Val Leu Pro Glu Asn Glu Cys Cys
            740                 745                 750

Pro Arg Cys Val Thr Asp Pro Cys Gln Ala Asp Thr Ile Arg Asn Asp
        755                 760                 765

Ile Thr Lys Thr Cys Leu Asp Glu Thr Asn Val Val Arg Phe Thr Gly
770                 775                 780

Ser Ser Trp Ile Lys His Gly Thr Glu Cys Thr Leu Cys Gln Cys Lys
785                 790                 795                 800

Asn Gly His Val Cys Cys Ser Val Asp Pro Gln Cys Leu Gln Glu Leu
                805                 810                 815

<210> SEQ ID NO 15
<211> LENGTH: 2520
<212> TYPE: DNA
<213> ORGANISM: Artificial Sequence
<220> FEATURE:
```

<223> OTHER INFORMATION: Synthetic signal peptide-NELL1-FLAG nucleic acid construct
<220> FEATURE:
<221> NAME/KEY: CDS
<222> LOCATION: (1)..(2520)

<400> SEQUENCE: 15

```
atg aaa ttc tta gtc aac gtt gca cta gtt ttt atg gtc gtg tac att      48
Met Lys Phe Leu Val Asn Val Ala Leu Val Phe Met Val Val Tyr Ile
1               5                   10                  15 tct tac atc tat gcg atg ccg atg gat gtg att tta gtt ttg tgg ttc      96
Ser Tyr Ile Tyr Ala Met Pro Met Asp Val Ile Leu Val Leu Trp Phe
            20                  25                  30 tgt gta tgc acc gcc agg aca gtg ttg ggc ttt ggg atg gac cct gac     144
Cys Val Cys Thr Ala Arg Thr Val Leu Gly Phe Gly Met Asp Pro Asp
        35                  40                  45 ctt cag ctg gac atc atc tca gag ctc gac ctg gtg aac acc acc ctg     192
Leu Gln Leu Asp Ile Ile Ser Glu Leu Asp Leu Val Asn Thr Thr Leu
    50                  55                  60 gga gtc acg cag gtg gct gga ctg cac aac gcc agt aaa gca ttt cta     240
Gly Val Thr Gln Val Ala Gly Leu His Asn Ala Ser Lys Ala Phe Leu
65                  70                  75                  80 ttt caa gat gta cag aga gag atc cat tcg gcc cct cac gtg agt gag     288
Phe Gln Asp Val Gln Arg Glu Ile His Ser Ala Pro His Val Ser Glu
                85                  90                  95 aag ctg atc cag cta ttc cgg aat aag agc gag ttc acc ttt ttg gct     336
Lys Leu Ile Gln Leu Phe Arg Asn Lys Ser Glu Phe Thr Phe Leu Ala
            100                 105                 110 aca gtg cag cag aaa cca tcc acc tca ggg gtg ata ctg tcc atc cgg     384
Thr Val Gln Gln Lys Pro Ser Thr Ser Gly Val Ile Leu Ser Ile Arg
        115                 120                 125 gag ctg gag cac agc tat ttt gaa ctg gag agc agt ggc cca aga gaa     432
Glu Leu Glu His Ser Tyr Phe Glu Leu Glu Ser Ser Gly Pro Arg Glu
    130                 135                 140 gag ata cgc tac cat tac ata cat ggt gga aag ccc agg act gag gcc     480
Glu Ile Arg Tyr His Tyr Ile His Gly Gly Lys Pro Arg Thr Glu Ala
145                 150                 155                 160 ctt ccc tac cgc atg gca gac gga caa tgg cac aag gtc gcg ctg tca     528
Leu Pro Tyr Arg Met Ala Asp Gly Gln Trp His Lys Val Ala Leu Ser
                165                 170                 175 gtg agc gcc tct cac ctc ctg ctc cac atc gac tgc aat agg att tac     576
Val Ser Ala Ser His Leu Leu Leu His Ile Asp Cys Asn Arg Ile Tyr
            180                 185                 190 gag cgt gtg ata gac cct ccg gag acc aac ctt cct cca gga agc aat     624
Glu Arg Val Ile Asp Pro Pro Glu Thr Asn Leu Pro Pro Gly Ser Asn
        195                 200                 205 ctg tgg ctt ggg caa cgt aac caa aag cat ggc ttt ttc aaa gga atc     672
Leu Trp Leu Gly Gln Arg Asn Gln Lys His Gly Phe Phe Lys Gly Ile
    210                 215                 220 atc caa gat ggt aag atc atc ttc atg ccg aat ggt ttc atc aca cag     720
Ile Gln Asp Gly Lys Ile Ile Phe Met Pro Asn Gly Phe Ile Thr Gln
225                 230                 235                 240 tgt ccc aac ctc aat cgc act tgc cca aca tgc agt gac ttc ctg agc     768
Cys Pro Asn Leu Asn Arg Thr Cys Pro Thr Cys Ser Asp Phe Leu Ser
                245                 250                 255 ctg gtt caa gga ata atg gat ttg caa gag ctt ttg gcc aag atg act     816
Leu Val Gln Gly Ile Met Asp Leu Gln Glu Leu Leu Ala Lys Met Thr
            260                 265                 270 gca aaa ctg aat tat gca gag acg aga ctt ggt caa ctg gaa aat tgc     864
Ala Lys Leu Asn Tyr Ala Glu Thr Arg Leu Gly Gln Leu Glu Asn Cys
        275                 280                 285
```

```
cac tgt gag aag acc tgc caa gtg agt ggg ctg ctc tac agg gac caa    912
His Cys Glu Lys Thr Cys Gln Val Ser Gly Leu Leu Tyr Arg Asp Gln
    290                 295                 300 gac tcc tgg gtg gat ggt gac aac tgt ggg aac tgc acg tgc aaa agt    960
Asp Ser Trp Val Asp Gly Asp Asn Cys Gly Asn Cys Thr Cys Lys Ser
305                 310                 315                 320 ggt gcc gtg gag tgc cgc agg atg tcc tgt ccc ccg ctc aac tgt tcc   1008
Gly Ala Val Glu Cys Arg Arg Met Ser Cys Pro Pro Leu Asn Cys Ser
                325                 330                 335 ccg gac tca ctt cct gtg cac att tcc ggc cag tgt tgt aaa gtt tgc   1056
Pro Asp Ser Leu Pro Val His Ile Ser Gly Gln Cys Cys Lys Val Cys
            340                 345                 350 aga cca aaa tgt atc tat gga gga aaa gtt ctt gct gag ggc cag cgg   1104
Arg Pro Lys Cys Ile Tyr Gly Gly Lys Val Leu Ala Glu Gly Gln Arg
        355                 360                 365 att tta acc aag acc tgc cgg gaa tgt cga ggt gga gtc ttg gta aaa   1152
Ile Leu Thr Lys Thr Cys Arg Glu Cys Arg Gly Gly Val Leu Val Lys
    370                 375                 380 atc aca gaa gct tgc cct cct ttg aac tgc tca gca aag gat cat att   1200
Ile Thr Glu Ala Cys Pro Pro Leu Asn Cys Ser Ala Lys Asp His Ile
385                 390                 395                 400 ctt cca gag aat cag tgc tgc agg gtc tgc cca ggt cat aac ttc tgt   1248
Leu Pro Glu Asn Gln Cys Cys Arg Val Cys Pro Gly His Asn Phe Cys
                405                 410                 415 gca gaa gca cct aag tgc gga gaa aac tcg gaa tgc aaa aat tgg aat   1296
Ala Glu Ala Pro Lys Cys Gly Glu Asn Ser Glu Cys Lys Asn Trp Asn
            420                 425                 430 aca aaa gca acc tgt gag tgc aag aat gga tac atc tct gtc cag ggc   1344
Thr Lys Ala Thr Cys Glu Cys Lys Asn Gly Tyr Ile Ser Val Gln Gly
        435                 440                 445 aac tct gca tac tgt gaa gat att gat gag tgt gca gct aaa atg cac   1392
Asn Ser Ala Tyr Cys Glu Asp Ile Asp Glu Cys Ala Ala Lys Met His
    450                 455                 460 tat tgt cat gcc aac acc gtg tgt gtc aac ttg ccg ggg ttg tat cgc   1440
Tyr Cys His Ala Asn Thr Val Cys Val Asn Leu Pro Gly Leu Tyr Arg
465                 470                 475                 480 tgt gac tgc gtc cca ggg tac atc cgt gtg gat gac ttc tct tgt acg   1488
Cys Asp Cys Val Pro Gly Tyr Ile Arg Val Asp Asp Phe Ser Cys Thr
                485                 490                 495 gag cat gat gat tgt ggc agc gga caa cac aac tgc gac aaa aat gcc   1536
Glu His Asp Asp Cys Gly Ser Gly Gln His Asn Cys Asp Lys Asn Ala
            500                 505                 510 atc tgt acc aac aca gtc cag gga cac agc tgc acc tgc cag ccg ggt   1584
Ile Cys Thr Asn Thr Val Gln Gly His Ser Cys Thr Cys Gln Pro Gly
        515                 520                 525 tac gtg gga aat ggc acc atc tgc aaa gca ttc tgt gaa gag ggt tgc   1632
Tyr Val Gly Asn Gly Thr Ile Cys Lys Ala Phe Cys Glu Glu Gly Cys
    530                 535                 540 aga tac gga ggt acc tgt gtg gct cct aac aag tgt gtc tgt cct tct   1680
Arg Tyr Gly Gly Thr Cys Val Ala Pro Asn Lys Cys Val Cys Pro Ser
545                 550                 555                 560 gga ttc acg gga agc cac tgt gag aaa gat att gat gaa tgc gca gag   1728
Gly Phe Thr Gly Ser His Cys Glu Lys Asp Ile Asp Glu Cys Ala Glu
                565                 570                 575 gga ttc gtt gaa tgc cac aac tac tcc cgc tgt gtt aac ctg cca ggg   1776
Gly Phe Val Glu Cys His Asn Tyr Ser Arg Cys Val Asn Leu Pro Gly
            580                 585                 590 tgg tac cac tgt gag tgc aga agc ggt ttc cat gac gat ggg acc tac   1824
Trp Tyr His Cys Glu Cys Arg Ser Gly Phe His Asp Asp Gly Thr Tyr
```

```
                595                 600                 605
tca ctg tcc ggg gag tcc tgc att gat atc gat gaa tgt gcc tta aga      1872
Ser Leu Ser Gly Glu Ser Cys Ile Asp Ile Asp Glu Cys Ala Leu Arg
    610                 615                 620 act cac act tgt tgg aat gac tct gcc tgc atc aac tta gca gga gga      1920
Thr His Thr Cys Trp Asn Asp Ser Ala Cys Ile Asn Leu Ala Gly Gly
625                 630                 635                 640 ttt gac tgc ctg tgt ccc tct ggg ccc tcc tgc tct ggt gac tgt ccc      1968
Phe Asp Cys Leu Cys Pro Ser Gly Pro Ser Cys Ser Gly Asp Cys Pro
                645                 650                 655 cac gaa gga ggg ctg aag cat aat ggg cag gtg tgg att ctg aga gaa      2016
His Glu Gly Gly Leu Lys His Asn Gly Gln Val Trp Ile Leu Arg Glu
            660                 665                 670 gac agg tgt tca gtc tgt tcc tgc aag gat ggg aag ata ttc tgc cgg      2064
Asp Arg Cys Ser Val Cys Ser Cys Lys Asp Gly Lys Ile Phe Cys Arg
        675                 680                 685 cgg aca gct tgt gat tgc cag aat cca aat gtt gac ctt ttt tgc tgc      2112
Arg Thr Ala Cys Asp Cys Gln Asn Pro Asn Val Asp Leu Phe Cys Cys
    690                 695                 700 cca gag tgc gat acc agg gtc acc agc caa tgt tta gat caa agt gga      2160
Pro Glu Cys Asp Thr Arg Val Thr Ser Gln Cys Leu Asp Gln Ser Gly
705                 710                 715                 720 cag aag ctc tat cga agt gga gac aac tgg acc cac agc tgc cag cag      2208
Gln Lys Leu Tyr Arg Ser Gly Asp Asn Trp Thr His Ser Cys Gln Gln
                725                 730                 735 tgc cga tgt ctg gaa gga gag gca gac tgc tgg cct ctg gct tgc cct      2256
Cys Arg Cys Leu Glu Gly Glu Ala Asp Cys Trp Pro Leu Ala Cys Pro
            740                 745                 750 agt ttg ggc tgt gaa tac aca gcc atg ttt gaa ggg gag tgt tgt ccc      2304
Ser Leu Gly Cys Glu Tyr Thr Ala Met Phe Glu Gly Glu Cys Cys Pro
        755                 760                 765 cga tgt gtc agt gac ccc tgc ctg gct ggt aat att gcc tat gac atc      2352
Arg Cys Val Ser Asp Pro Cys Leu Ala Gly Asn Ile Ala Tyr Asp Ile
    770                 775                 780 aga aaa act tgc ctg gac agc ttt ggt gtt tcg agg ctg agc gga gcc      2400
Arg Lys Thr Cys Leu Asp Ser Phe Gly Val Ser Arg Leu Ser Gly Ala
785                 790                 795                 800 gtg tgg aca atg gct gga tct cct tgt aca acc tgc aaa tgc aag aat      2448
Val Trp Thr Met Ala Gly Ser Pro Cys Thr Thr Cys Lys Cys Lys Asn
                805                 810                 815 ggg aga gtc tgc tgc tct gtg gat ctg gag tgt att gag aat aac tga      2496
Gly Arg Val Cys Cys Ser Val Asp Leu Glu Cys Ile Glu Asn Asn
            820                 825                 830 gac tac aag gac gac gat gac aag                                      2520
Asp Tyr Lys Asp Asp Asp Asp Lys
        835

<210> SEQ ID NO 16
<211> LENGTH: 839
<212> TYPE: PRT
<213> ORGANISM: Artificial Sequence
<220> FEATURE:
<223> OTHER INFORMATION: Synthetic signal peptide-NELL1-FLAG construct

<400> SEQUENCE: 16

Met Lys Phe Leu Val Asn Val Ala Leu Val Phe Met Val Val Tyr Ile
1               5                   10                  15

Ser Tyr Ile Tyr Ala Met Pro Met Asp Val Ile Leu Val Leu Trp Phe
            20                  25                  30

Cys Val Cys Thr Ala Arg Thr Val Leu Gly Phe Gly Met Asp Pro Asp
```

-continued

```
                    35                  40                  45
Leu Gln Leu Asp Ile Ile Ser Glu Leu Asp Leu Val Asn Thr Thr Leu
             50                  55                  60
Gly Val Thr Gln Val Ala Gly Leu His Asn Ala Ser Lys Ala Phe Leu
 65                  70                  75                  80
Phe Gln Asp Val Gln Arg Glu Ile His Ser Ala Pro His Val Ser Glu
                 85                  90                  95
Lys Leu Ile Gln Leu Phe Arg Asn Lys Ser Glu Phe Thr Phe Leu Ala
                100                 105                 110
Thr Val Gln Gln Lys Pro Ser Thr Ser Gly Val Ile Leu Ser Ile Arg
            115                 120                 125
Glu Leu Glu His Ser Tyr Phe Glu Leu Glu Ser Ser Gly Pro Arg Glu
        130                 135                 140
Glu Ile Arg Tyr His Tyr Ile His Gly Gly Lys Pro Arg Thr Glu Ala
145                 150                 155                 160
Leu Pro Tyr Arg Met Ala Asp Gly Gln Trp His Lys Val Ala Leu Ser
                165                 170                 175
Val Ser Ala Ser His Leu Leu Leu His Ile Asp Cys Asn Arg Ile Tyr
            180                 185                 190
Glu Arg Val Ile Asp Pro Pro Glu Thr Asn Leu Pro Pro Gly Ser Asn
        195                 200                 205
Leu Trp Leu Gly Gln Arg Asn Gln Lys His Gly Phe Phe Lys Gly Ile
    210                 215                 220
Ile Gln Asp Gly Lys Ile Ile Phe Met Pro Asn Gly Phe Ile Thr Gln
225                 230                 235                 240
Cys Pro Asn Leu Asn Arg Thr Cys Pro Thr Cys Ser Asp Phe Leu Ser
                245                 250                 255
Leu Val Gln Gly Ile Met Asp Leu Gln Glu Leu Leu Ala Lys Met Thr
            260                 265                 270
Ala Lys Leu Asn Tyr Ala Glu Thr Arg Leu Gly Gln Leu Glu Asn Cys
        275                 280                 285
His Cys Glu Lys Thr Cys Gln Val Ser Gly Leu Leu Tyr Arg Asp Gln
    290                 295                 300
Asp Ser Trp Val Asp Gly Asp Asn Cys Gly Asn Cys Thr Cys Lys Ser
305                 310                 315                 320
Gly Ala Val Glu Cys Arg Arg Met Ser Cys Pro Pro Leu Asn Cys Ser
                325                 330                 335
Pro Asp Ser Leu Pro Val His Ile Ser Gly Gln Cys Cys Lys Val Cys
            340                 345                 350
Arg Pro Lys Cys Ile Tyr Gly Gly Lys Val Leu Ala Glu Gly Gln Arg
        355                 360                 365
Ile Leu Thr Lys Thr Cys Arg Glu Cys Arg Gly Gly Val Leu Val Lys
    370                 375                 380
Ile Thr Glu Ala Cys Pro Pro Leu Asn Cys Ser Ala Lys Asp His Ile
385                 390                 395                 400
Leu Pro Glu Asn Gln Cys Cys Arg Val Cys Pro Gly His Asn Phe Cys
                405                 410                 415
Ala Glu Ala Pro Lys Cys Gly Glu Asn Ser Glu Cys Lys Asn Trp Asn
            420                 425                 430
Thr Lys Ala Thr Cys Glu Cys Lys Asn Gly Tyr Ile Ser Val Gln Gly
        435                 440                 445
Asn Ser Ala Tyr Cys Glu Asp Ile Asp Glu Cys Ala Ala Lys Met His
    450                 455                 460
```

Tyr Cys His Ala Asn Thr Val Cys Val Asn Leu Pro Gly Leu Tyr Arg
465                 470                 475                 480

Cys Asp Cys Val Pro Gly Tyr Ile Arg Val Asp Asp Phe Ser Cys Thr
            485                 490                 495

Glu His Asp Asp Cys Gly Ser Gly Gln His Asn Cys Asp Lys Asn Ala
            500                 505                 510

Ile Cys Thr Asn Thr Val Gln Gly His Ser Cys Thr Cys Gln Pro Gly
        515                 520                 525

Tyr Val Gly Asn Gly Thr Ile Cys Lys Ala Phe Cys Glu Glu Gly Cys
    530                 535                 540

Arg Tyr Gly Gly Thr Cys Val Ala Pro Asn Lys Cys Val Cys Pro Ser
545                 550                 555                 560

Gly Phe Thr Gly Ser His Cys Glu Lys Asp Ile Asp Glu Cys Ala Glu
                565                 570                 575

Gly Phe Val Glu Cys His Asn Tyr Ser Arg Cys Val Asn Leu Pro Gly
            580                 585                 590

Trp Tyr His Cys Glu Cys Arg Ser Gly Phe His Asp Asp Gly Thr Tyr
        595                 600                 605

Ser Leu Ser Gly Glu Ser Cys Ile Asp Ile Asp Glu Cys Ala Leu Arg
    610                 615                 620

Thr His Thr Cys Trp Asn Asp Ser Ala Cys Ile Asn Leu Ala Gly Gly
625                 630                 635                 640

Phe Asp Cys Leu Cys Pro Ser Gly Pro Ser Cys Ser Gly Asp Cys Pro
                645                 650                 655

His Glu Gly Gly Leu Lys His Asn Gly Gln Val Trp Ile Leu Arg Glu
            660                 665                 670

Asp Arg Cys Ser Val Cys Ser Cys Lys Asp Gly Lys Ile Phe Cys Arg
        675                 680                 685

Arg Thr Ala Cys Asp Cys Gln Asn Pro Asn Val Asp Leu Phe Cys Cys
690                 695                 700

Pro Glu Cys Asp Thr Arg Val Thr Ser Gln Cys Leu Asp Gln Ser Gly
705                 710                 715                 720

Gln Lys Leu Tyr Arg Ser Gly Asp Asn Trp Thr His Ser Cys Gln Gln
                725                 730                 735

Cys Arg Cys Leu Glu Gly Glu Ala Asp Cys Trp Pro Leu Ala Cys Pro
            740                 745                 750

Ser Leu Gly Cys Glu Tyr Thr Ala Met Phe Glu Gly Glu Cys Cys Pro
        755                 760                 765

Arg Cys Val Ser Asp Pro Cys Leu Ala Gly Asn Ile Ala Tyr Asp Ile
    770                 775                 780

Arg Lys Thr Cys Leu Asp Ser Phe Gly Val Ser Arg Leu Ser Gly Ala
785                 790                 795                 800

Val Trp Thr Met Ala Gly Ser Pro Cys Thr Thr Cys Lys Cys Lys Asn
                805                 810                 815

Gly Arg Val Cys Cys Ser Val Asp Leu Glu Cys Ile Glu Asn Asn Asp
            820                 825                 830

Tyr Lys Asp Asp Asp Asp Lys
        835

<210> SEQ ID NO 17
<211> LENGTH: 20
<212> TYPE: PRT
<213> ORGANISM: Artificial Sequence
<220> FEATURE:

-continued

```
<223> OTHER INFORMATION: Synthetic signal peptide

<400> SEQUENCE: 17

Met Tyr Arg Met Gln Leu Leu Ser Cys Ile Ala Leu Ser Leu Ala Leu
1               5                   10                  15

Val Thr Asn Ser
            20

<210> SEQ ID NO 18
<211> LENGTH: 19
<212> TYPE: PRT
<213> ORGANISM: Artificial Sequence
<220> FEATURE:
<223> OTHER INFORMATION: Synthetic peptide

<400> SEQUENCE: 18

Met Pro His His His His His His Gly Gly Gly Asp Asp Asp Asp Lys
1               5                   10                  15

Asp Pro Met
```

EXPRESSION SYSTEM OF NELL PEPTIDE

CROSS-REFERENCE TO RELATED APPLICATIONS

This application is a continuation-in-part of U.S. application Ser. No. 10/544,553, filed May 15, 2006 now U.S. Pat. No. 7,544,486, which is a U.S. National Phase of PCT application PCT/US2004/003808, filed on Feb. 9, 2004, the teachings of which are incorporated hereto by reference in their entirety. This application is also a continuation-in-part of PCT/US2006/005473, filed on Feb. 16, 2006, the teachings of which are incorporated hereto by reference in their entirety.

STATEMENT AS TO RIGHTS TO INVENTIONS MADE UNDER FEDERALLY SPONSORED RESEARCH AND DEVELOPMENT

This invention was made with Government support under Grant No. DE000422 and DE014649 awarded by the National Institutes of Health. The Government of the United States of America has certain rights in this invention.

FIELD OF THE INVENTION

The invention generally relates to methods for the expression and purification of a NELL peptide or a related agent.

BACKGROUND OF THE INVENTION

Growth factors are substances, such as peptides, which affect the growth and differentiation of defined populations of cells in vivo or in vitro.

Bone formation occurs during development of long bones (endochondral bone formation) and flat bones (intramembranous bone formation). Further, bone formation occurs during bone remodeling which occurs continuously in adult life in order to preserve the integrity of the skeleton. Finally, bone formation occurs during bone repair, such as when bone wounds occur in a fracture or surgical situation, for example. While separate bone formation mechanisms are thought to be involved in the embryological development of long and flat bones and repair is thought to involve intramembranous bone formation.

Bone formation by either mechanism involves the activity of osteoblasts, which are regulated by growth factors. Osteoblasts are derived from a pool of marrow stromal cells (also known as mesenchymal stem cells; MSC). These cells are present in a variety of tissues and are prevalent in bone marrow stroma. MSC are pluripotent and can differentiate into a variety of cell types including osteoblasts, chondrocytes, fibroblasts, myocytes, and adipocytes. Growth factors are thought to impact osteogenic cell proliferation, differentiation and osteoblast mineralization, each of which impacts bone formation.

Autogenous bone has been used, such to repair bone in patients with craniosynostosis and cleft grafting, for example. Craniosynostosis (CS), the premature closure of cranial sutures, affects 1 in 3,000 infants and therefore is one of the most common human congenital craniofacial deformities. Premature suture closure results in cranial dimorphism, which can need surgical correction. Premature suture closure in human CS can occur by two possibly distinct processes: calvarial overgrowth and bony fusion. Recently, fibroblast growth factor 2 (FGF2) and fibroblast growth factor receptor 1 (FGFR1) have been implicated in premature cranial suture fusion via CBFA1-mediated pathways (8). Missense mutation of CBFA1 is linked to cleidocranial dysplasia, manifested as delayed suture closure.

Autologous bone grafting procedures have been performed utilizing autogenous bone, such as from the iliac crest or calvaria. These donor sites are not without associated morbidity including pain, gait disturbance, thigh paresthesia for iliac crest donor sites, and infection, neurologic deficits, and hematomas for calvarial grafts. Further, donor sites can have limited volume and can contribute to increased surgical time and hospital stay.

Alloplastic grafting materials have also been utilized, and growth factors have been tested in animal models. For example, bFGF has shown potential for use in bone regeneration and repair. Another family of osteogenic growth factors have been described as bone morphogenic protein (BMP). Specifically, BMP-2 recombinant protein has been demonstrated to regenerate mandibular continuity defects and cleft palate defects with results equal to or better than autogenous particulate bone and marrow. BMPs and other osteogenic factors have been studied for use in clinical applications. However, the cost of using minimally effective dosages of BMP has been a limiting factor in clinical use.

Spinal fusion is a surgical technique in which one more of the vertebrae of the spine are united together so that motion no longer occurs between them. Indications include: treatment of a fractured (broken) vertebra, correction of deformity, elimination of pain from motion, treatment of instability, and treatment of some cervical disc herniations. The surgery can involve placement of a bone graft between the vertebrae to obtain a solid union between the vertebrae. The procedure also can involve supplemental treatments including the placement of plates, screws, cages, and recently bone morphogenic protein 2 and 7 to assist in stabilizing and healing the bone graft. Autogenous bone grafting has been the clinically preferred method, and yet has about a 30-50% failure rate. Autogenous bone grafting is a separate surgery and also carries significant morbidity.

Cartilage is a type of dense connective tissue. It is composed of chondrocytes which are dispersed in a firm gel-like matrix. Cartilage is avascular (contains no blood vessels) and nutrients are diffused through the matrix. Cartilage is found in the joints, the rib cage, the ear, the nose, in the throat and between intervertebral disks. There are three main types of cartilage: hyaline (e.g., costal cartilages, the cartilages of the nose, trachea, and bronchi, and the articular cartilages of joints), elastic (e.g., external ear, external auditory meatus, part of the Eustachian tube, epiglottis, and in some of the laryngeal cartilages) and fibrocartilage [e.g. meniscus (e.g., wrist triangular fibrocartilage complex, knee meniscus), intervertebral discs, temporomandibular joint disc, the pubic symphysis, and in some tendons and ligaments at their attachment to bones. One of the main purposes of cartilage is to provide a framework upon which bone deposition could begin (i.e., during endochondral ossification). Another important purpose of cartilage is to provide smooth surfaces for the movement of articulating bones. For example, articular cartilage, most notably that which is found in the knee joint, is generally characterized by very low friction, high wear resistance, and poor regenerative qualities. It is responsible for much of the compressive resistance and load bearing qualities of the knee joint and, without it, walking is painful to impossible. Yet another important purpose of cartilage is to provide, firm, yet flexible support (e.g., nasal cartilage, spinal discs, tracheal cartilage, knee meniscus, bronchial cartilage). For instance, cartilage such as the meniscus plays a crucial role in joint stability, lubrication, and force transmission. Under a weight bearing load, the meniscus maintains the balanced position of the femur on the tibia and distributes the compressive forces by increasing the surface contact area, thereby decreasing the average stress two to three times. Additionally, the menisci interact with the joint fluid to produce a coefficient of friction that is five times as slick as ice on ice. In another example, the intervertebral disc has several important functions, including functioning as a spacer, as a shock absorber, and as a motion unit. The gelatinous central portion of the disc is called the nucleus pulposus. It is composed of 80-90% water. The solid portion of the nucleus is Type II collagen and non-aggregated proteoglycans. The outer ligamentous ring around the nucleus pulposus is called the annulus fibrosus, which hydraulically seals the nucleus, and allows intradiscal pressures to rise as the disc is loaded. The annulus has overlapping radial bands, not unlike the plies of a radial tire, and this allows torsional stresses to be distributed through the annulus under normal loading without rupture. The disc functions as a hydraulic cylinder. The annulus interacts with the nucleus. As the nucleus is pressurized, the annular fibers serve a containment function to prevent the nucleus from bulging or herniating.

Cartilage can be damaged by wear, injury or diseases. As we age, the water and protein content of the body's cartilage changes. This change results in weaker, more fragile and thin cartilage. Osteoarthritis is a common condition of cartilage failure that can lead to limited range of motion, bone damage and invariably, pain. Due to a combination of acute stress and chronic fatigue, osteoarthritis directly manifests itself in a wearing away of the articulating surface and, in extreme cases, bone can be exposed in the joint. In another example, loss of the protective stabilizing meniscus leads to increased joint laxity or abnormal motions that lead to joint instability. The excessive motion and narrowed contact area promotes early arthritic changes. At the cellular level, there is initially a loss of cells from the superficial layer of the articular cartilage followed by cartilage splitting, subsequent thinning and erosion occurs, and finally protrusion of the underlying raw bone. The earliest arthritic changes have been noted three weeks after loss of the entire meniscus. In yet another example, because both the discs and the joints that stack the vertebrae (facet joints) are partly composed of cartilage, these areas are subject to wear and tear over time (degenerative changes). As the inner nucleus dehydrates, the disc space narrows, and redundant annular ligaments bulge. With progressive nuclear dehydration, the annular fibers can crack and tear. Loss of normal soft tissue tension may allow the spinal segment to sublux (e.g. partial dislocation of the joint), leading to osteophyte formation (bone spurs), foraminal narrowing, mechanical instability, and pain. If the annular fibers stretch or rupture, allowing the pressurized nuclear material to bulge or herniate and compress neural tissues, pain and weakness may result. This is the condition called a pinched nerve, slipped disc, or herniated disc. Radiculopathy refers to nerve irritation caused by damage to the disc between the vertebrae. Mechanical dysfunction may also cause disc degeneration and pain (e.g. degenerative disc disease). For example, the disc may be damaged as the result of some trauma that overloads the capacity of the disc to withstand increased forces passing through it, and inner or outer portions of the annular fibers may tear. These torn fibers may be the focus for inflammatory response when they are subjected to increased stress, and may cause pain directly, or through the compensatory protective spasm of the deep paraspinal muscles.

There are several different repair options available for cartilage damage or failure.

Osteoarthritis is the second leading cause of disability in the elderly population in the United States. It is a degenerative disorder that generally starts off relatively mild and escalates with time and wear. For those patients experiencing mild to moderate symptoms, the disorder can be dealt with by several non-surgical treatments. The use of braces and drug therapies, such as anti-inflammatories (ex. diclofenac, ibuprofen, and naproxen), COX-2 selective inhibitors, hydrocortisone, glucosamine, and chondroitin sulfate, have been shown to alleviate the pain caused by cartilage deficiency and some claim they can slow the degenerative process.

Most surgical treatments for articular cartilage, short of total joint replacement, can be divided into various treatment groups. Treatments that remove the diseased and undermined cartilage with an aim to stop inflammation and pain include shaving (chondrectomy) and debridement. Another group of treatments consists of a range of abrasive procedures aimed at triggering cartilage production, such as drilling, microfracture surgery, chondroplasty, and spongialization. Abrasion, drilling, and microfracture originated 20 years ago. They rely on the phenomenon of spontaneous repair of the cartilage tissue following vascular injury to the subchondral plate of the bone. Laser assisted treatments, currently experimental, compose another category; they combine the removal of diseased cartilage with cartilage reshaping and also induce cartilage proliferation. Additional treatments include autologous cartilage implants (e.g., Carticel by Genzyme).

Other treatments that can be more applicable to meniscal cartilage include early surgical intervention and suture repair of torn structures or allograft meniscus transplantation in severe injury cases.

Although the overwhelming majority of patients with a herniated disc and sciatica heal without surgery, if surgery is indicated procedures include removal of the herniated disc with laminotomy (producing a small hole in the bone of the spine surrounding the spinal cord), laminectomy (removal of the bony wall adjacent to the nerve tissues), by needle technique through the skin (percutaneous discectomy), disc-dissolving procedures (chemonucleolysis), and others. For patients with mechanical pain syndrome, unresponsive to conservative treatment, and disabling to the individual's way of life, the problem can be addressed by spinal fusion, intradiscal electrothermal coagulation (or annuloplasty), posterior dynamic stabilization, artificial disc technologies, or still experimental disc regeneration therapies using various molecular based therapies delivered using proteins, peptides, gene therapies, or nucleotides. Although numerous methods have been described for treatment of cartilage problems, it is clear that many are artificial or mechanically based solutions that do not seek to recreate normal cartilage tissue biology. Therefore, there is a need for methods for stimulating cartilage formation.

Therefore, there is a need for compositions and methods to induce bone formation in bone development, disorders, or bone trauma.

Therefore, there is a need for compositions and methods to induce cartilage formation and regeneration.

SUMMARY OF THE INVENTION

The present invention is related to methods for the expression and purification of NELL1 and NELL2 proteins. The method includes:

providing a nucleic acid construct including at least a nucleic acid encoding at least a NELL peptide in frame with a nucleic acid encoding a secretory signal peptide;

transfecting a mammalian cell with said nucleic acid construct; and culturing said mammalian cell under conditions that permit expression of the NELL peptide.

In some embodiments, the mammalian cell is a Chinese hamster ovary cell. The method can further include collecting NELL peptide secreted from the cell line; and substantially purifying the NELL peptide. In some embodiments, the method can further include testing the activity of the NELL peptide to induce bone formation.

The NELL protein produced by the expression system described herein can be used alone or with other agents for bone or cartilage formation or regeneration. In some embodiments, the NELL protein described herein can be used to form a composition in any desirable formulation. Some examples of NELL protein compositions and formulations are described in U.S. patent Ser. No. 11/392,294, and PCT/US2006/005473, the teachings of which are incorporated hereto by reference in their entirety. In some embodiments, the composition or formulation can include a carrier, e.g., a pharmaceutically acceptable carrier. In some embodiments, a substrate can include cells and/or NELL1 peptide which can facilitate bone cartilage, disc, or other forms of tissue repair in the proximity of the implant.

In some embodiments, the invention includes methods of inducing osteogenic differentiation, osteoblastic mineralization and/or bone formation in a variety of clinical applications. The invention also includes methods of inducing chondrogenic differentiation and/or chondrogenic mineralization in a variety of clinical applications.

In some embodiments, this invention can provide a greater effect than known growth factors and/or can enhance the activity of other growth factors. Therefore, lower doses of each growth factor can be used for clinical applications. This is significant at least in that clinical treatments can be more affordable. Further this invention is advantageous at least in that NELL1 enhances osteogenic differentiation, osteoblastic mineralization and bone formation, which can improve the clinical rate and effectiveness of treatment with BMPs alone. This invention is also advantageous in that NELL1 enhances chondrogenic differentiation and/or chondrogenic mineralization which can improve the clinical rate and effectiveness of treatment with BMP alone.

Some examples of NELL protein compositions and formulations are described in U.S. patent Ser. No. 11/392,294, and PCT/US2006/005473, the teachings of which are incorporated hereto by reference in their entirety.

BRIEF DESCRIPTION OF THE DRAWINGS

FIGS. 2A-2D illustrate a signal peptide-NELL1-FLAG nucleic acid construct (SEQ ID NO: 15). Underlined amino acid sequences are derived from melittin signal peptide. The bond between Alanine and Proline is a putative cleavage site for secretion by High Five cells. The residues from RTV-LGFG (residues 38-44 of SEQ ID NO: 16) are derived from the mature protein of rat/human NELL1 protein.

FIGS. 3A-3D illustrate the products of extracellular expression of NELL1-FLAG FIG. 3A is a CBB-stained SDS-PAGE gel of UnoQ-eluate containing purified NELL1 peptide produced from high five cells in serum-free medium (Productivity: ca. 3 mg/L medium); FIG. 3B is a Western blotting using anti-FLAG antibody. FIG. 3C is a CBB-stained SDS-PAGE gel of UnoQ-eluate containing purified NELL1 peptide produced from COS7 cells in serum-free medium (Productivity: <0.1 mg/L medium). FIG. 3D is a Western blotting using anti-FLAG antibody.

FIGS. 4A-4C illustrate the production of NELL1 peptide (SEQ ID NO: 2) by a CHO expression system. FIG. 4A is the depiction of the nucleic acid sequence of the cDNA construct used in this example and amino acid sequences of three different signal peptides (residues 1-16 of SEQ ID NO: 2, residues 1-21 of SEQ ID NO: 8, and SEQ ID NO: 17, respectively). FIG. 4B is a Western blot with anti-c-myc antibody detecting secreting NELL1 from transfections with different constructs after immunoprecipitation using anti-c-myc agarose. FIG. 4C is a Western blot with anti-c-myc or mouse anti-human NELL1 antibodies detecting secreting NELL1 after immunoprecipitation using rabbit anti-human Nell-1 antibody-NHS activated sepharose.

DETAILED DESCRIPTION OF THE INVENTION

Figure 1A:
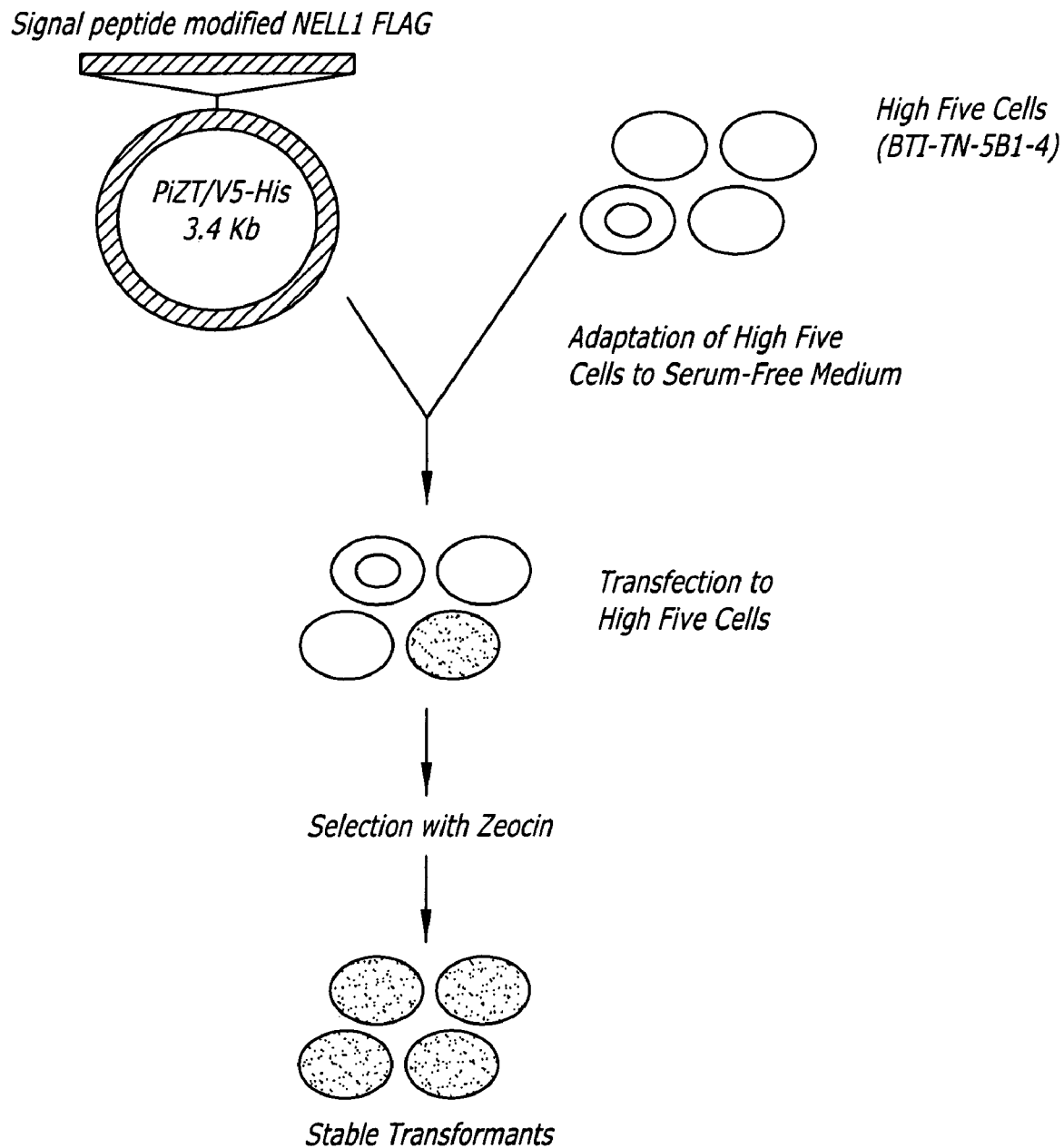
FIGS. 1A-1B show a flow diagram of one method of producing a NELL peptide.
Figure 1B:
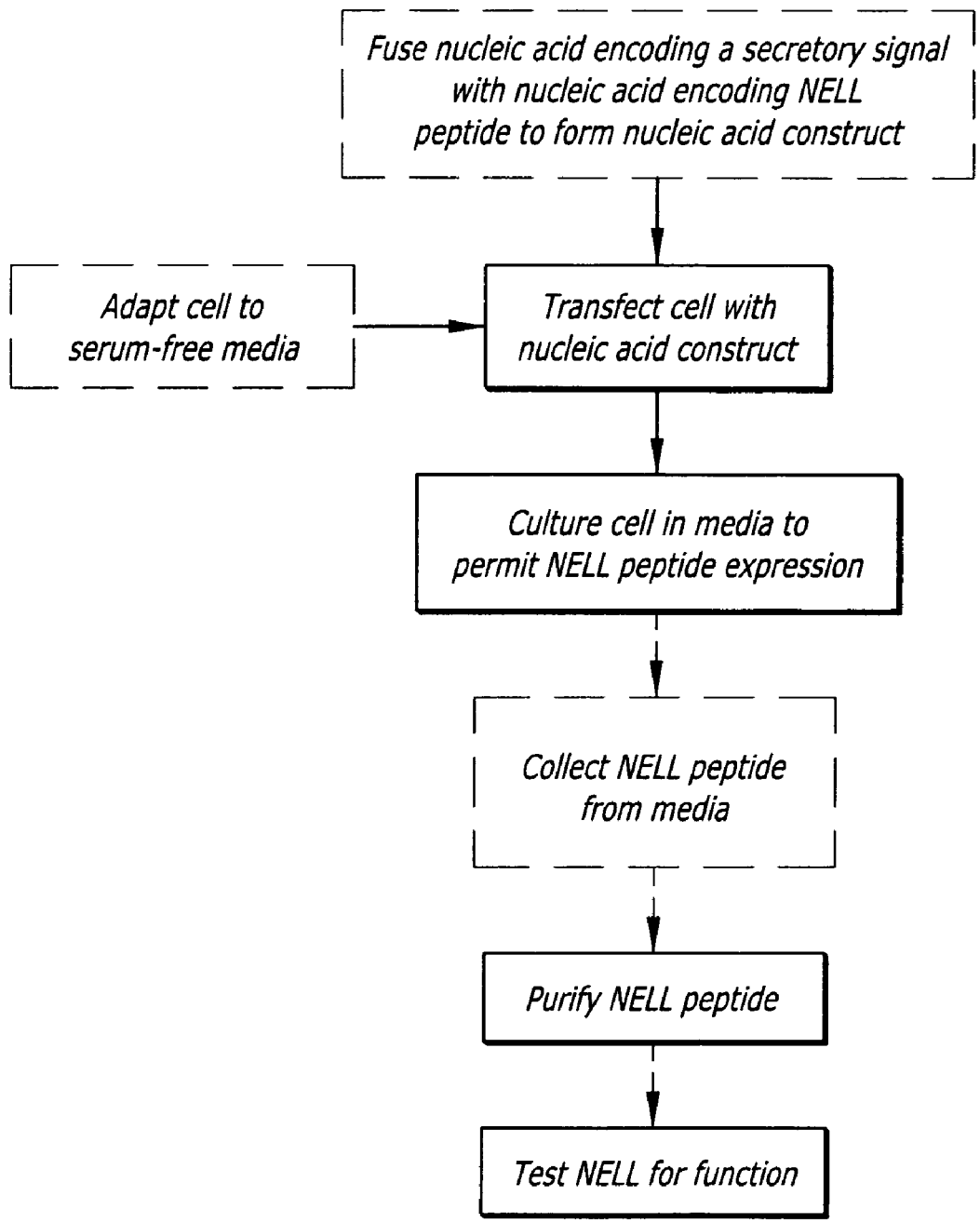

The present invention is related to methods for the expression and purification of NELL1 and NELL2 proteins. The method includes:

providing a nucleic acid construct including at least a nucleic acid encoding at least a NELL peptide in frame with a nucleic acid encoding a secretory signal peptide;

transfecting a mammalian cell with said nucleic acid construct; and culturing said mammalian cell under conditions that permit expression of the NELL peptide.

In some embodiments, the mammalian cell is a Chinese hamster ovary cell. The method can further include collecting NELL peptide secreted from the cell line; and substantially purifying the NELL peptide. In some embodiments, the method can further include testing the activity of the NELL peptide to induce bone formation.

The NELL protein produced by the expression system described herein can be used alone or with other agents for bone or cartilage formation or regeneration. In some embodiments, the NELL protein described herein can be used to form a composition in any desirable formulation. In some embodiments, the composition or formulation can include a carrier, e.g., a pharmaceutically acceptable carrier. In some embodiments, a substrate can include cells and/or NELL1 peptide which can facilitate bone cartilage, disc, or other forms of tissue repair in the proximity of the implant.

In some embodiments, the invention includes methods of inducing osteogenic differentiation, osteoblastic mineralization and/or bone formation in a variety of clinical applications. The invention also includes methods of inducing chondrogenic differentiation and/or condrogenic mineralization in a variety of clinical applications.

In some embodiments, this invention can provide a greater effect than known growth factors and/or can enhance the activity of other growth factors. Therefore, lower doses of each growth factor can be used for clinical applications. This is significant at least in that clinical treatments can be more affordable. Further this invention is advantageous at least in that NELL1 enhances osteogenic differentiation, osteoblastic mineralization and bone formation, which can improve the clinical rate and effectiveness of treatment with BMPs alone. This invention is also advantageous in that NELL1 enhances chondrogenic differentiation and/or chondrogenic mineralization which can improve the clinical rate and effectiveness of treatment with BMP alone.

Some examples of NELL protein compositions and formulations are described in U.S. patent Ser. No. 11/392,294, and PCT/US2006/005473, the teachings of which are incorporated hereto by reference in their entirety.

Definition

The terms "polypeptide", "peptide" and "protein" can be used interchangeably herein to refer to a polymer of amino acid residues. The terms can apply to amino acid polymers in which one or more amino acid residue is an artificial chemical analogue of a corresponding naturally occurring amino acid, as well as to naturally occurring amino acid polymers.

The term "antibody" can include various forms of modified or altered antibodies, such as an intact immunoglobulin, an Fv fragment containing only the light and heavy chain variable regions, an Fv fragment linked by a disulfide bond, a Fab or (Fab)'2 fragment containing the variable regions and parts of the constant regions, a single-chain antibody and the like. An antibody can include intact molecules as well as fragments thereof, such as, Fab and F(ab')$^{2'}$, and/or single-chain antibodies (e.g. scFv) which can bind an epitopic determinant. An antibody can be of animal (such as mouse or rat) or human origin or can be chimeric or humanized. Antibodies can be polyclonal or monoclonal antibodies ("mAb's"), such as monoclonal antibodies with specificity for a polypeptide encoded by a NELL1 or NELL2 protein.

The term "capture agent" can refer to molecules that specifically bind other molecules to form a binding complex such as antibody-antigen, lectin-carbohydrate, nucleic acid-nucleic acid, biotin-avidin, and the like.

The term "specifically binds" can refer to a biomolecule (e.g., protein, nucleic acid, antibody, etc.), refers to a binding reaction which is determinative of the presence biomolecule in heterogeneous population of molecules (e.g., proteins and other biologics). Thus, under designated conditions (e.g. immunoassay conditions in the case of an antibody or stringent hybridization conditions in the case of a nucleic acid), the specified ligand or antibody can bind to its particular "target" molecule and can not bind in a significant amount to other molecules present in the sample.

The terms "nucleic acid" or "oligonucleotide" can refer to at least two nucleotides covalently linked together. A nucleic acid of the present invention can be single-stranded or double stranded and can contain phosphodiester bonds, although in some cases, nucleic acid analogs can be included that can have alternate backbones, comprising, for example, phosphoramide, phosphorothioate, phosphorodithioate, omethylphophoroamidite linkages, and/or peptide nucleic acid backbones and linkages. Analog nucleic acids can have positive backbones and/or non-ribose backbones. Nucleic acids can also include one or more carbocyclic sugars. Modifications of the ribose-phosphate backbone can be done to facilitate the addition of additional moieties such as labels, or to increase the stability and half-life of such molecules in physiological environments, for example.

The term "specific hybridization" can refer to the binding, duplexing, or hybridizing of a nucleic acid molecule preferentially to a particular nucleotide sequence under stringent conditions, including conditions under which a probe can hybridize preferentially to its target subsequence, and can hybridize to a lesser extent to other sequences.

The terms "NELL1 cDNA" refer to SEQ ID NO:1, 3 and 5, and "NELL2 cDNA" can refer to SEQ ID NO:7, 9, 11 and 13.

NELL Peptides

NELL1 is a 810 aa (amino acid) peptide, distributed primarily in bone. In adults, NELL1 is expressed at high levels in craniofacial bone, and lower levels in long bone. Its role in osteoblast differentiation, bone formation and regeneration has been examined. NELL2 is a 816 aa peptide, distributed in neural cells and brain.

Human NELL1 gene includes at least 3 Cbfa1 response elements in the promoter region. Cbfa1 specifically binds to these response elements in the NELL1 promoter. NELL1 expression can be under the control of this transcription factors expressed endogenously at least in preosteoblasts, osteoblasts and hypertrophic chondrocytes in development and in adulthood. Cleidocranial disostosis is a developmental cranial defect thought to be caused at least in part by Cbfa disruption.

A NELL1 peptide is a protein which can be expressed by the NELL1 gene or cDNA and includes SEQ ID NO: 2, 4, and 6. The NELL1 peptide can include a NELL1 peptide fragment that retains the ability to induce osteogenic cell differentiation, osteoblast differentiation or bone formation. A NELL2 peptide is a protein which can be expressed by the NELL2 gene or cDNA and includes SEQ ID NO: 8, 10, 12 and 14. The NELL2 peptide can include NELL2 peptide fragments that retain similar activity to the full NELL2 peptide sequence.

The term "derivative" as used herein, refers to any chemical or biological compounds or materials derived from a NELL peptide, structural equivalents thereof, or conformational equivalents thereof. For example, such a derivative can include any pro-drug form, PEGylated form, or any other form of a NELL peptide that renders the NELL peptide more stable or to have a better osteophilicity or lipophilicity. In some embodiments, the derivative can be a NELL peptide attached to poly(ethylene glycol), a poly(amino acid), a hydrocarbyl short chain having C1-C20 carbons, or a biocompatible polymer. In some embodiments, the term "derivative" can include a NELL peptide mimetics. As used herein, the term "mimetic" refers to a peptide having at least one non-peptide bond in its backbone. A peptide bond is a chemical bond formed between the carboxylic acid group of an amino acid molecule and the amino group of another amino acid molecule.

Synthesis of mimetics of a peptide is well document in the art. The following describes an example of the basic procedure for the synthesis of a peptide, including a peptide mimetics:

Before the peptide synthesis starts, the amine terminus of the amino acid (starting material) can protected with FMOC (9-fluoromethyl carbamate) or other protective groups, and a solid support such as a Merrifield resin (free amines) is used as an initiator. Then, step (1) through step (3) reactions are performed and repeated until the desired peptide is obtained: (1) a free-amine is reacted with carboxyl terminus using carbodiimide chemistry, (2) the amino acid sequence is purified, and (3) the protecting group, e.g., the FMOC protecting group, is removed under mildly acidic conditions to yield a free amine. The peptide can then be cleaved from the resin to yield a free standing peptide or peptide mimetics.

In one embodiment, the method can include providing a nucleic acid sequence encoding a NELL peptide, such as NELL1 or NELL2 peptide, in frame with a nucleic acid sequence encoding a secretory signal peptide. In one embodiment, the secretory signal peptide can be a secretory signal peptide from a secreted bee protein. For example, the nucleic acid sequence can be selected from the group including, but not limited to a melittin signal sequence, drosphila immunoglobulin-binding protein signal sequence, equine interferon-gamma (eIFN-gamma) signal peptide, snake phospholipase A2 inhibitor signal peptide, human and/or chicken lysozyme signal peptide. For mammalian expression systems, a protrypsin leading sequence can also be used.

In one embodiment, the method can include transfecting an insect cell line with a nucleic acid construct encoding a NELL peptide; and culturing the insect cell line under conditions that permit expression and/or secretion of the NELL peptide.

For example, the cell line can be transfected transiently or stably with the nucleic acid construct encoding a NELL peptide.

Systems Expressing Nell Peptides

A NELL peptide can be expressed in any biological system. For example, a NELL peptide can be expressed in a bacterial system, a yeast system, a plant system, or animal system.

In some embodiments, a NELL peptide can be expressed in a cell free expression system well known to those in the art. For example, *E. coli* cell-free protein translation systems or wheat germ cell-free protein translation systems.

In some embodiments, a NELL peptide can be expressed in transgenic plant cell systems derived from tobacco, corn, rice, or soybean.

Such expression systems can include a carrier such as a viral carrier or viral vector, peptide carrier, or a short polymer molecule.

In some embodiments, a NELL peptide can be expressed in insect cells. The NELL1 and NELL2 peptides expressed in an insect system are functional forms of the protein.

COS7 cells can be used to produce NELL1 and NELL2 proteins at low levels, such as about 10 micrograms per litter medium, but require serum-containing medium for the expression. As for the signal peptides, NELL1 and NELL2 endogenous signal peptides permit expression in COS7 cells.

In one embodiment, the invention includes a method of expressing a functional NELL peptide, such as NELL1 or NELL2 peptide, using an insect cell line. In one embodiment, the insect cell can be a high five cell, Sf9 and other Sf cells.

In one embodiment, the method can include providing a nucleic acid sequence encoding a NELL peptide, such as NELL1 or NELL2 peptide. The nucleic acid sequence can be a cDNA or genomic DNA, encoding at least a functional portion of a NELL peptide. For example, the nucleic acid sequence can be selected from the group including, but not limited to human NELL1 (SEQ ID NO:1), rat NELL1 (SEQ ID NO:3), mouse NELL1 (SEQ ID NO:5), or human NELL2 (SEQ ID NO:7), rat NELL2 (SEQ ID NO:9), mouse NELL2 (SEQ ID NO:11), chicken NELL2 (SEQ ID NO:13). The nucleic acid sequence can also include sequences such as those with substantial sequence similarity, such as sequences having at least about 75% sequence similarity with any portion of the sequences listed above.

Further the nucleic acid can include an expression vector for expressing the nucleic acid sequence encoding a NELL peptide, such as NELL1 or NELL2 peptide. For example, the expression vector can be pIZT/V5-His (Invitrogen), and selective markers can also include blasticidin and neomycin.

Further, the nucleic acid sequence can also include additional nucleic acids which encode reporter products to monitor levels of gene expression, or encode peptide tags which can be visualized using known methods in the art to monitor levels of peptide expression. Additional sequences can be selected so as to not interfere with the expression of the nucleic acid, or the functionality of the expressed peptide product.

In one embodiment, the invention can include a nucleic acid construct for expressing a NELL peptide, such as NELL1 and/or NELL2 peptide in an insect cell. The nucleic acid sequence can be a cDNA or genomic DNA, encoding at least a functional portion of a NELL peptide. For example, the nucleic acid sequence can be selected from the group including, but not limited to human NELL1 (SEQ ID NO:1), rat NELL1 (SEQ ID NO:3), mouse NELL1 (SEQ ID NO:5), or human NELL2 (SEQ ID NO:7), rat NELL2 (SEQ ID NO:9), mouse NELL2 (SEQ ID NO:11), chicken NELL2 (SEQ ID NO:13). The nucleic acid sequence can also include sequences such as those with substantial sequence similarity, such as sequences having at least about 75% sequence similarity with any portion of the sequences listed above.

In one embodiment, the invention can include a nucleic acid construct for expressing a NELL peptide, such as NELL1 and/or NELL2 peptide in a mammalian cell such as a Chinese hamster ovary cell (CHO cell). The nucleic acid sequence can be a cDNA or genomic DNA, encoding at least a functional portion of a NELL peptide. For example, the nucleic acid sequence can be selected from the group including, but not limited to human NELL1 (SEQ ID NO:1), rat NELL1 (SEQ ID NO:3), mouse NELL1 (SEQ ID NO:5), or human NELL2 (SEQ ID NO:7), rat NELL2 (SEQ ID NO:9), mouse NELL2 (SEQ ID NO:11), chicken NELL2 (SEQ ID NO:13). The nucleic acid sequence can also include sequences such as those with substantial sequence similarity, such as sequences having at least about 75% sequence similarity with any portion of the sequences listed above.

In some embodiments, for production of NELL1 and/or NELL2 peptides in mammalian cells (e.g., CHO cells), the expressing system for NELL1 and/or NELL2 can include the nucleic acid or cDNA that expresses the endogenous signal peptide. In some embodiments, the expressing system for NELL1 and/or NELL2 peptides can include the nucleic acid or cDNA that expresses NELL2 signal peptide. The incorporation of the NELL2 signal nucleic acid or cDNA into the system expressing NELL1 peptide allows the production of the NELL1 peptide more efficiently.

The nucleic acid construct can include a nucleic acid sequence encoding a signal peptide. The nucleic acid can include an expression vector for expressing the nucleic acid sequence encoding a NELL peptide. Further, the nucleic acid sequence can include additional nucleic acids which encode reporter products to monitor levels of gene expression, or encode peptide tags which can be visualized using known methods in the art to monitor levels of peptide expression.

Nucleic acid constructs can comprise expression and cloning vectors should containing a selection gene, also termed a selectable marker, such as a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g., ampicillin, neomycin, methotrexate or tetracycline, (b) complement auxotrophic deficiencies.

Nucleic acid constructs can also include a promoter which is recognized by the host organism and is operably linked to the NELL encoding nucleic acid. Promoters are untranslated sequences located upstream from the start codon of a structural gene (generally within about 100 to 1000 bp) that control the transcription and translation of nucleic acid under their control, including inducible and constitutive promoters. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known.

A nucleic acid can be operably linked when it is placed into a functional relationship with another nucleic acid sequence. For example, DNA for a presequence or secretory leader is operably linked to DNA for a polypeptide if it is expressed as a preprotein which participates in the secretion of the polypeptide; a promoter or enhancer is operably linked to a coding sequence if it affects the transcription of the sequence; or a ribosome binding site is operably linked to a coding sequence if it is positioned so as to facilitate translation.

In one embodiment, the invention can include cells that express functional NELL peptides. For example, the cell can be a CHO cell. In one embodiment, the cell can be transfected with a nucleic acid construct encoding a NELL peptide. For example, the cell line can be transfected transiently or stably with the nucleic acid construct encoding a NELL peptide. In one embodiment, NELL expressing nucleic acids (e.g., cDNA(s) can be cloned into gene expression vector or viral particles that are competent to transfect cells (such as insect cells or Chinese hamster ovary cells (CHO cells)).

The nucleic acid sequence can also include a nucleic acid sequence encoding a NELL peptide, such as NELL1 or NELL2 peptide, in frame with a nucleic acid sequence encoding an insect secretory signal peptide.

In one embodiment, the invention can include cells that express functional NELL peptides, and can secrete functional proteins.

In one embodiment, the invention can include a polypeptide (amino acid sequence) comprising a NELL peptide, such as NELL1 or NELL2 peptide, and can include secretory signal peptide.

For example, the amino acid sequence of the NELL peptide can be selected from the group including, but not limited to human NELL1 (SEQ ID NO:2), rat NELL1 (SEQ ID NO:4), mouse NELL1 (SEQ ID NO:6), or human NELL2 (SEQ ID NO:8), rat NELL2 (SEQ ID NO:10), mouse NELL2 (SEQ ID NO:12), chicken NELL2 (SEQ ID NO:14). The amino acid sequence can also include sequences such as those with substantial similarity, such as sequences having at least about 75% sequence similarity with any portion of the sequences listed above, or contain similar active binding domains as NELL1 peptides.

Peptide Purification

In some embodiments, the invention includes a method purifying NELL1 and/or NELL2 peptides secreted into culture media, according to standard peptide purification protocols, including, but not limited to those described below.

The method can also include collecting secreted NELL peptides and/or purifying NELL peptides for use. Peptide products can be tested for activity in a variety of functional or expression assays. For example in any assay, if a NELL peptide has a significant effect over a control substance on a given parameter, the NELL peptides can be said to be functional to effect the measured parameter.

In one embodiment, whether a selected cell expresses a selected nucleic acid sequence to express and/or secrete a NELL peptide can be examined. In one embodiment, the presence, amount or and/or activity of NELL peptides can be examined.

In on embodiment, NELL peptides detected and quantified by any of a number of methods well known to those of skill in the art. These can include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

In one embodiment, Western blot (immunoblot) analysis can be used to detect and quantify the presence of NELL peptide(s) in a selected sample. This technique can include separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind a target peptide.

The assays of this invention can be scored (as positive or negative or quantity of target polypeptide) according to standard methods well known to those of skill in the art. The particular method of scoring can depend on the assay format and choice of label. For example, a Western Blot assay can be scored by visualizing the colored product produced by an enzymatic label. A clearly visible colored band or spot at the correct molecular weight can be scored as a positive result, while the absence of a clearly visible spot or band can be scored as a negative. The intensity of the band or spot can provide a quantitative measure of target polypeptide concentration.

EXAMPLES

Methods for recombinant protein production and purification are well known to those in the art with several commercial company offering protein production services. The following examples are offered to illustrate, but not to limit the claimed invention. In general expression hosts can be: bacteria, yeast and fungi, mammalian cells, plants, transgenic animals (e.g., goat milk) or it can also be cell-free expression systems such as those based on wheat germ or E. coli extracts. In general, expression elements can be Prokaryotic, Yeast, Mammalian and Plant promoters or viral promoters. Protein expression strategies can be: intra- or extracellular, fusion proteins and display strategies. Downstream processing of recombinant proteins can include: harvest, lysis, filtration, ultrafiltration, precipitation, and/or other protein processing/purification strategies that encompass protein capture, purification, polishing, and optimization.

Example 1

Expression of Nell Peptides

A cDNA fragment was ligated into the expression vector PiZT/V5-His (3.4 kb) (EcoRV site, Invitrogen) and included a melittin signal peptide, BamHI-EcoRI cDNA fragment of the mature rat NELL1 and a FLAG tag sequence. FIGS. 2A-2B are a depiction of the nucleic acid sequence of the cDNA construct used in this example, and corresponding predicted peptide sequence.

The High five cells (BTI-TN-5B1-4) were adapted to serum-free medium, and cells were transfected with the NELL1 peptide expression vector. Cells were treated with zeocin so as to select only cell populations expressing the NELL1 FLAG constructs. Surviving cell populations were confirmed to be stable transformants. Extracellular media was collected and tested for the presence of NELL1 peptide. NELL1 peptide was purified and used in functional assays described below.

FIG. 2A is an illustration of a CBB-stained SDS-PAGE gel of UnoQ-eluate containing purified NELL1 peptide. The medium was applied onto UnoQ column (Bio-Rad) as described herein. FIG. 2B shows a Western blot using anti-FLAG antibody depicting NELL1-FLAG expression in reference to a protein ladder. Peptide: 140 kDa (intracellular precursor), 130 kDa (mature form; 90 kDa peptide), 400 kDa (secreted form, homotrimer). In the example above, the productivity of the expression system was about 3 mg NELL1 peptide/L medium.

Relative to other expression systems which did not express or secrete peptide at all (such as bacterial expression, including yeast) or whose peptide production was extremely low (e.g., E. coli fused peptide system, CHO-dhfr cells, >10 mcg/L) production with the systems described (mammalian and insect cells) was surprisingly and substantially more effective at producing large amounts of functional protein.

Expression and Purification of Recombinant Rat NELL1 Protein. For production of the C-terminally FLAG-tagged NELL1 peptide by insect cells, a pIZT-NELL1-FLC plasmid was constructed by inserting the rat NELL1 cDNA fused to a FLAG epitope sequence derived from the pTB701-NELL1-FLC plasmid (Kuroda, BBRC) into insect expression vector pIZT/V5-His (Invitrogen). Furthermore, NELL1 original secretory signal sequence was replaced to honeybee mellitin signal sequence using PCR methods. High Five cells were purchased from Invitrogen, and were cultured in High Five Serum-Free Medium (Invitrogen). High Five cells were transfected with the pIZT-NELL1-FLC plasmid using FuGene6 (Roche). Forty-eight hours after transfection, cells were selected with 400 mg/ml of Zeocin (Invitrogen). Replace selective medium every 3 to 4 days until the stable expression cell line was established. NELL1 secretion was confirmed using immunoprecipitation and Western blot analyses. High five cells were found to express NELL1 peptides (140-kDa) in the culture medium.

The recombinant rat NELL1-FLC peptide was purified from the culture medium of Zeocin-resistant High Five cells by anion exchange chromatography using a UNO Q-1 column (Bio-Rad). NELL1 peptide was eluted at 500 mM NaCl.

For production of the C-terminally FLAG-tagged NELL1 peptide by COS7 cells, a pcDNA3.1-NELL1-FLC plasmid was constructed by inserting the rat NELL1 cDNA linked to a FLAG epitope sequence derived from the pTB701-NELL1-FLC plasmid into mammalian expression vector pcDNA3.1 (Invitrogen). COS7 cells were cultured in DMEM supplemented with 10% FBS. COS7 cells were transfected with the pcDNA3.1-NELL1-FLC using the endogenous NELL signal peptide plasmid and using electroporation method. Forty-eight hours after transfection, culture medium was subjected to immunoprecipitation and Western blot analyses for NELL1 peptide.

FIG. 3C is an illustration of a CBB-stained SDS-PAGE gel of UnoQ-eluate. including NELL1-FLAG. These expression studies showed that COS cells did not express functional NELL peptide, without modifying the N terminal of the NELL to increase secretion efficiency such as including a signal sequence. FIG. 3D is an illustration of a Western blot using anti-FLAG antibody depicting NELL1-FLAG expression.

Expression and Purification of Recombinant Rat NELL2 Protein. For production of the C-terminally FLAG-tagged NELL2 peptide by insect cells, a pIZT-NELL1-FLC plasmid was constructed by inserting the rat NELL2 cDNA fused to a FLAG epitope sequence derived from the pTB701-NELL2-FLC plasmid into insect expression vector pIZT/V5-His (Invitrogen). High Five cells were purchased from Invitrogen, and were cultured in High Five Serum-Free Medium (Invitrogen). High Five cells were transfected with the pIZT-NELL1-FLC plasmid using FuGene6 (Roche). Forty-eight hours after transfection, cells were selected with 400 mg/ml of Zeocin (Invitrogen). Selective media was replaced every 3 to 4 days, until the stable expression cell line was established. NELL2 expression was confirmed in culture medium was confirmed using immunoprecipitation and Western blot analyses. High five cells were found to express NELL2 peptides (140-kDa) in the culture medium.

The recombinant rat NELL2-FLC peptide was purified from the culture medium of Zeocin-resistant High Five cells by anion exchange chromatography using a UNO Q-1 column (Bio-Rad). NELL2-FLC peptide was eluted at 500 mM NaCl.

Example 2

Expression of NELL1 in Mammalian Systems

The mammalian expression system used for production of rhNELL1 by non-viral DNA delivery in this invention may include, but not limit to these commonly used stable suspension systems listed in Table 1. The relatively detailed protocols including vector design, host cell line culture, transfection and selection of stable cell line as well as purification of rhNell-1 in HEK 293 and CHO system are described below, but are well known to those in the art.

TABLE 1

Mammalian Expression System for production of rhNell-1

| System | Parental vector | Leader sequence | Gene amplification |
|---|---|---|---|
| CHO | p3Xflag-CMV | preprotrypsin | No/optinal |
| DXB11 | mp19-Lp | human tPA | DHFR/MTX |
| HEK293 | pSecTag | immunoglobulin | No/optinal |
| NS/0 or Sp2/0 | pdCs-Fc-X | light chain of Ig and Fc fragment | DHFR/MTX |
| | pEE12 | N/A | GS/MSX |

DHFR: diydrofolate reductase;
MTX: methotrxate;
GS: glutamine synthetase
MSX: methionine sulphoximine A. CHO System #1

Vector design: A cDNA fragment was ligated into the expression vector p3XFlag-CMV (Sigma). The resulting expression construct, pCMV-rhNELL3Xflag, includes a preprotrypsin leading sequence, cDNA fragment of the mature human NELL1 coding region and a 3Xflag sequences at c-terminal.

Host Cell line: The CHO-K1 were adherent cell line and can be adapted to suspension culture in serum-free medium. The construct of pCMV-rhNell-1-3Xflag was transfected by either lipofectamin (Invitrogen) or calcium phosphates treatment. The stable cell lines were selected by adding G418 (400-600 ug/ml) into the cell culture medium for about two weeks. The stable transformants were further screened for single clones with high productivity of rhNELL1 by limiting dilution. The selected stable cell lines can be expended in laboratory or industrial scale bioreactors for rhNell-1 production.

Purification procedure: rhNELL1 peptide containing media or cell lysate were purified through anti-flag antibody M2 (Sigma) affinity column at its native condition and eluted with 3Xflag peptide.

B. CHO System #2

Vector design: FIG. 4A depicts the nucleic acid sequence of the cDNA construct and amino acid sequences of three different signal peptides that were used for the constructs.

Host Cell line: The CHO-K1 were adherent cell line and can be adapted to suspension culture in serum-free medium. The construct of pcDNA3.1-hNELL1-c-myc/His, pIL2-hNELL1-c-myc/His, or pN2-hNELL1-c-myc/His were transfected by either lipofectamin (Invitrogen) or calcium phosphates treatment. The stable cell lines were selected by adding G418 (400-600 ug/ml) into the cell culture medium for about two weeks. The stable transformants were further screened for single clones with high productivity of rhNELL1 by limiting dilution. The selected stable cell lines can be expended in laboratory or industrial scale bioreactors for rhNELL1 production.

Figure 4B:
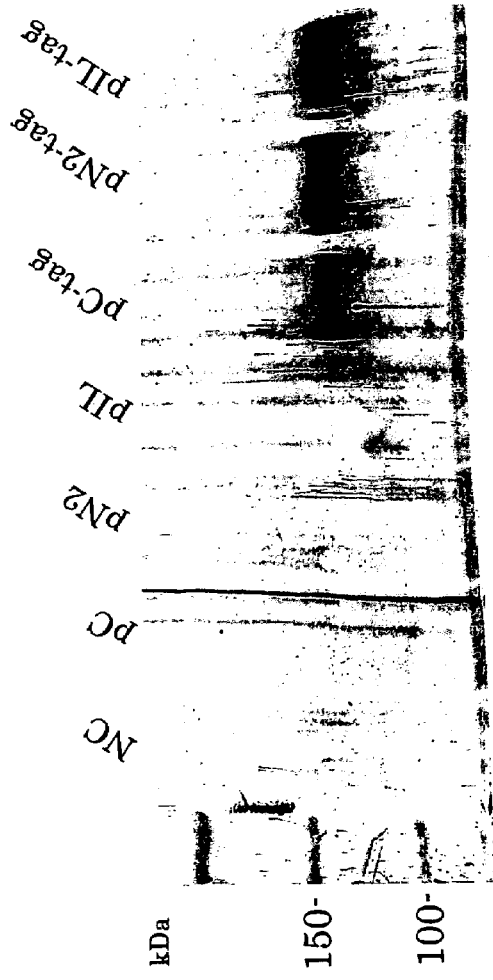
Figure 4C:
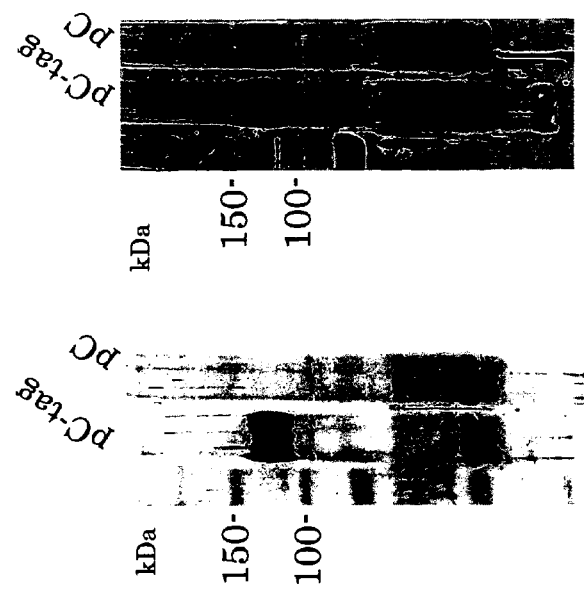

Purification procedure: rhNELL1 peptide containing media or cell lysate were purified through immunoprecipitation through anti-c-myc agarose. FIG. 4B is a Western blot with anti-c-myc antibody detecting secreting NELL1 from transfections with different constructs after immunoprecipitation using anti-c-myc agarose. FIG. 4C is a Western blot with anti-c-myc or mouse anti-human NELL1 antibodies detecting secreting NELL1 after immunoprecipitation using rabbit anti-human Nell-1 antibody-NHS activated sepharose.

C. CHO System # 3

Vector design: Proprietary cDNA constructs (from Aragnen Biosciences, Lonza, or Cytovance) using either NELL1 or NELL2 leader peptide sequences were constructed.

Host Cell line: The proprietary CHO cell lines were adherent cell line and can be adapted to suspension culture in serum-free medium. The proprietary constructs were transfected. The stable cell lines were selected by adding appropriate factors into the cell culture medium for about two weeks. The stable transformants were further screened for single clones with high productivity of rhNELL1 by limiting dilution. The selected stable cell lines can be expended in laboratory or industrial scale bioreactors for rhNELL1 production.

Purification procedure: rhNELL1 peptide containing media or cell lysate were purified through analytical and preparative protein purifications methods well known to those in the art (e.g., size, exclusion chromatography, ion exchange chromatography, affinity chromatography, immunoaffinity chromatography, high performance liquid chromatography, Concentration procedure: rhNELL1 was concentrated using lyophilization or ultrafiltration.

D: HEK293 System

Vector design: A cDNA fragment was ligated into the expression vector pSecTagA (Invitrogen). The resulting expression construct, pSec-hNell-1-Tag, includes a murine immunoglobulin K-chain leader sequence, cDNA fragment of the mature human NELL1 coding region and dual tag of Myc and His sequences at c-terminal.

Host Cell line: The human embryo kidney cell line, HEK-293 which was adapted to serum-free medium and grown in suspension format, was transfected with the NELL1 peptide expression vector, pSec-hNell-1-Tag. Cells were either cultured for a couple of days as transient transfection before collecting conditioned medium for purification of rhNell-1 or treated with Zeocin (250 ug/ml) for selection of stable expression cell line. The stable transformants were further screened for single clones with high productivity of rhNell-1 by limiting dilution. The selected stable cell lines can be expended in laboratory or industrial scale bioreactors for rhNell-1 production.

Purification procedure: rhNell-1 peptide containing media were purified through $Ni^{2+}$ affinity column at its native condition and eluted with 1M imidazole. The rhNell-1 was tested for its integrity, purity and bioactivity after extensively dialysis against at least 1000 volumes of PBS (pH 7.4) at 4° C. for 20 hrs.

In addition, the modifications of parental vectors for replacing existing leader sequence with a new one such as rat serum albumin, CD33, tPA and human interlukin-2 leader sequence or adding gene amplification target such as DHFR or GS into the backbone sequence will result in new expression vectors and systems. In this invention, the native signal peptide of human Nell-1 is not effective enough to guide the protein secretion and sometimes even the external Leading sequence didn't work well, either. Thus, the construction of expression vector with in frame fusion of a small natural secretory protein such as human granulocyte-macrophage colony stimulating factor (GM-CSF) by a spacer containing intraprotein His tag and proteolytic cleavage site as "MPH-HHHHHGGGDDDDKDPM" (SEQ ID NO: 18) might be needed. The epitope tags used for purification of Nell-1 can be one of the following: 6XHistidines, 3XFlag, Myc, GST (glutathione S-transferase), EGFP or CTHS (C-terminal half of SUMO which stands for small ubiquitin modifying protein) etc, but also could be dual of His plus Myc as listed plasmid pSecTag in Table 1 (supra).

Furthermore, the dicistronic or multicistronic vectors using IRES might be constructed for regulatory or inducible expression of rhNell-1 under certain circumstances. The genetic modifications of host cell lines for gaining longer lasting proliferation and delayed apoptosis or compatible with special requests such as Tet (tetracycline) inducible system and Flp-In specific site integration system will be considered for improvement of rhNell-1 production.

Besides the stable expression of system for production of rhNell-1 mentioned above, we would not exclude the possibility to establish a large-scale transient transfection (LST) approach using multi-milligram purified plasmid vector (pREP4) to transfect HEK 293 or BHK suspension cells with cationic polymer PEI as backup alternative or complimentary to stable system.

Example 3

Purification of Nell2 Protein from Culture Medium

High Five cells carrying pIZT-FLC-NELL2 were cultured for about three days in serum free culture medium (1 L). The culture medium was centrifuged at. 3000×g for 5 minutes and the supernatant was collected. PMSF was added to a final concentration of 1 mM. Saturated ammonium sulfate solution (80% saturation (v/v) was added and the solution kept at 4 degrees for 1 hour. The solution was centrifuged at 15000×g for 30 min. and precipitate collected. Precipitate was dissolved in 50 ml of 20 mM Tris-HCl (pH 8.0), 1 mm EDTA at 4 degree and applied onto an anion-exchange chromatography UnoQ column (6 ml, Bio-Rad) equilibrated in 20 mM Tris-HCl (pH 8.0), 1 mM EDTA at 4 degree (1 ml/min speed by FPLC (Amersham-Pharmacia). The column was thoroughly washed with the same buffer.

The binding protein was then eluted by the gradation from 0 M to 1.5 M NaCl in the same buffer. The NELL2-FLAG fractions were identified by Western blotting using anti-Flag M2 (Sigma) Ab. The positive fractions were collected into one tube. Final product was dialyzed in the seamless cellulose tube (Wako, cutoff MW 12000) against 1 L PBS for overnight at 4 degree. The product was stored at −70 degree.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of expressing a peptide in a mammalian cell, said method comprising:
   providing a nucleic acid construct including at least a nucleic acid encoding at least a nel-like (NELL) peptide in frame with a nucleic acid encoding a heterologous eukaryotic secretory signal peptide;
   transfecting a mammalian cell with said nucleic acid construct; and
   culturing said mammalian cell under conditions that permit expression of the NELL peptide.

2. The method of claim 1, wherein the mammalian cell is a Chinese hamster ovary (CHO) cell.

3. The method of claim 2, wherein the nucleic acid encodes NELL1 or NELL2,
   wherein NELL1 is selected from the group comprising: SEQ ID NO:1, SEQ ID NO:2, SEQ ID NO:3, SEQ ID NO:4, SEQ ID NO:5, and SEQ ID NO:6,
   wherein NELL2 is selected from the group consisting of: SEQ ID NO:7, SEQ ID NO:8, SEQ ID NO:9, SEQ ID NO:10, SEQ ID NO:11, SEQ ID NO:12, SEQ ID NO:13, and SEQ ID NO:14.

4. The method of claim 2, further comprising collecting NELL peptide secreted from the cell line; and
   substantially purifying the NELL peptide.

5. The method of claim 1, further comprising
   collecting the NELL peptide secreted from the cell line; and
   substantially purifying the NELL peptide.

6. The method of claim 4, further comprising
   testing the activity of the NELL peptide to induce bone formation.

7. The method of claim 5, further comprising
   testing the activity of the NELL peptide to induce bone formation.

8. The method of claim 4, wherein the purifying includes chromatography purification.

9. The method of claim 5, wherein the purifying includes chromatography purification.

10. A nucleic acid construct for expressing a nel-like (NELL) peptide in a mammalian cell, said nucleic acid construct comprising at least a nucleic acid encoding at least a NELL peptide in frame with a nucleic acid encoding a heterologous eukaryotic secretory signal peptide.

11. The nucleic acid construct of claim 10, wherein the nucleic acid encodes NELL1 or NELL2,
    wherein the NELL1 is selected from the group comprising: SEQ ID NO:1, SEQ ID NO:2, SEQ ID NO:3, SEQ ID NO:4, SEQ ID NO:5, and SEQ ID NO:6,
    wherein NELL2 is selected from the group consisting of: SEQ ID NO:7, SEQ ID NO:8, SEQ ID NO:9, SEQ ID NO:10, SEQ ID NO:11, SEQ ID NO:12, SEQ ID NO:13, and SEQ ID NO:14.

12. The nucleic acid construct of claim 10, wherein the mammalian cell is a Chinese hamster ovary (CHO) cell.

13. A mammalian cell line for expressing a nel-like (NELL) peptide, said cell line including a nucleic acid construct comprising at least a nucleic acid encoding at least a NELL peptide in frame with a nucleic acid encoding a heterologous eukaryotic secretory signal peptide.

14. The cell line of claim 13, wherein the mammalian cell line comprises a Chinese hamster ovary (CHO) cell.

15. The cell line of claim 14, wherein the CHO cell secretes NELL1 or NELL2 peptide.

16. The cell line of claim 14, wherein the nucleic acid encodes NELL or NELL2 peptide,
    wherein NELL1 is selected from the group comprising: SEQ ID NO:1, SEQ ID NO:2, SEQ ID NO:3, SEQ ID NO:4, SEQ ID NO:5, or SEQ ID NO:6, and
    wherein NELL2 is selected from the group consisting of: SEQ ID NO:7, SEQ ID NO:8, SEQ ID NO:9, SEQ ID NO:10, SEQ ID NO:11, SEQ ID NO:12, SEQ ID NO:13, and SEQ ID NO:14.

* * * * *